(12) United States Patent
ElShamy

(10) Patent No.: US 9,303,069 B2
(45) Date of Patent: Apr. 5, 2016

(54) PEPTIDES FOR TREATING CANCER

(71) Applicant: University of Mississippi Medical Center, Jackson, MS (US)

(72) Inventor: Wael M. ElShamy, Madison, MS (US)

(73) Assignee: University of Mississippi Medical Center, Jackson, MS (US)

( * ) Notice: Subject to any disclaimer, the term of this patent is extended or adjusted under 35 U.S.C. 154(b) by 0 days.

(21) Appl. No.: 14/269,675

(22) Filed: May 5, 2014

(65) Prior Publication Data

US 2015/0315244 A1   Nov. 5, 2015

(51) Int. Cl.
| | | |
|---|---|---|
| *C07K 14/00* | (2006.01) | |
| *C12N 15/113* | (2010.01) | |
| *A61K 38/16* | (2006.01) | |
| *A61K 33/24* | (2006.01) | |
| *A61K 31/337* | (2006.01) | |

(52) U.S. Cl.
CPC ............... *C07K 14/00* (2013.01); *A61K 31/337* (2013.01); *A61K 33/24* (2013.01); *A61K 38/16* (2013.01); *C12N 15/1135* (2013.01)

(58) Field of Classification Search
CPC ............ A61K 2300/00; A61K 31/713; A61K 39/39558; A61K 45/06; C07K 14/47; C07K 16/32; C07K 2316/96; C07K 2317/24; C07K 14/00; C07K 2319/00; C07K 2319/01; C07K 14/435
See application file for complete search history.

(56) References Cited

U.S. PATENT DOCUMENTS

| | | | | |
|---|---|---|---|---|
| 8,841,414 B1 * | 9/2014 | Raucher et al. | ............... | 530/350 |
| 2011/0076342 A1 * | 3/2011 | Malkas et al. | ............... | 424/649 |

OTHER PUBLICATIONS

Kristen Sadler, Design of Novel Cell Penetrating Peptides, Peptides: The Wave of the Future, American Peptide Society, 2001.*
UniProt Protein Database, Protein Accession Q5YLB2, Breast cancer type 1 susceptibility protein, accessed on Mar. 3, 2015.*
Chock K, Allison JM, ElShamy WM. (2010a). BRCA1-IRIS overexpression abrogates UV-induced p38MAPK/p53 and promotes proliferation of damaged cells. Oncogene. 29(38), 5274-5285.
Chock KL, Allison JM, Shimizu Y, ElShamy WM. (2010b). BRCA1-IRIS overexpression promotes cisplatin resistance in ovarian cancer cells. Cancer Res. 70(21), 8782-8791.
ElShamy WM, and Livingston, DM. (2004). Identification of BRCA1-IRIS, a BRCA1 locus product. Nat. Cell Biol. 6(10), 954-967.
Hao L, ElShamy WM. (2007). BRCA1-IRIS activates cyclin D1 expression in breast cancer cells by downregulating the JNK phosphatase DUSP3/VHR. Int. J. Cancer. 121(1), 39-46.
Nakuci E, Mahner S, Direnzo J, ElShamy WM. (2006). BRCA1-IRIS regulates cyclin D1 expression in breast cancer cells. Exp. Cell Res. 312(16), 3120-3131.
Paul, et al.; BRCA1-IRIS inactivation sensitizes ovarian tumors to cisplatin; Oncogene; 2014; pp. 1-17.
Shimizu Y, Mullins N, Blanchard Z, ElShamy WM. (2012a). BRCA1/p220 loss triggers BRCA1-IRIS overexpression via mRNA stabilization in breast cancer cells. Oncotarget. 3(3), 299-313.
Shimizu Y, Luk H, Florio D, Miron P, Griswold M, Iglehart D, Hernandez B, Killeen J, ElShamy WM. (2012b). BRCA1-IRIS overexpression promotes formation of aggressive breast cancers. PLoS One. 7(4), e34102.

* cited by examiner

*Primary Examiner* — James H Alstrum Acevedo
*Assistant Examiner* — Erinne Dabkowski
(74) *Attorney, Agent, or Firm* — Stiles & Harbison, PLLC; Terry L. Wright

(57) ABSTRACT

The present disclosure relates to peptides for treating cancer, wherein the peptides suppress BRCA1-IRIS expression or activity. The peptides may include an amino acid sequence as set forth in SEQ ID NO: 1 and/or SEQ ID NO: 2. Further, the present disclosure provides methods for treating cancer, wherein the cancer may be breast or ovarian cancer, including administering one of said peptides to a subject in need thereof.

18 Claims, 31 Drawing Sheets

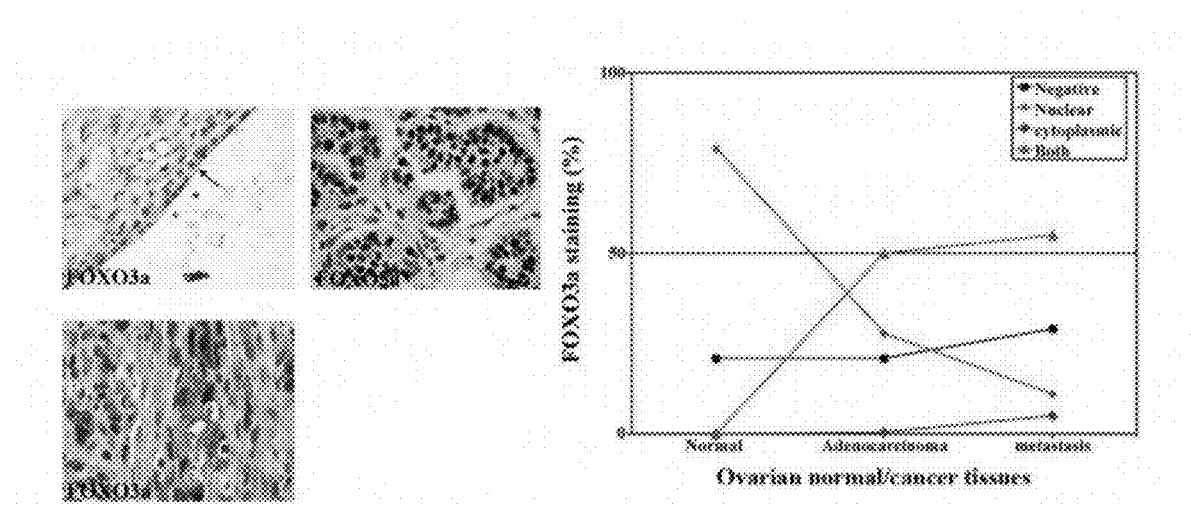
FIG. 9
FIG. 10
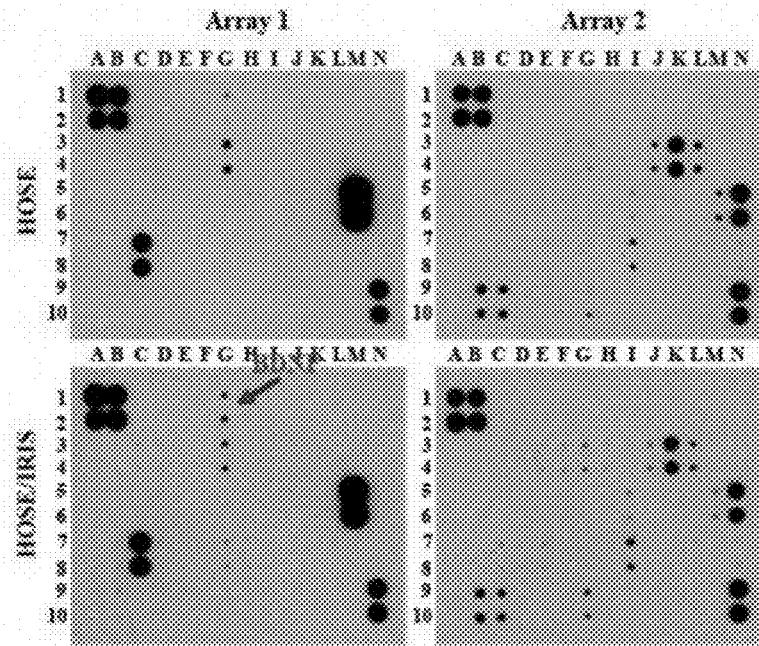
FIG. 11

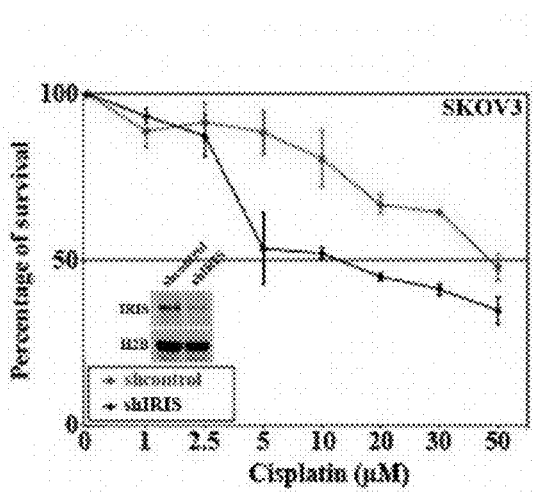
FIG. 23
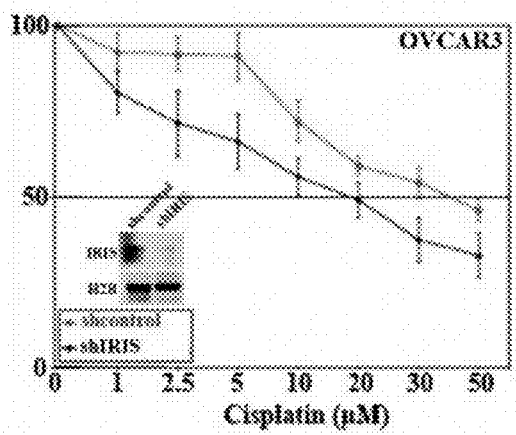
FIG. 24
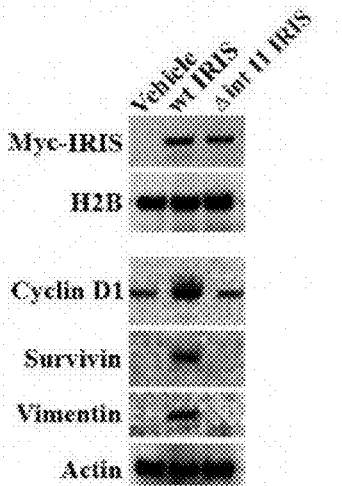
FIG. 25
RRIRPRPPRLPRPRPRPLPFPRPGIGTRFLCLPQSIYRSELNVYAFGEHILQISKYS
━━━━━━━━━━━━━━━━━━━━━ ━━━━━━━━━━━━━━━━━━━━━━━━━━━━━━━━
　　Penetrating signal　　　　　　Intron 11 IRIS ppetide
FIG. 26

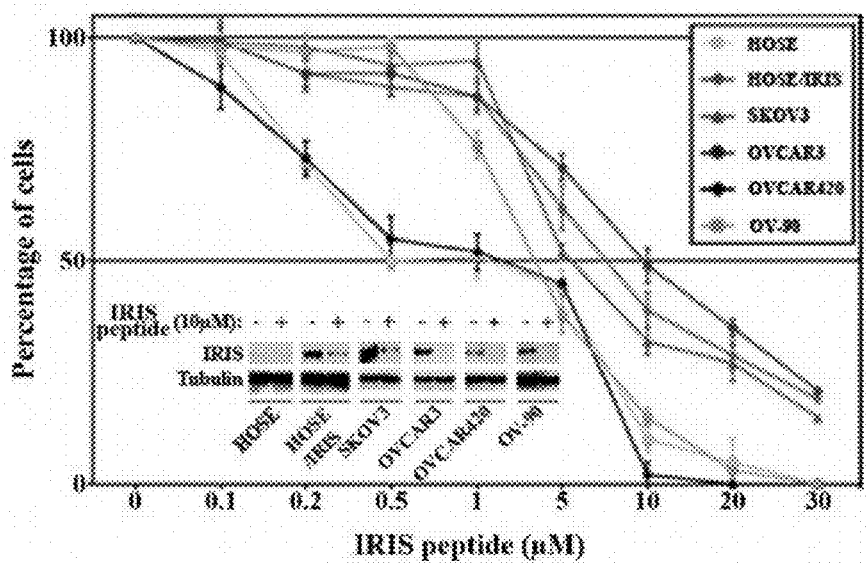
FIG. 27
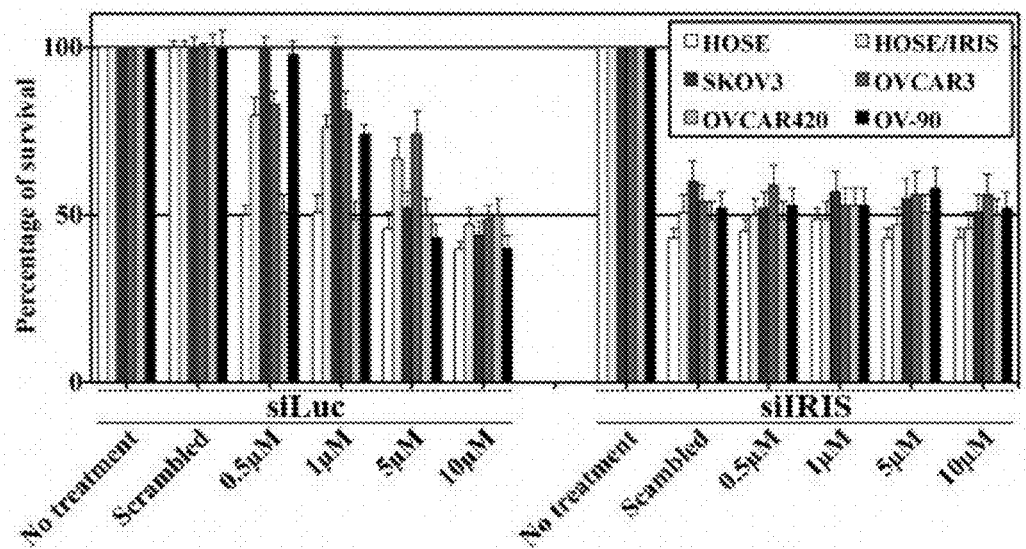
FIG. 28  FIG. 29

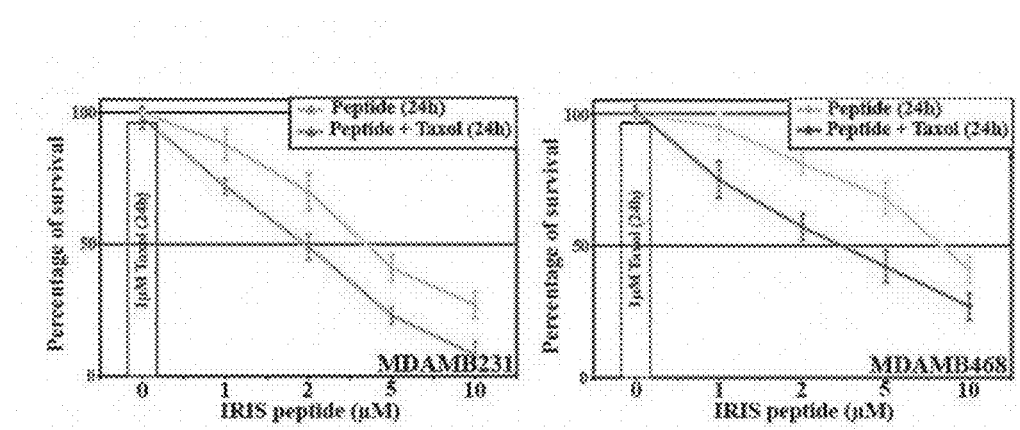
FIG. 85
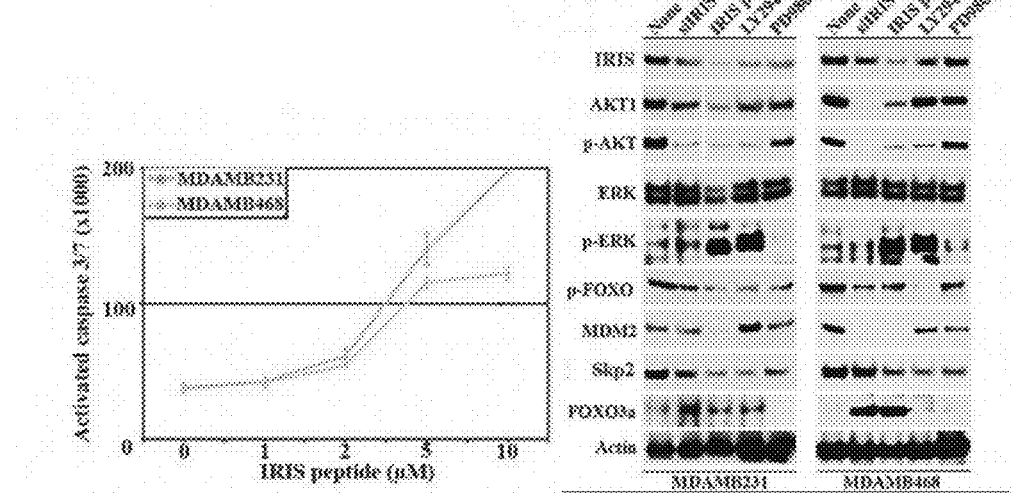
FIG. 86  FIG. 87

SEQUENCE LISTING

```
<160> NUMBER OF SEQ ID NOS: 2

<210> SEQ ID NO 1
<211> LENGTH: 34
<212> TYPE: PRT
<213> ORGANISM: Artificial Sequence
<220> FEATURE:
<223> OTHER INFORMATION: Synthesized BRCA1-IRIS Peptide
<220> FEATURE:
<221> NAME/KEY: PEPTIDE
<222> LOCATION: (1)..(34)

<400> SEQUENCE: 1

Gly Ile Gly Thr Arg Phe Leu Cys Leu Pro Gln Ser Ile Tyr Arg Ser
1               5                   10                  15

Glu Leu Asn Val Tyr Ala Phe Gly Glu His Ile Leu Gln Ile Ser Lys
            20                  25                  30

Tyr Ser

<210> SEQ ID NO 2
<211> LENGTH: 23
<212> TYPE: PRT
<213> ORGANISM: Artificial Sequence
<220> FEATURE:
<223> OTHER INFORMATION: Synthesized Penetrating Peptide
<220> FEATURE:
<221> NAME/KEY: PEPTIDE
<222> LOCATION: (1)..(23)

<400> SEQUENCE: 2

Arg Arg Ile Arg Pro Arg Pro Pro Arg Leu Pro Arg Pro Arg Pro Arg
1               5                   10                  15

Pro Leu Pro Phe Pro Arg Pro
            20
```

PEPTIDES FOR TREATING CANCER

TECHNICAL FIELD

The present disclosure relates to peptides for treating cancer, to compositions comprising such peptides, and to methods of using the peptides.

BACKGROUND

Cancer continues to be a leading cause of death with over 1.6 million new cases of cancer being diagnosed in 2012 and over 500,000 people dying from cancer in the United States alone in 2012. For example, in the United States, breast cancer affects over 250,000 women every year, and represents the most common form of cancer in females. Indeed, it has been found that 1 out of every 8 women in the United States will develop invasive breast cancer during their lifetime and that almost 40,000 women die of breast cancer each year.

Meanwhile, epithelial ovarian cancer is the leading cause of death among gynecologic malignancies in the United States (Auersperg, 2013), with more than 21,000 cases reported and nearly 15,000 deaths in 2011. The standard treatment involves surgical de-bulking, followed by chemotherapy with, for example, carboplatin and paclitaxel. Most patients initially respond to these treatments; however a significant number of patients eventually develop drug resistance resulting in relapse, cancer progression, and death. Furthermore, mortalities associated with ovarian cancer are often due to late diagnosis and/or to acquired platinum-resistant recurrence.

Despite efforts to improve treatment and detection of cancer, cancer survival has still not improved significantly over the past two decades for a number of cancer types due, at least in part, to the numerous subtypes of certain cancers and due to the various mechanisms responsible for the development of those cancer subtypes.

Therefore, novel therapeutic approaches that can target drug-resistant tumor cells are very much in need (Matsuo et al., 2010, Banerjee and Gore, 2009). In addition, elucidating the mechanisms leading to drug resistance should provide basis for development of drugs able to re-establish chemosensitivity.

BRIEF SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of features.

The present disclosure provides, in some embodiments, an isolated peptide comprising the amino acid sequence set forth in SEQ ID NO: 1. In certain embodiments, the isolated peptide further comprises the amino acid sequence set forth in SEQ ID NO: 2. Further, in various embodiments, the peptide of the present disclosure may be no more than 10000, no more than 1000, no more than 500, and/or no more than 100 amino acids in length. Moreover, in some embodiments of the present disclosure, the isolated peptide is an active agent. In certain embodiments, the isolated peptide of the present disclosure includes a cell-penetrating peptide, and in at least one embodiment, the cell-penetrating peptide comprises the amino acid sequence set forth in SEQ ID NO: 2.

Moreover, in some embodiments, the presently-disclosed subject matter provides a pharmaceutical composition that includes an isolated peptide comprising the amino acid sequence set forth in SEQ ID NO: 1. In some embodiments, the pharmaceutical composition comprises an active agent, such as a peptide comprising the amino acid sequence set forth in SEQ ID NO: 1. And, in some embodiments, the pharmaceutical composition comprises a cell-penetrating peptide, such as a peptide comprising the amino acid sequence set forth in SEQ ID NO: 2. In certain embodiments, the pharmaceutical further comprises a pharmaceutically-acceptable carrier.

Further, the present disclosure includes, in some embodiments a fusion peptide, wherein fusion peptide comprises (i) a first peptide comprising the amino acid sequence set forth in SEQ ID NO: 1 and (ii) a second peptide comprising the amino acid sequence set forth in SEQ ID NO: 2. In certain embodiments, the fusion peptide is no more than 10000, no more than 1000, no more than 500, and/or no more than 100 amino acids in length. In certain embodiments, an N-terminus of the first peptide is connected to a C-terminus of the second peptide. In some embodiments, the present disclosure provides a method of treating cancer, comprising administering to a subject in need thereof a therapeutically effective amount of a fusion peptide described herein.

Additionally, certain embodiments of the present disclosure provide further methods of treating cancer. One such method comprises the step of administering, to a subject in need thereof, a therapeutically effective amount of a peptide comprising the amino acid sequence set forth in SEQ ID NO: 1. In some embodiments, the administered peptide further comprises the sequence set forth in SEQ ID NO: 2. And in certain embodiments, the administered peptide comprises a fusion peptide. In some embodiments, the cancer is breast cancer and/or ovarian cancer.

In some embodiments, the methods of the present disclosure further comprise administering a chemotherapeutic agent to a subject. The chemotherapeutic agent may comprise, in certain embodiments, cisplatin and/or paclitaxel.

Other embodiments of the presently disclosed subject matter provide methods for treating a subject, comprising administering to a subject having cancer a composition comprising an isolated peptide, wherein the isolated peptide comprises the amino acid sequence set forth in SEQ ID NO: 1, and further wherein the isolated peptide is administered in an effective amount to treat the cancer.

Additional embodiments recite methods for treating a subject, comprising administering a therapeutically effective amount of an isolated peptide that selectively inhibits BRCA1-IRIS, wherein the isolated peptide comprises SEQ ID NO: 1, and a chemotherapeutic agent to a subject having cancer.

In some embodiments, the methods of the present disclosure further comprise the step of (i) administering an amount of shRNA to the subject, wherein the shRNA reduces the expression of BRCA1-IRIS and/or (ii) administering an amount of siRNA to the subject, wherein the siRNA reduces the expression of BRCA1-IRIS.

Further advantages of the presently-disclosed subject matter will become evident to those of ordinary skill in the art after a study of the description, Figures, and non-limiting Examples in this document.

BRIEF DESCRIPTION OF THE FIGURES

FIGS. 1-10 show BRCA1-IRIS, FOXO3a and survivin levels in ovarian tumor samples, wherein paraffin-embedded tissue microarray sections were examined by immunohistochemistry with anti-BRCA1-IRIS, survivin and FOXO3a mAb.

FIG. 1 presents normal ovarian, grade 1 or 3 and metastatic tissues stained with BRCA1-IRIS antibody, wherein immunoreactivity is shown as brown-stained areas and unstained areas are indicated by hemotoxylin counterstaining.

FIG. 2 provides quantitative analysis data of BRCA1-IRIS staining in all ovarian (normal and cancer) tissues.

FIG. 3 provides quantitative analysis data of BRCA1-IRIS staining in ovarian adenocarcinoma tissues.

FIG. 4 provides quantitative analysis data of BRCA1-IRIS staining in ovarian metastatic tissues.

FIG. 5 shows normal ovarian, adenocarcinoma and metastatic tissues stained with survivin antibody.

FIG. 6 displays a quantitative analysis of survivin staining in all ovarian (normal and cancer) tissues.

FIG. 7 provides quantitative analysis data of survivin staining in ovarian adenocarcinoma tissues.

FIG. 8 provides quantitative analysis data of survivin staining in ovarian metastatic tissues.

FIG. 9 shows normal ovarian, adenocarcinoma and metastatic tissues stained with FOXO3a antibody. The arrow in each of the top left images of FIG. 1, FIG. 5 and FIG. 9 denote a BRCA1-IRIS and survivin positive but FOXO3a negative cell.

FIG. 10 provides a quantitative analysis of FOXO3a staining in all ovarian tissues, adenocarcinoma or metastatic tissues. Notably, there is a correlation between FOXO3a localization and tumor aggressiveness.

FIGS. 11-19 provide analysis of intrinsic or cisplatin-acquired pathways downstream of BRCA1-IRIS overexpression. Indeed, FIG. 11 shows analysis of cytokines secreted from HOSE versus HOSE/IRIS.

FIG. 12 shows the expression of the indicated proteins, IRIS, H2B, TrkB, p-TrkB, EGFR, ErbB2, ErbB3 and NRG1, in HOSE versus SKOV3 and OVCAR3 cells expressing shcontrol versus shIRIS.

FIG. 13 shows the expression of the indicated proteins, PTEN, AKT, p-AKT, ERK, p-FOXO, MDM2, Skp2, and FOXO3a, in HOSE versus SKOV3 and OVCAR3 cells expressing shcontrol versus shIRIS.

FIG. 14 shows the expression of the indicated proteins, JNK, p-JNK, Cyclin D1, p27, NF-κB/p65, Bcl-1, Survivin, and Actin, in HOSE versus SKOV3 and OVCAR3 cells expressing shcontrol versus shIRIS.

FIG. 15 is a schematic summary of the data presented in FIG. 11-14.

FIG. 16 is a graph summarizing the effect(s) of the indicated inhibitor(s) on the survival of HOSE versus HOSE/IRIS cells.

FIG. 17 shows the effect of cisplatin at different concentrations on the expression of the indicated proteins, IRIS, H2B, TrkB, EGFR, ErbB2, and ErbB3, in HOSE versus HOSE/IRIS cells.

FIG. 18 shows the effect of cisplatin at different concentrations on the expression of the indicated proteins, PTEN, AKT2, p-AKT, p-FOXO, FOXO3a, and Actin, in HOSE versus HOSE/IRIS cells.

FIG. 19 shows the effect of cisplatin at different concentrations on the expression of the indicated proteins, Cyclin D1, p27, p21, Survivin, Bcl-2, and Bcl-xL, in HOSE versus HOSE/IRIS cells.

FIG. 23 shows the effect of BRCA1-IRIS silencing and/or inactivation on the survival of SKOV3 ovarian cancer cells.

FIG. 24 shows the effect of BRCA1-IRIS silencing and/or inactivation on the survival of OVCAR3 ovarian cancer cells.

FIG. 25 identifies the oncogenic domain in BRCA1-IRIS. HOSE cells were transfected with cDNA that express empty vector (vehicle), Myc-tagged wild type (wt IRIS), or mutant BRCA1-IRIS cDNA (i.e. missing the intron domain part: Δint 11 IRIS). Chromatin or total extracts were isolated and analyzed for the expression of Myc-IRIS, Cyclin D1, survivin and vimentin.

FIG. 26 provides an intron 11 IRIS peptide of SEQ ID NO: 1 (right underlined portion) fused to a cell/nucleus penetrating signal of SEQ ID NO: 2 at its N-terminus (left underlined portion), hereafter referred to as "IRIS peptide" and/or "BRCA1-IRIS peptide" and/or "BRCA1-IRIS inhibitor(y) peptide". The left underlined portion represents the penetrating signal in BRCA1-IRIS inhibitory peptide and the right underlined portion represents the actual domain of BRCA1-IRIS, i.e. the intron 11.

FIG. 27 is a graph illustrating the effect(s) of the inhibitory BRCA1-IRIS peptide on the survival of HOSE and different ovarian cancer cell lines.

FIG. 28 shows the percentage of survival of HOSE, HOSE/IRIS, SKOV3, OVCAR3, OVCAR420, and OV-90 cells that were transfected with luciferase siRNA for 48 hours before they were exposed to different concentrations of IRIS peptide for another 24 hours. The percentages of survival following the two treatments are shown in FIG. 28.

FIG. 29 shows the percentage of survival of HOSE, HOSE/IRIS, SKOV3, OVCAR3, OVCAR420, and OV-90 cells that were transfected with BRCA1-IRIS siRNA for 48 hours before they were exposed to different concentrations of IRIS peptide for another 24 hours. The percentages of survival following the two treatments are shown in FIG. 28. Since no additive cell death was measured in BRCA1-IRIS silenced cells compared to control silenced cells after IRIS peptide addition, the peptide targets BRCA1-IRIS specifically.

FIG. 65 shows, in the line graph, tumor volumes following no treatment (uppermost line at day 16, n=6), cisplatin treatment (second line from top at day 16, n=6), IRIS peptide treatment (third line from top at day 16, n=6) and both (lowermost line at day 16, n=6). As shown, BRCA1-IRIS inactivation inhibits ovarian tumor formation and sensitizes ovarian tumors to cisplatin.

FIG. 85 shows that paclitaxel at 1 μM had no effect on the survival of MDA-MB-231 (white bar in left panel) or MDA-MB-468 (white bar in right panel). Gradual survival decrease in all cell lines in the presence of increasing concentrations of IRIS peptide (lighter lines in left and right) and augmentation of these effects by the combination with 1 μM paclitaxel (darker lines in left and right). BRCA1-IRIS inactivation using an inhibitory peptide sensitizes tumor cells to low paclitaxel concentrations. Values represent the means of experiments that were performed in triplicates, done three separate times.

FIG. 86 shows the gradual increase in activated caspase 3/7 in MDA-MB-231 and MDA-MB-468 cells following exposure to increasing concentrations of IRIS peptide. Values represent the means of experiments that were performed in triplicates done three separate times.

FIG. 87 shows the expression of the indicated proteins in MDA-MB-231 and MDA-MB-468 cells following the transfection of BRCA1-IRIS siRNA, exposure to 5 μM IRIS peptide or 10 μM of PI3'K/AKT inhibitor (LY294002) or ERK1/2 inhibitor (PD98059).

DETAILED DESCRIPTION OF EXEMPLARY EMBODIMENTS

Figure 1:
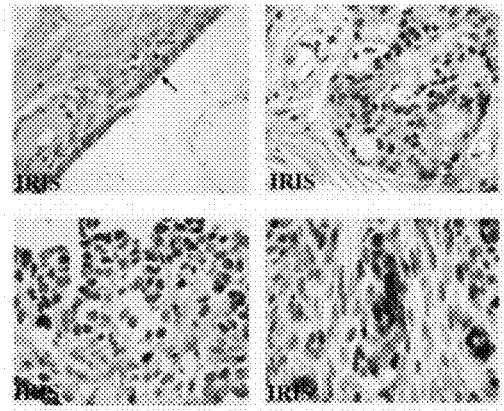
Figure 2:
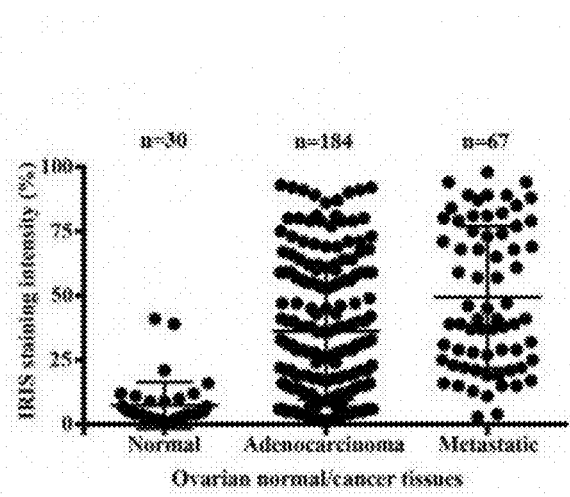
Figure 3:
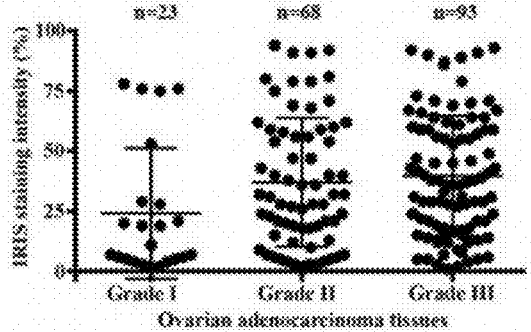
Figure 4:
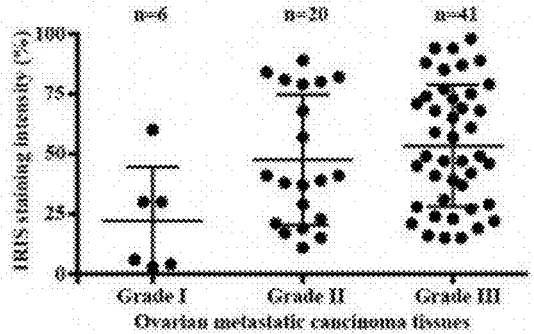
Figure 5:
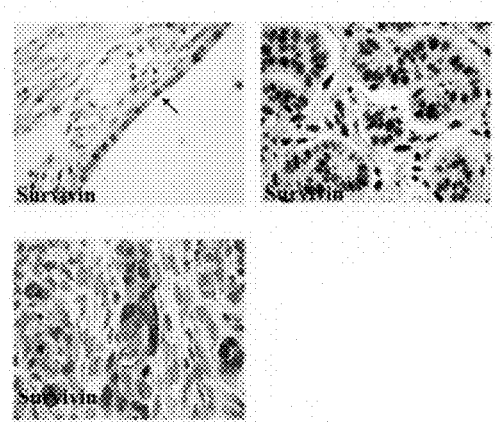
Figure 6:
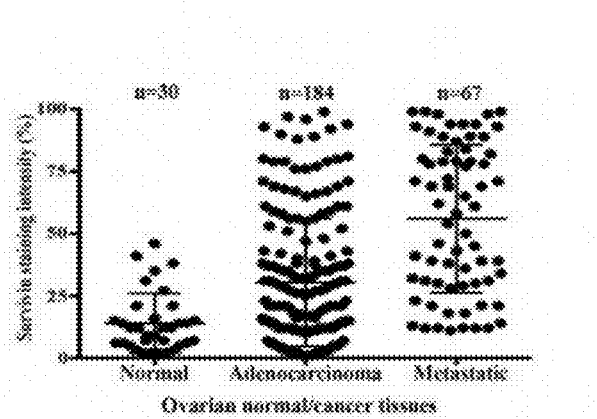
Figure 7:
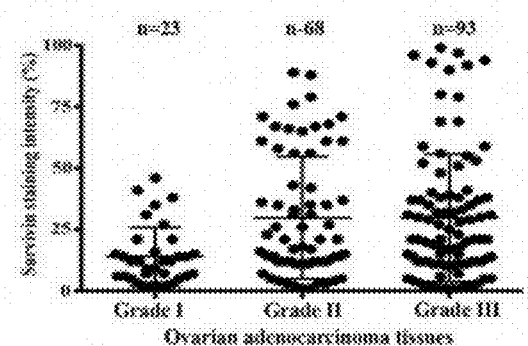
Figure 8:
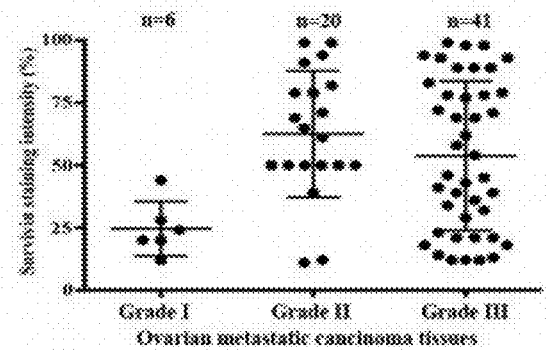

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

While the following terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of cells, and so forth.

Unless otherwise indicated, all numbers expressing quantities, properties, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional components or limitations described herein or otherwise useful.

The terms "polypeptide", "protein", and "peptide", which are used interchangeably herein, refer to a polymer of the 20 protein amino acids, including modified amino acids (e.g., phosphorylated, glycated, etc.) and amino acid analogs, regardless of size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein", "polypeptide" and "peptide" are used interchangeably herein when referring to a gene product and fragments thereof. Thus, exemplary polypeptides include gene products, naturally occurring proteins, homologs, orthologs, paralogs, fragments and other equivalents, variants, fragments, and analogs of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide. Thus, an identified fragment of a peptide (e.g., by mass spectrometry) is intended to encompass the fragment as well as the full-length peptide. As such, determining an amount of a biomarker in a sample can include determining an amount of the full-length biomarker polypeptide, modified variants, and/or fragments thereof.

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. One skilled in the art will recognize that any number of suitable common techniques can be used to introduce the siRNAs into a target cell, including nanoparticles, recombinant viruses, and liposomes.

In some embodiments, a subject will be administered an effective amount of the composition. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compositions employed; the duration of the treatment; drugs used in combination or coincidental with the specific compositions employed and like factors well known in the medical arts. For example, it is well within the skill of the art to start doses of a composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

The terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As noted, the term "peptide", as used herein, refers to a polymer of amino acids, or amino acid analogs, regardless of its size or function. In some embodiments, the term "fusion polypeptide" is used herein to generally refer to a polypeptide formed from two or more distinct peptides. The two or more distinct peptides of the fusion polypeptide may, in some embodiments, be fused, conjugated, bonded, linked, and/or otherwise connected to one another. In some embodiments, the peptide is an active agent, wherein the term "active agent" is used herein to refer to a compound or entity that alters, promotes, speeds, prolongs, inhibits, activates, eliminates, or otherwise affects biological and/or chemical events in a subject. Furthermore, a peptide according to the present disclosure also has an N-terminus and a C-terminus. Amino acid sequences provided herein are written from N-terminus (left) to C-terminus (right), unless otherwise noted.

The present disclosure further provides a nucleic acid, which codes for the inventive peptide described herein, be it a fusion peptide or a fragment, analog or variant thereof. Any nucleic acid coding for a peptide of the present disclosure is encompassed by the present disclosure. Moreover, due to degeneracy of the genetic code, a plurality of nucleic acid sequences may code for a peptide of the present disclosure. Further, a nucleic acid molecule within the scope of the present disclosure may contain the nucleic acid coding for the peptide and, additionally, further nucleotide sequences.

In some embodiments, the peptide of the present disclosure comprises a sequence according to SEQ ID NO: 1 (GIGTR-FLCLPQSIYRSELNVYAFGEHILQISKYS) or a sequence having at least 95% sequence identity with SEQ ID NO: 1. In some embodiments, the present disclosure provides "IRIS peptide" and/or "BRCA1-IRIS peptide" and/or "BRCA1-IRIS inhibitor(y) peptide", which comprises the sequence of SEQ ID NO: 1. Moreover, in certain embodiments, BRCA1-IRIS peptide is used for the treatment of cancer, such as breast cancer and/or ovarian cancer.

In some embodiments, the present disclosure provides an isolated peptide comprising the amino acid sequence set forth in SEQ ID NO: 1. In certain embodiments, the peptide is no more than 10000 amino acids in length, in certain embodiments, the peptide is no more than 1000 amino acids in length, in certain embodiments, the peptide is no more than 100 amino acids in length, and in some embodiments, the peptide is no more than 80 amino acids in length.

In some embodiments, the peptide of the present disclosure comprises a sequence according to SEQ ID NO: 2 (RRIR-PRPPRLPRPRPRPLPFPRP) or a sequence having at least 95% sequence identity with SEQ ID NO: 2. And in some embodiments, the peptide of the present disclosure comprises a sequence according to SEQ ID NO: 1 and a sequence according to SEQ ID NO: 2.

In some embodiments, the peptide of the present disclosure can be a fusion peptide that includes at least two distinct peptides or a variant, analog, fragment or derivative thereof. In some embodiments, the fusion peptide comprises a peptide having at least 80%, at least 85% and/or at least 90% sequence homology with SEQ ID NO: 1.

The peptide that is a fusion peptide can include, for example, a first peptide that comprises an active agent and a second peptide that comprises a penetrating peptide, such as a cell-penetrating and/or a nucleus-penetrating peptide. Penetrating peptides generally are peptides that trigger, accelerate, activate, or facilitate the uptake of the penetrating peptide and/or any molecule bound thereto. In some embodiments, the peptide of the present disclosure is a fusion peptide that comprises a penetrating peptide and a peptide comprising the sequence represented by SEQ ID NO: 1. In certain embodiments, the peptide of the present disclosure is a fusion peptide that includes a first peptide comprising the sequence represented by SEQ ID NO. 1 and a second peptide comprising the sequence represented by SEQ ID NO: 2.

Some embodiments of a fusion peptide according to the present disclosure provide a peptide, i.e. a fusion peptide or its analogs, fragments, variants or derivatives, having a first peptide component comprising the sequence represented by SEQ ID NO: 1, wherein the N-terminus of the first peptide is linked, fused and/or bonded to the C-terminus of a second peptide or vice versa. Further, in some embodiments, the second peptide comprises a sequence represented by SEQ ID NO: 2.

The peptide(s) of the present disclosure are substantially pure and essentially free of other substances with which they may be found in nature or in in vivo systems to the extent practical and appropriate for their intended use. Indeed, the peptides of the present disclosure are sufficiently pure and sufficiently free from other biological constituents of their host cells so as to be useful in, for example, producing pharmaceutical preparations or sequencing. Moreover, because a peptide of the present disclosure may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in vivo.

BRCA1-IRIS overexpression promotes the generation of breast, ovarian and other cancer stem cells that self-renew, evade/metastasize, are drug resistant and/or reoccur. Accordingly, a silencer/inhibitor of BRCA1-IRIS was developed, which is directed to preventing or reducing the risk of the occurrence of breast, ovarian and other types of cancer, including preventing or reducing metastases, drug resistance and recurrence of cancer.

Further, based on the examples of the present disclosure, a therapeutic method for treating or reducing the occurrence of cancer has been developed. The treatment is based on the discovery of a novel peptide that inhibits and/or silences BRCA1-IRIS. The BRCA1-IRIS molecule is overproduced in breast, ovarian and other cancerous cells and leads to the development of aggressive and a deadly form of these cancers. Yet, in some embodiments, the novel inhibitory peptide to BRCA1-IRIS (hereinafter "IRIS peptide") suppresses ovarian tumor growth, anoikis resistance, and it sensitizes ovarian cancer cells to lower concentration of platinum. In some embodiments, the IRIS peptide promotes cell death in BRCA1-IRIS overexpressing cells. In some embodiments, the IRIS peptide sensitizes TNBCs to low paclitaxel concentrations and/or reduces tumor growth.

The present-disclosure further provides that in some embodiments the IRIS peptide silences and/or inactivates the NRG1/ErbB2 loop, the BDNF/TrkB loop, the EGF/EGFR-ErbB2 and/or the NRG1/ErbB2-ErbB3 loop, or a combination thereof. Indeed, each of these autocrine signaling loops is enhanced and/or activated by BRCA1-IRIS overexpression.

In some embodiments, the therapeutic method(s) of the present disclosure targets BRCA1-IRIS with various agents, such as chemotherapeutic drugs, antibodies or other agents targeting BRCA1-IRIS to treat aggressive, metastatic, drug-resistant, and/or recurrent breast, ovarian and/or other cancers. Moreover, the subject matter of the present disclosure is based, at least in part, on targeting BRCA1-IRIS to treat cancer. BRCA1-IRIS targeting may be used as either a stand-alone therapeutic approach or as an adjunctive therapy to sensitize cancer cells to a chemotherapeutic agent. An advantage of BRCA1-IRIS-targeted therapeutic approaches is that they are directed at tumorigenic cells.

Accordingly, in some embodiments, the present disclosure provides a method for treating a subject, the method comprising administering to the subject a composition comprising an active agent, such as a peptide comprising the sequence set forth in SEQ ID NO: 1, and a chemotherapeutic agent. The chemotherapeutic agent may be any chemotherapy drug known in the art, such as, for example, cisplatin and/or paclitaxel.

In some embodiments, the present disclosure provides a method for treating cancer, wherein the method includes inhibiting BRCA-IRIS expression and/or activity. In certain embodiments, BRCA1-IRIS is silenced with specific shRNA and/or with a specific siRNA. In certain embodiments, methods of treating cancer, in accord with the present disclosure, include the steps of (i) silencing BRCA1-IRIS expression in a subject via administration of specific shRNA and/or siRNA and/or (ii) inhibiting BRCA-IRIS expression in a subject via administration of IRIS peptide, particularly wherein, in certain embodiments, the IRIS peptide comprises the sequence set forth in SEQ ID NO: 1 and/or SEQ ID NO: 2.

Indeed, in various embodiments, the method(s) of the present disclosure uses an inhibitor, which is siRNA and/or shRNA, which binds to BRCA1-IRIS mRNA to thereby reduce the amount of BRCA1-IRIS protein produced by cancer cells. In one advantageous form of the method, administering siRNA induces BRCA1-IRIS mRNA degradation when introduced to cancerous cells expressing normal or high levels of BRCA1-IRIS mRNA.

In some embodiments, the siRNA converts tumor cells into less-transformed cells or kills the cells. In one advantageous form, the siRNA sequence can be placed in a viral siRNA vector to produce a gene therapy. The vector is introduced to cells in a subject, such as cancer or tumor cells, resulting in a transformation of the cancer cells to have reduced levels of BRCA1-IRIS expression, thereby reducing a burden of cancer and the possibility of metastasizing cancer.

Oncogene addiction is a concept describing that some tumors depend on continuous expression/activity of a single oncogene for their proliferation and survival (Torti and Trusolino, 2011; McCormick, 2011; Felsher, 2008). So far, no predominant pathway ("addicting" oncogene) has been shown in ovarian tumors. Although one potential such oncogene has been described by Sheng and colleagues (2010). Further, several drug modalities have been developed to target ErbB3; however, the utility of these modalities remains to be clinically established. Moreover, it has been shown that the oncogene BRCA1-IRIS (ElShamy and Livingston, 2004) is overexpressed in the majority of ovarian cancer cell lines and that its overexpression induces overexpression of survivin (Chock et al., 2010b). Survivin functions to inhibit apoptosis, promote proliferation, and enhance invasion, and its elevated expression correlates with poor outcome(s) and treatment resistance in ovarian cancers (Chen et al., 2013). BRCA1-IRIS upregulates survivin expression by activating AKT, which phosphorylates and inactivates FOXO3a the upstream suppressor of survivin, or by suppressing PTEN expression (Liu et al., 1998; Page et al., 2000; Chock et al., 2010b; Monsalve and Olmos, 2011; Santo et al., 2013) The present disclosure describes the role(s) of BRCA1-IRIS in ovarian tumorigenesis, metastasis and drug resistant recurrences. Indeed, the present disclosure provides that BRCA1-IRIS overexpression in normal human ovarian surface epithelial (HOSE) cells upregulates expression of the neurotrophic factor tyrosine kinase B receptor (TrkB) and ErbB2 and their ligands, brain-derived neurotrophic factor (BDNF) and neuroglin 1 (NRG1, when ErbB2 is in complex with ErbB3), respectively. ErbB family members' role in ovarian cancer (as well as other cancers) is well documented (Tanner et al., 2006; Engelman et al., 2007; Sergina et al., 2007; Lafky et al., 2008; Blank et al., 2010; Chandarlapaty et al., 2011; Makhija et al., 2010; Sheng et al., 2010; Siwak et al., 2010). TrkB exists mostly in the nervous system and plays an essential role in the development and function of the nervous system, including regulation of cell survival and differentiation (Masana et al., 1993; Birling and Price, 1995; Alcántara et al., 1997).

TrkB is frequently overexpressed in a variety of human malignant tumors, including epithelial ovarian cancer (Yu et al., 2008; Zheng et al., 2011; Okamura et al., 2012; Hondermarck, 2012), where it mediates more aggressive behavior, resistance to chemotherapy, and poor prognosis (Huang et al., 2010; Ricci et al., 2010; Yu et al., 2010; Kupferman et al., 2010), in part by promoting anoikis resistance (Geiger and Peeper, 2007; Smit et al., 2009; Smit and Peeper, 2011). Thus, because ovarian cancer is a semi-solid cancer, suppression of anoikis, especially in the early stages of the disease is important to overcome the physiological barrier to metastasis (Geiger and Peeper, 2007; Smit et al., 2009; Smit and Peeper, 2011).

The present disclosure provides data showing that BRCA1-IRIS, in addition to promoting ovarian cancer proliferation and survival (ElShamy and Livingston, 2004; Nakuci et al. 2006; Hao and ElShamy, 2007; Chock et al., 2010a), helps dislodged tumor cells to survive in the ascites by suppressing anoikis. Further, anoikis is suppressed by inducing the autocrine loop "BDNF/TrkB". While not wishing to be bound by theory, it is suggested that this loop in combination with the other autocrine loop "NRG1/ErB2," which is also induced by BRCA1-IRIS, helps to establish distant ovarian metastasis.

Accordingly, in some embodiments, the present disclosure provides a novel inhibitory peptide to BRCA1-IRIS, which suppresses tumor growth, anoikis resistance and sensitizes cancer cells to low concentrations of platinum in vitro and in vivo.

Moreover, the present disclosure provides that inhibiting BRCA1-IRIS expression and/or activity is effective in killing tumor cells in vitro and in vivo, as shown with the xenografts described herein. Further, inhibiting BRCA-IRIS expression with the IRIS peptide also sensitizes cancer cells in vitro and tumors in vivo to lower concentration(s) of chemotherapeutic agents, such as cisplatin, indicating that BRCA1-IRIS inactivation is a sensitizer for cisplatin directed chemotherapy.

Figure 65:
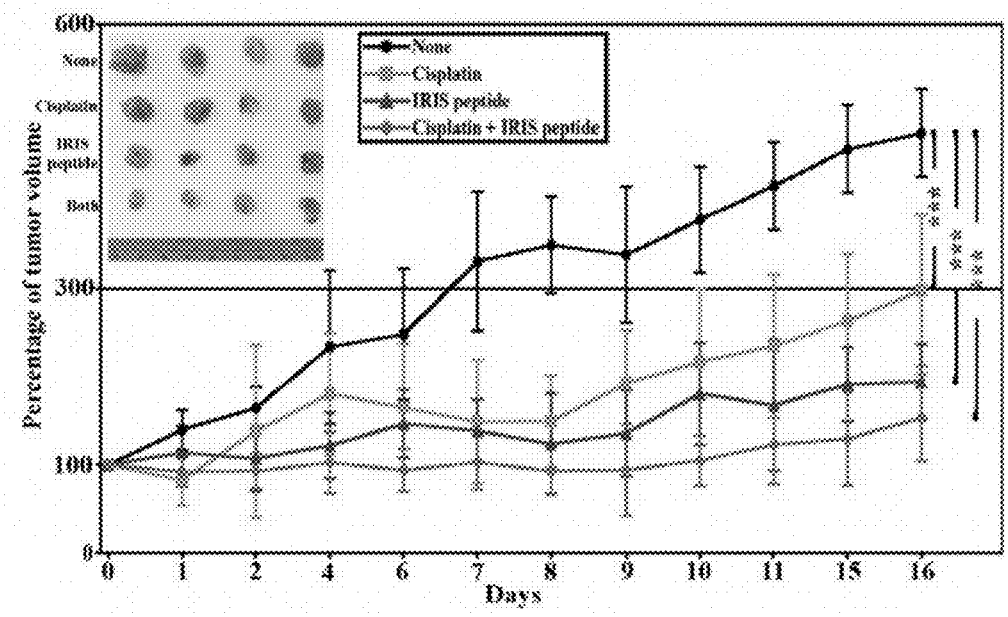
FIG. 65 presents, in the inset, tumors formed in SCID mice that were divided into four groups that were treated with: 1) control DMSO (i.p.) and scrambled peptide (i.t.), 2) treated with cisplatin (5 mg/kg, i.p.), 3) IRIS peptide (10 mg/kg, i.t.) or (4) both through the same routes. Further.
Figure 66:
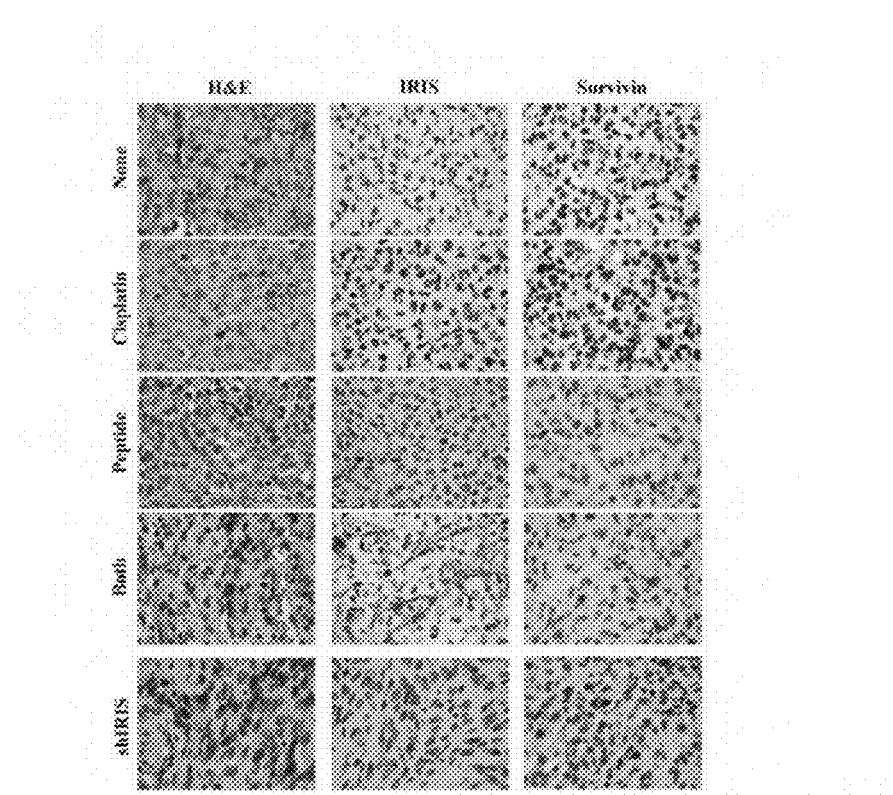
FIG. 66 shows immunohistochemical staining of samples from tumors stained with hematoxylin and eosin (left column), BRCA1-IRIS (middle column) and survivin antibody (right column). The last row shows the same in tumors formed using SKOV3 cells expressing BRCA1-IRIS shRNA.

Indeed, BRCA1-IRIS inactivation with the IRIS peptide is accompanied by a significant reduction in AKT activation and Cyclin D1, survivin, Bcl-2 and NF-κB expression, all of which are known targets of BRCA1-IRIS overexpression. Thus, residual tumors that remain after inhibiting BRCA1-IRIS, either alone or in combination with cisplatin, are BRCA1-IRIS- and survivin-negative (FIG. 65, FIG. 66).

Another interesting aspect of the present disclosure is that unlike the in vitro effect(s), in which BRCA1-IRIS overexpression is correlated with AKT activation leading to FOXO3a degradation and thus survivin overexpression (Weng et al., 2009; Zhang et al., 2009; Chock et al., 2010b; Jiang et al., 2013), in human tumors it is observed that FOXO3a was still expressed even though BRCA1-IRIS and survivin were overexpressed. Yet, notably, the localization of FOXO3a in these tumors is restricted to the cytoplasm. Thus, it is possible that in vivo, FOXO3a is fundamentally important for tumor growth and instead of shutting down the FOXO3a gene, tumors opt, instead, to restrict its nuclear localization, at least under certain circumstances. Another possibility is that in vivo BRCA1-IRIS restricts FOXO3a access to the nucleus, without affecting its expression and/or stability.

Overexpression of BRCA1-IRIS enhances secretion of large quantities of BDNF and NRG1 from ovarian epithelial cells and, at the same time, upregulates expression of the TrkB and ErbB2 receptors. These two autocrine loops; BDNF/TrkB (Masana et al. 1993; Alcantara et al., 1997; Jungbluth et al., 1997) and NRG1/ErbB2-ErbB3 could be responsible for BRCA1-IRIS-induced ovarian cancer drug resistance and metastasis, either separately or through mutual crosstalk. Crosstalk between heterologous cellular signaling systems is common and does highlight the fact that a net biological response is more often the result of functional integration of diverse signaling networks (Puehringer et al., 2013; Yue et al., 2013). Accordingly, in some embodiments, the present disclosure provides a method for downregulating expression of BDNF and/or NRG1 in a subject via the administration of IRIS peptide and/or specific shRNA to inhibit and/or silence BRCA1-IRIS expression in the subject.

The BDNF/TrkB signaling loop, best known for its role in promoting proliferation, differentiation and survival in the nervous system, has gained great attention for its anoikis suppressor role. Indeed, BRCA1-IRIS has been shown earlier to enhance replication and proliferation in breast and ovarian cancer cells (ElShamy and Livingston, 2004; Nakuci et al., 2006; Hao and ElShamy, 2007).

The data presented herein show that BRCA1-IRIS overexpression by upregulating BDNF/TrkB protects against anoikis (FIG. 55-59). Further, it is proposed that BRCA1-IRIS overexpression is also involved in protecting ovarian tumor cells dislodged from the ovary against anoikis when they are present in the ascites (Douma et al., 2004; Geiger and Peeper, 2007; Smit et al., 2009; Ween et al., 2011). Adding support to the proposal is the increased expression of several survival pathways, including survivin, Bcl-2, Bcl-xL and c-IAP-2 in BRCA1-IRIS overexpressing cells (Wendel et al., 2004).

Moreover, enhancement of ErbB2 and its ligand, NRG1 (when in complex with ErbB3) by BRCA1-IRIS overexpression further suggests that cancer cells that moved out from the ovary to the peritoneal have also acquired metastatic ability (Blank et al., 2010; Gordon et al., 2006; Ricci et al., 2010; Sheng et al., 2010; Yu et al., 2008), in part through activating PI3K/AKT pathway, which also is activated by BDNF/TrkB signaling loop. PI3K/AKT signaling drives numerous other cellular functions associated with metastasis, such as lamellipodia formation (key aspect of tissue invasion) and angiogenesis within tumors when oxygen level is low (Wendel et al., 2004; Brader and Eccles, 2004).

BRCA1-IRIS seems to fit the criteria for being an addictive oncogene. Its overexpression induces the full repertoire of ovarian cancer, from initiation to metastasis, and its inactivation inhibits the full spectrum of the disease. In a semisolid cancer, such as ovarian cancer, it seems important that an addictive oncogene enhances the ability of cells to survive independently of attachment to the matrix or to other cells (anoikis, Kim et al., 2004; Douma et al., 2004), and BRCA1-IRIS overexpression by promoting an auto-stimulatory signaling loop "BDNF/TrkB" seems to do that.

Figure 32:
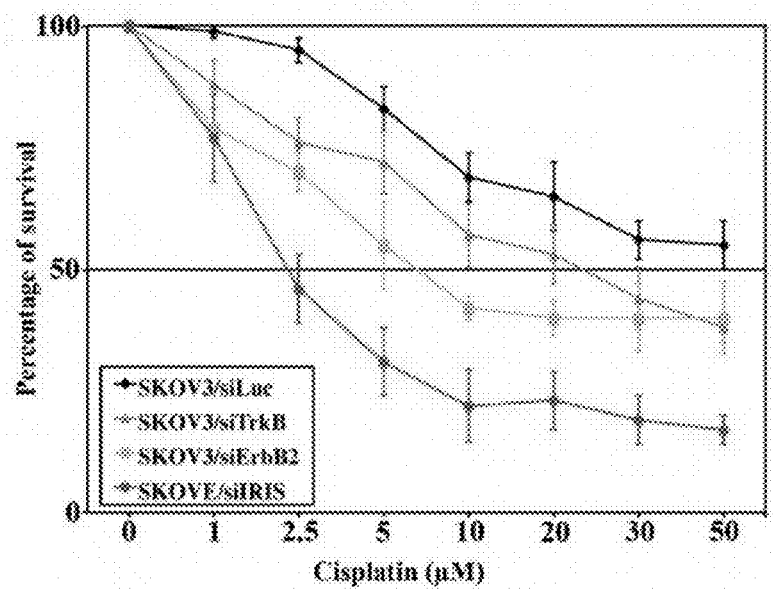
FIG. 32 illustrates the effect of BRCA1-IRIS silencing using a specific siRNA as compared to silencing of ErbB2 and TrkB on the survival of SKOV3 cells. The effect of each siRNA on its cognate protein is shown in the panels on the right.
Figure 33:
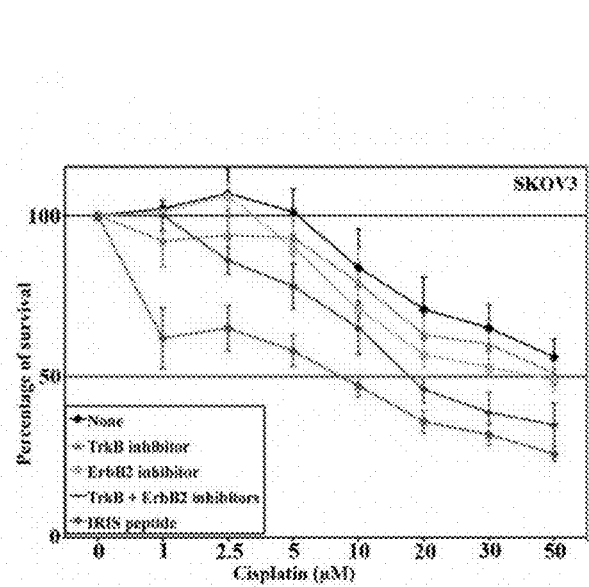
FIG. 33 shows the effect of IRIS peptide on the survival of SKOV3 cells as compared to the effects of ErbB2, TrkB inhibitors alone or in combination.

From the data presented in FIG. 32 and FIG. 33, it appears that while BRCA1-IRIS silencing or inactivation seems to sensitize ovarian cancer cells to cisplatin by inactivating the autocrine signaling loops, BDNF/TrkB and NRG1/ErbB2, in parallel. Indeed, only when both loops are inhibited simultaneously, BRCA1-IRIS overexpressing cells show a pattern similar to BRCA1-IRIS inactivated cells. However, this was observed herein only in cells treated with high concentrations of cisplatin. It is possible that at low cisplatin concentrations, BRCA1-IRIS inactivation was far superior to that observed following TrkB plus ErbB2 inactivation, suggesting that BRCA1-IRIS overexpression upregulates additional signaling loops involved in its ability to resist death by low concentrations of cisplatin.

In some embodiments, present disclosure provides a method for inactivating autocrine loops in a subject. The method includes at least the step of administering IRIS peptide and/or specific shRNA to inhibit and/or silence BRCA1-IRIS expression to the subject.

As noted above, the term "active agent" is used herein to refer to compounds or entities that alter, promote, speed, prolong, inhibit, activate, eliminate, or otherwise affect biological or chemical events in a subject. Still further, some embodiments of the compounds of the present disclosure can further comprise a second active agent, a third active agent, and so forth.

Active agents of the present disclosure also include, but are not limited to, enzymes, organic catalysts, ribozymes, organometallics, proteins, glycoproteins, peptides, polyamino acids, antibodies, nucleic acids, steroidal molecules, antibiotics, antivirals, antimycotics, anticancer agents, analgesic agents, antirejection agents, immunosuppressants, cytokines, carbohydrates, oleophobics, lipids, extracellular matrix and/or its individual components, demineralized bone matrix, pharmaceuticals, chemotherapeutics, cells, viruses, virus vectors, and prions.

The presently-disclosed subject matter further includes pharmaceutical compositions comprising compounds as disclosed herein. In some embodiments, the present disclosure provides a pharmaceutical composition comprising any peptide of the present disclosure, such as IRIS peptides. In certain embodiments, the pharmaceutical composition of the present disclosure comprises a peptide comprising the amino acid sequence set forth in SEQ ID NO: 1. In some embodiments, the present disclosure provides a pharmaceutical composition comprising an isolated peptide that is an active agent.

In further embodiments, a pharmaceutical composition of the present disclosure comprises (i) a first peptide comprising the amino acid sequence set forth in SEQ ID NO: 1 and (ii) a second peptide comprising the amino acid sequence set forth in SEQ ID NO: 2. In still further embodiments, the present disclosure provides a pharmaceutical composition comprising a fusion peptide, wherein the fusion peptide comprises an active agent, such as a peptide comprising the sequence set forth in SEQ ID NO: 1, and/or a cell-penetrating peptide, such as a peptide comprising the sequence set forth in SEQ ID NO: 2.

Such pharmaceutical compositions may comprise at least one pharmaceutically-acceptable carrier. In this regard, the term "pharmaceutically acceptable carrier" refers to sterile aqueous or non-aqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

The presently-disclosed subject matter further includes a kit that can include a compound or pharmaceutical composition as described herein, packaged together with a device useful for administration of the compound or composition. As will be recognized by those or ordinary skill in the art, the appropriate administration-aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

The term "administering" refers to any method of providing a compound and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition (e.g., cancer, tumors, etc.). In further various aspects, a preparation can be administered prophylactically; that is, administered for prevention of a disease or condition.

As also noted above, in some embodiments, a subject will be administered an effective amount of the compound, which refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

In some embodiments, the subject will be suffering or will have been diagnosed with one or more neoplastic or hyperproliferative diseases, disorders, pathologies, or conditions. Thus, an administration site to be exposed in a subject may be in close proximity or at the location of such a disease, condition, etc. (e.g., tumor). Examples of such diseases, conditions, and the like include, but are not limited to, neoplasms (cancers or tumors) located in the colon, abdomen, bone, breast, digestive system, esophagus, liver, pancreas, peritoneum, endocrine glands (adrenal, parathyroid, pituitary, testicles, ovaries, cervix, thymus, thyroid), eye, head and neck, nervous (central and peripheral), lymphatic system, pelvis, skin, soft tissue, spleen, thoracic areas, bladder, and urogenital system. Other cancers include follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer, or metastases thereof.

A subject may also be in need because (s)he has acquired diseases or conditions associated with abnormal and increased cell survival such as, but not limited to, progression and/or metastases of malignancies and related disorders such as leukemia (including acute leukemias (e.g., acute lymphocytic leukemia, acute myelocytic leukemia, including myeloblastic, promyelocytic, myelomonocytic, monocytic, and erythroleukemia) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. The conditions, diseases, and the like described above, as well as those that will be apparent to those of ordinary skill in the art, are collectively referred to as "cancer" herein.

EXAMPLES

The presently-disclosed subject matter is further illustrated by the following specific but non-limiting examples. The examples may include compilations of data that are representative of data gathered at various times during the course of development and experimentation related to the presently-disclosed subject matter.

Ovarian Cancer Related Examples

The example experiments described herein were conducted, in relevant part, to determine whether BRCA1-IRIS is a treatment target for ovarian cancers and the platinum-resistant recurrences of those cancers.

More than half of ovarian cancer samples analyzed show BRCA1-IRIS and survivin overexpression and lack nuclear FOXO3a expression. Normal ovarian epithelial cells overexpressing BRCA1-IRIS formed colon metastasis in mice when injected in the peritoneal cavity. Two autocrine signaling loops; NRG1/ErbB2 and BDNF/TrkB were induced by BRCA1-IRIS and operate to promote anoikis resistance and ovarian cancer progression. Suppressing BRCA1-IRIS expression or activity prevented expression of these loops, promoted cell death, ovarian tumor regression and sensitized tumors to low cisplatin concentrations.

Here it is reported that BRCA1-IRIS activates two autocrine signaling loops, BDNF/TrkB and NRG1/ErbB2, known to promote ovarian cancer progression. These loops are present in several ovarian cancer cell lines, and BRCA1-IRIS silencing or inactivation using a novel inhibitory peptide renders both non-functional. In a mouse xenograft model, inhibiting BRCA1-IRIS expression using a specific shRNA or activity using this novel inhibitory peptide resulted in significant reduction in ovarian tumor growth. More importantly, this peptide sensitized ovarian tumors to low cisplatin concentrations. Taken together, these data strongly suggest that BRCA1-IRIS and/or BDNF/TrkB and NRG1/ErbB2 could serve as rational targets for advanced ovarian cancers.

Example 1

Elevated BRCA1-IRIS and Survivin Expression and Lack of Nuclear FOXO3a in Ovarian Tumors.

High BRCA1-IRIS expression has been observed in ovarian cancer cell lines (Chock et al., 2010b). To evaluate the expression in human tumors, 30 normal ovarian samples, 184 ovarian adenocarcinoma samples and 67 ovarian metastasis samples were immunohistochemically (IHC) stained with a monoclonal antibody against BRCA1-IRIS. Normal ovarian surface epithelial cells showed very low levels of BRCA1-IRIS, ovarian adenocarcinoma showed more pronounced expression that increased concordantly with tumor grade, and metastatic tissues showed the highest levels of BRCA1-IRIS (FIG. 1, FIG. 2, FIG. 3, and FIG. 4).

The same tissue microarrays were also IHC stained for survivin and FOXO3a. Like with BRCA1-IRIS expression, normal ovarian surface epithelial cells showed very low expression, ovarian adenocarcinoma(s) showed more pronounced expression, and metastatic tissues showed the highest expression (FIG. 5, FIG. 6, FIG. 7, and FIG. 8).

In contrast, relatively high expression level of FOXO3a was detected in normal ovarian tissues that remained high but more confined to the cytoplasm in adenocarcinoma and metastatic tissues (FIG. 9, FIG. 10). Taken together these data show that BRCA1-IRIS expression is concordantly high in ovarian cancer tissues with survivin and with cytoplasmic, not nuclear, FOXO3a.

Example 2

BDNF/TrkB and NRG1/ErbB2 Autocrine Signaling Loops Induced by BRCA1-IRIS Overexpression Regulate Ovarian Cancer Cell Survival.

Ovarian cancer is a semi-solid cancer, meaning that in the early stages, cancer cells disseminate from the ovary, move into the peritoneal lining of the lower abdomen, and live in ascetic fluid before metastasizing into organs, such as the colon. To be able to survive this journey, these cells must suppress anoikis To explain the contribution of BRCA1-IRIS overexpression to anoikis resistance, factors secreted from normal human ovarian surface epithelial (HOSE) cells or HOSE cells overexpressing BRCA1-IRIS (hereafter HOSE/IRIS) were compared on ligand antibody arrays.

Figure 12:
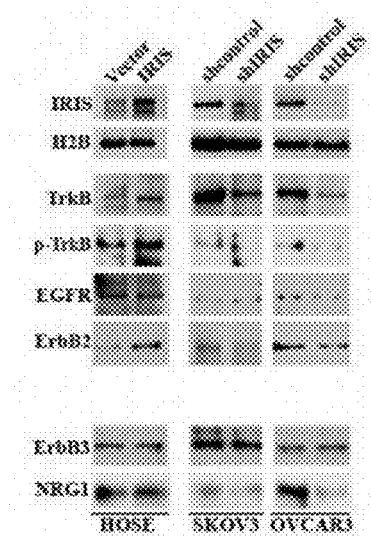

TrkB ligand; BDNF (Douma et al., 2004; Geiger and Peeper, 2007; Yu et al., 2008) is secreted at significantly higher level from HOSE/IRIS cells compared to HOSE cells (see arrow in FIG. 11). HOSE/IRIS cells also showed high expression levels of TrkB and p-TrkB (Y515) compared to HOSE cells (FIG. 12). BRCA1-IRIS silencing significantly in two ovarian cancer cell lines overexpressing BRCA1-IRIS and TrkB (FIG. 12) decreased the expression of TrkB and p-TrkB (FIG. 12).

The HER family members (HER1-4) are also involved in ovarian tumor cell survival and metastases (Yarden, 2001; Tanner et al., 2006; Engelman et al., 2007; Sergina et al., 2007; Lafky et al., 2008; Blank et al., 2010). BRCA1-IRIS overexpression in HOSE cells upregulated the expression of ErbB2 but not EGFR or ErbB3 (FIG. 12). BRCA1-IRIS silencing in SKOV3 and OVCAR3 cells downregulated ErbB2 expression only (FIG. 12). Moreover, NRG1 not EGF was upregulated by BRCA1-IRIS overexpression in HOSE cells and downregulated by BRCA1-IRIS silencing in SKOV3 and OVCAR3 cells (FIG. 12). These data show that BRCA1-IRIS overexpression enhances TrkB expression and activation, and ErbB2 expression and ErbB2/ErbB3 and not ErbB2/EGFR activation.

Figure 13:
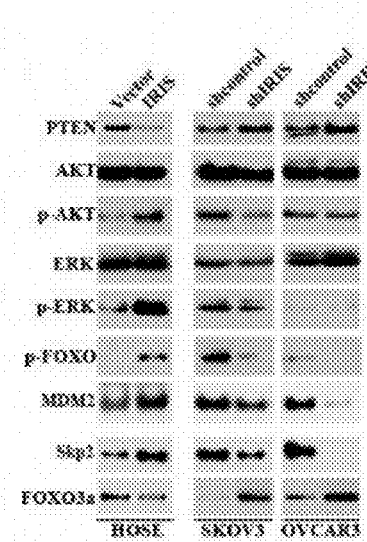

As expected, downstream targets of TrkB and ErbB2, such as AKT and ERK were also activated in HOSE/IRIS cells and inactivated in BRCA1-IRIS silenced SKOV3 and OVCAR3 cells (FIG. 13 shows p-T308/5473-AKT and p-T202/Y204-ERK). PTEN that inactivates AKT expression was decreased by BRCA1-IRIS overexpression in HOSE cells, and increased by BRCA1-IRIS silencing in SKOV3 and OVCAR3 (See FIG. 13).

Figure 14:
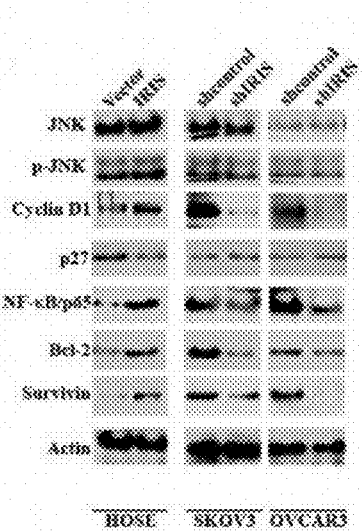
Figure 15:
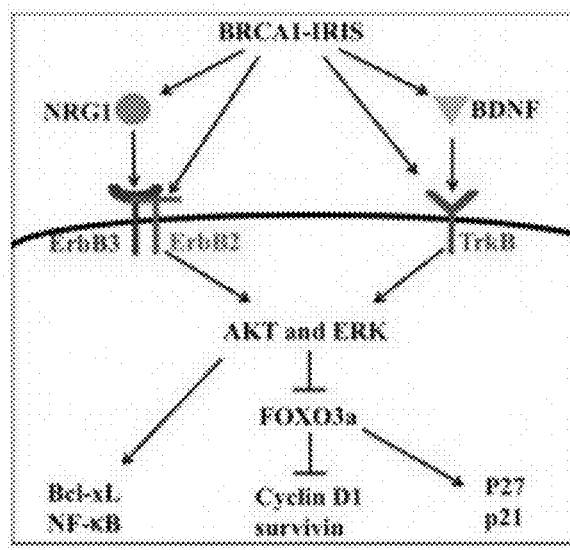

Phosphorylation of FOXO3a by activated AKT (on T32/5253) or ERK (S294/344/425, Yang JY et al., 2008) enhances its proteasomal degradation by MDM2 and/or Skp2 (Huang and Tindall, 2011; Monsalve and Olmos, 2011). Consistently, HOSE/IRIS contained high levels of p-FOXO and low levels of total FOXO3a, and BRCA1-IRIS silenced SKOV3 and OVCAR3 cells contained low levels of p-FOXO and high levels of total FOXO3a (FIG. 2B, middle panels). Moreover, expression of MDM2 and Skp2 increased in BRCA1-IRIS overexpressing HOSE cells and decreased in BRCA1-IRIS silenced SKOV3 and OVCAR3 cells (FIG. 13). Moreover, proteins inhibited by FOXO3a, such as Cyclin D1, survivin, Bcl-2 and NF-κB/p65 were all upregulated by BRCA1-IRIS overexpression in HOSE cells and downregulated by BRCA1-IRIS silencing in SKOV3 and OVCAR3 cells (FIG. 14), whereas those induced by FOXO3a, such as p27 were downregulated by BRCA1-IRIS overexpression in HOSE cells and upregulated by BRCA1-IRIS silencing in SKOV3 and OVCAR3 cells (FIG. 12). A schematic representation of these data is shown in FIG. 15.

Figure 16:
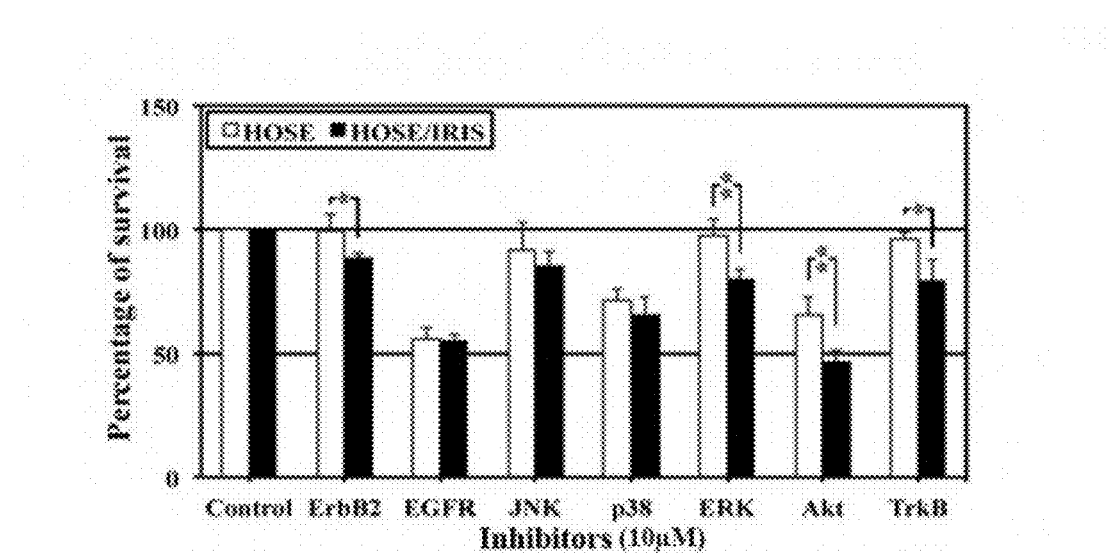

The data suggest that BRCA1-IRIS overexpressing cells might be more sensitive to inhibition of ErbB2, TrkB, AKT or ERK. To test that, HOSE or HOSE/IRIS cells were incubated for 24 hours with 10 µM of ErbB2 (CP-724714), EGFR (Erlotinib), TrkB (K252a), JNK (SP600125), p38 (SB203580), ERK (PD98059) and PI3'K/AKT (LY294002) inhibitors. JNK inhibitor had no effect on either cell line, and EGFR and p38 inhibitors equally decreased survival of HOSE and HOSE/IRIS cells. In contrast, ErbB2, TrkB, ERK and PI3'K/AKT inhibitors significantly decreased survival of HOSE/IRIS cells only (FIG. 16). Taken together, BRCA1-IRIS overexpression activates AKT and ERK, thereby inactivating FOXO3a and promoting Cyclin D1, survivin, Bcl-2 and NF-κB expression and suppressing p27 expression (FIG. 15).

Example 3

At Low Concentrations, Cisplatin Induces BRCA1-IRIS Expression.

About 20% of ovarian cancer patients suffer from intrinsic resistance to first-line treatment cisplatin-based chemotherapy. Although the other 80% initially respond, the majority of those eventually develop acquired cisplatin resistance. It has been shown that ovarian cancer cells overexpressing BRCA1-IRIS are cisplatin resistant (intrinsic, Chock et al., 2010b) and that at low concentrations, cisplatin upregulated BRCA1-IRIS expression in normal, as well as in low expressing ovarian cancer cells, leads to drug resistance (acquired, Chock et al., 2010b).

To investigate the mechanism that BRCA1-IRIS overexpression utilizes to promote intrinsic and/or acquired cisplatin resistance in ovarian cancer cells, HOSE cells were used to study acquired resistance, and HOSE/IRIS cells were used to study intrinsic resistance.

Figure 17:
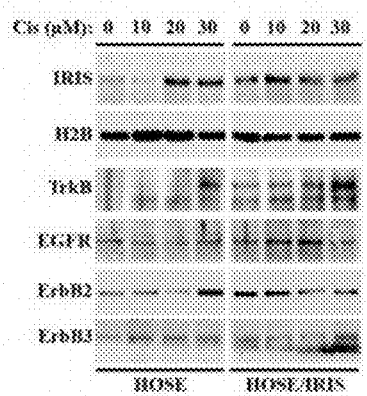

Both cell lines were exposed to 0, 10, 20 or 30 µM of cisplatin for 24 hours, followed by Western analysis. At these low concentrations of cisplatin BRCA1-IRIS expression was induced in HOSE cells and remained high in HOSE/IRIS cells (FIG. 17). TrkB and ErbB2 (not EGFR or ErbB3) both were also induced by cisplatin in HOSE cells and remained high in HOSE/IRIS cells (FIG. 17).

Figure 18:
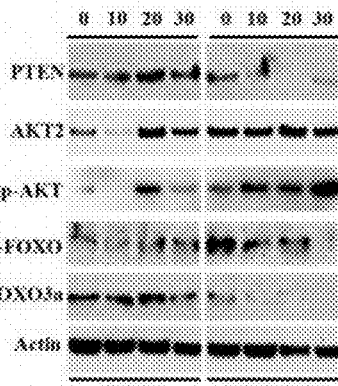
Figure 19:
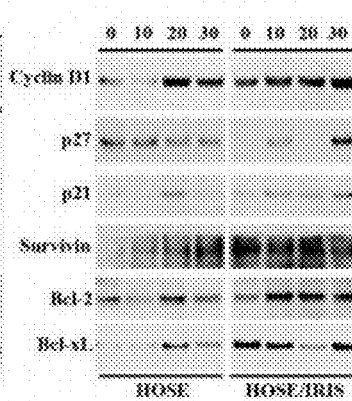

Although PTEN expression remained unchanged in HOSE cells following cisplatin treatment, AKT2 expression and phosphorylation increased (FIG. 18), perhaps suggesting over-activation of PI3'K. In contrast, cisplatin treatment significantly decreased PTEN expression in HOSE/IRIS and hence increased AKT phosphorylation (FIG. 18). Accordingly, p-FOXO levels increased in HOSE and HOSE/IRIS cells, which led to dramatic decrease in total FOXO3a in both cell lines (FIG. 18). FOXO3a targets, Cyclin D1, survivin, Bcl-2 and Bcl-xL were all induced, while cell cycle inhibitors, p27 and p21 were suppressed by cisplatin in both cell lines (FIG. 19).

Figures 20, 21:
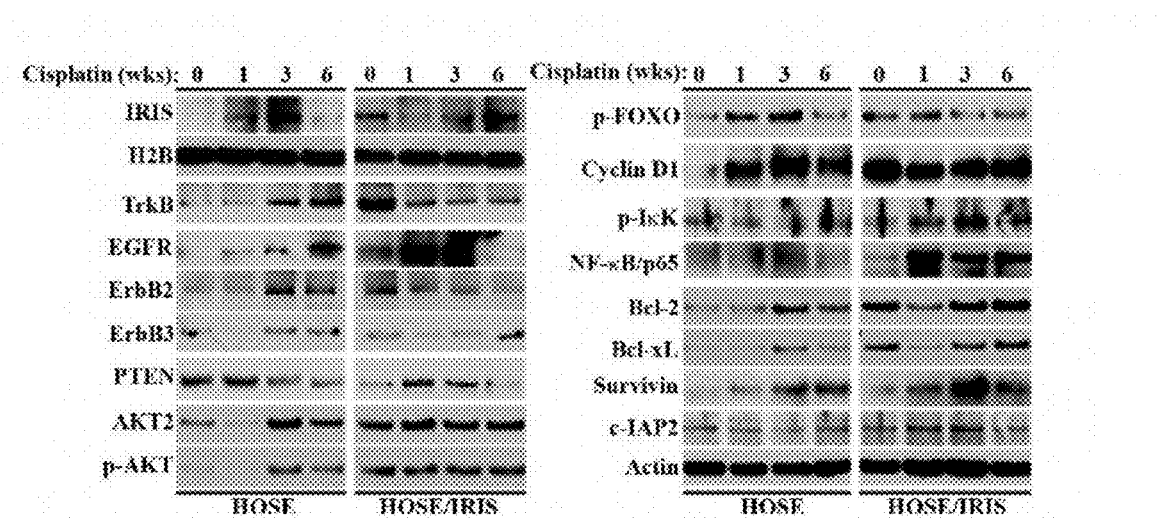
FIG. 20 shows the expression of BRCA1-IRIS and the indicated proteins, IRIS, H2b, TrkB, EGFR, ErbB2, ErbB3, PTEN, AKT2, and p-AKT in HOSE or HOSE/IRIS cells following exposure to 1 µM of cisplatin for 1, 3 or 6 weeks.
FIG. 21 shows the expression of BRCA1-IRIS and the indicated proteins, p-FOXO, Cyclin D1, P-IκK, NF-κB/p65, Bcl-2, Bcl-xL, survivin, c-IAP2 and Actin, in HOSE or HOSE/IRIS cells following exposure to 1 µM of cisplatin for 1, 3 or 6 weeks.

To study that directly, cisplatin-resistant HOSE and HOSE/IRIS cells were developed by growing cells in 10 µM of cisplatin for 1, 3 or 6 weeks. In HOSE cells, the resistant cells showed increase BRCA1-IRIS (although at week 6 a sharp decrease in this upregulation was noticed) that was accompanied by an increase in TrkB, ErbB2 and, surprisingly, EGFR and ErbB3 starting at week 1 (FIG. 20). These cells also showed diminished PTEN expression especially at later time points, which led to a corresponding increase in total and phosphorylated AKT2 (FIG. 20) as well as increase in p-FOXO (FIG. 21).

Figure 22:
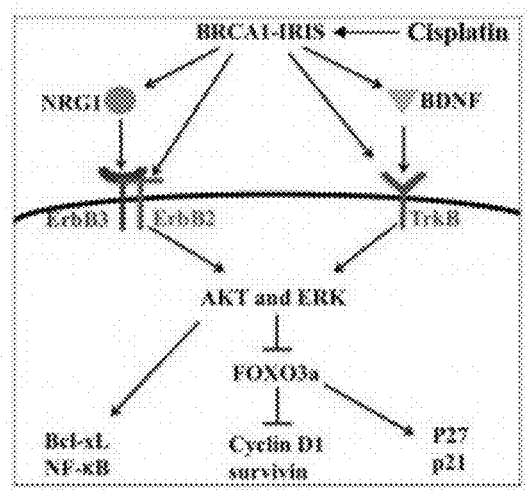
FIG. 22 is a schematic summary of the entire data presented in FIGS. 16-19.

Consistently, increase in the expression of FOXO3a suppression targets; Cyclin D1, NF-κB, Bcl-2, Bcl-xL, c-IAP2 and survivin was also documented (FIG. 21). In HOSE/IRIS cells, the levels were high and remained high throughout the experiment(s). Taken together, these data confirm that at low concentrations, cisplatin could induce its own resistance by upregulating BRCA1-IRIS, which in turn upregulates a plethora of growth and survival proteins. A schematic representation of the data is shown in FIG. 22.

Example 4

Development of BRCA1-IRIS Inhibitory Peptide.

The above data suggest that inhibiting BRCA1-IRIS expression and/or activity could sensitize ovarian cancer cells to low concentration of cisplatin. To study this, BRCA1-IRIS was silenced in SKOV3 and OVCAR3 with specific shRNA. Depleted cells were then exposed to increasing concentrations of cisplatin, and survival was measured by cell counting. As expected, compared to control shRNA-expressing cells, BRCA1-IRIS depleted cells (hereafter, shIRIS, see FIG. 23) were much more sensitive to cisplatin (FIG. 23, FIG. 24).

While overexpression of a wild-type BRCA1-IRIS induced expression of Cyclin D1, survivin and vimentin in HOSE cells (FIG. 25), overexpression of an intron-less BRCA1-IRIS (missing the 34 amino acid encoded by the intron 11 sequence) did not (FIG. 25). This suggests that most of BRCA1-IRIS oncogenic functions reside in the intron portion. However, the intron portion is a small domain that holds no significant structural similarity (or perhaps function) to any known functional domains in protein databases. Accordingly, it is suggested instead that BRCA1-IRIS uses this intron 11 domain to interact with other proteins and that the complex is what holds the oncogenic functions known for BRCA1-IRIS (see ElShamy and Livingston, 2004; Nakuci et al., 2006, Hoa and ElShamy, 2007, Chock et al., 2010a and b). If true, it is possible that interrupting the formation of this complex(es), by, for example, a mimic peptide could inhibit BRCA1-IRIS oncogenecity, due to disruption of the formation of the complex(es), and perhaps sensitize ovarian cancer cells to chemotherapy.

Thus, a peptide (hereafter IRIS peptide) composed of a cell/nucleus penetrating signal (FIG. 26) fused to BRCA1-IRIS intron 11 (FIG. 26) was synthesized. Equal numbers of HOSE, HOSE/IRIS, SKOV3, OVCAR3, OVCAR420 and OV-90 cells were grown in the presence of increasing concentrations of IRIS peptide for 48 hours. Cell counting showed a gradual decrease in number of cells that survived after increasing the concentration of the peptide in all cell lines (FIG. 27). Cell lines expressing the lowest levels of BRCA1-IRIS (i.e. HOSE and OVCAR420, see inset in FIG. 27) showed the least $IC_{50}$ of ~1 μM (FIG. 3B), a cell line expressing medium level, e.g., OV-90 (see FIG. 27, inset) showed medium $IC_{50}$ of ~5 μM (FIG. 27), whereas cell lines expressing the highest levels (namely, HOSE/IRIS, SKOV3 and OVCAR3, see FIG. 27, inset) showed the highest $IC_{50}$ of ~10 μM (FIG. 27). Notably, the decrease in the survival in all cell lines was associated with significant reduction in BRCA1-IRIS expression in all cell lines (treated with 10 μM of IRIS peptide for 24 hours, see FIG. 27, inset). These data show that IRIS peptide indeed acts as a dominant negative that triggers BRCA1-IRIS degradation and ovarian cancer cell death, most likely by inhibiting the formation BRCA1-IRIS-X oncogenic complex(es).

To establish the specificity of this peptide further, it was assumed that it would not affect cells already depleted from BRCA1-IRIS. To do that HOSE, HOSE/IRIS, SKOV3, OVCAR3, OVAC420 and OV-90 cells were first transfected with luciferase (as control, hereafter siLuc) or BRCA1-IRIS (hereafter siIRIS) specific siRNAs for 48 hours before they were exposed to increasing concentrations of IRIS peptide for another 24 hours. In line with the data described above, a gradual decrease in the survival of all cell lines was observed in siLuc-transfected cells incubated with increasing concentrations of IRIS peptide (FIG. 28). In contrast, a 50% reduction in the survival of all cell lines was detected in BRCA1-IRIS silenced cells that was not affected by the peptide at any of the concentrations tested (FIG. 29). Taken together, this data supports the conclusion that this peptide specifically targets BRCA1-IRIS.

Example 5

An IRIS-Inactivating Peptide Sensitizes Ovarian Cancer Cells to Low Concentrations of Cisplatin.

Figure 30:
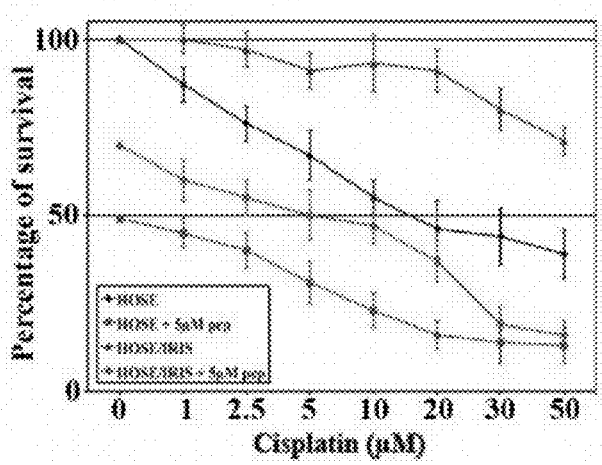
FIG. 30 illustrates the synergistic effect of cisplatin and IRIS peptide on the survival of HOSE versus HOSE/IRIS cells.
Figure 31:
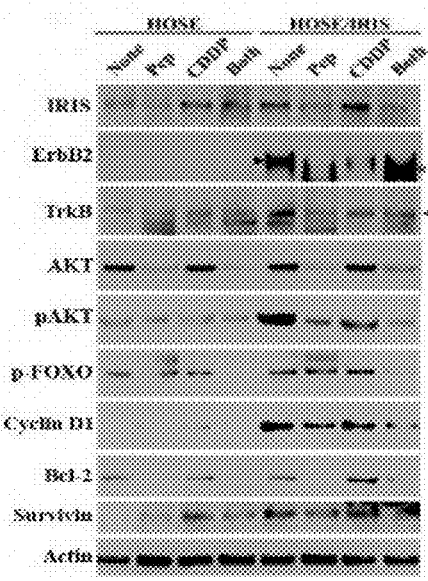
FIG. 31 shows the effect of cisplatin, IRIS peptide or the combination thereof on the expression of the indicated proteins: IRIS, ErbB2, TrkB, AKT, pAKT, p-FOXO, Cyclin D1, Bcl-1, Survivin, and Actin. Note, the arrowhead indicates ErbB2 position, the arrow indicates TrkB position, and the asterisk indicates a non-specific band position.

HOSE cells overexpressing IRIS show a higher degree of resistance to cisplatin than HOSE cells (compare blue to black line in FIG. 30). Pre-treatment with 5 μM of IRIS peptide decreased survival of HOSE and HOSE/IRIS cells (see green and red lines in FIG. 30), but it also sensitized HOSE and HOSE/IRIS cells to low concentrations of cisplatin (see red and green lines in FIG. 30). On the molecular level, 5 μM of IRIS peptide led to a significant decrease in BRCA1-IRIS, TrkB, ErbB2, AKT, p-AKT, p-FOXO, Cyclin D1, Bcl-2 and survivin expression in HOSE and HOSE/IRIS cells (see lane 2 and 5 in FIG. 3D, see also Chock et al., 2010b). In keeping with earlier data, treatment with 10 μM of cisplatin increased expression of BRCA1-IRIS and the other proteins in both cell lines (see lane 3 and 7 in FIG. 31 also see Chock et al., 2010b). Impressively, combining IRIS peptide at half the concentration (2.5 μM) with cisplatin, also at half the concentration (5 μM), completely abolished expression of BRCA1-IRIS and the other growth and survival proteins (see lane 4 and 8 in FIG. 31). These data clearly show that suppressing BRCA1-IRIS expression and/or activity could sensitize ovarian cancer cells to low concentration of cisplatin.

Example 6

BRCA1-IRIS Overexpression Promotes Cisplatin Resistance by Activating ErbB2 and TrkB.

To investigate the contribution of ErbB2 and TrkB to BRCA1-IRIS-induced cisplatin resistance, equal numbers of SKOV3 cells were either depleted from BRCA1-IRIS, ErbB2 or TrkB using specific siRNAs for 48 hours before they were (i) exposed to increasing concentrations of cisplatin for another 24 hours or (ii) exposed to IRIS peptide, ErbB2 inhibitor (CP-724714), TrkB inhibitor (K252a) or both for 24 hours, before they were exposed to increasing concentrations of cisplatin for another 24 hours.

Compared to siLuc transfected cells that were resistant to cisplatin ($IC_{50}$>50, see black lines in FIG. 3E), ErbB2 silencing (see middle panels in FIG. 32, right) or TrkB silencing (see lower panels in FIG. 32, right) sensitized cells to cisplatin with an $IC_{50}$~7.5 in siErbB2 transfected cells (green line in FIG. 32) and with an $IC_{50}$~20 in siTrkB transfected cells (purple lines in FIG. 3E). Impressively, BRCA1-IRIS silencing (see upper panels in FIG. 32, right) also sensitized cells to cisplatin. However, as would be expected from a protein upstream of both receptors (see FIG. 15 or FIG. 22) this led to an $IC_{50}$ of only ~2.5 (red line in FIG. 32).

Moreover, compared to vehicle treated SKOV3 cells (negative control) that showed $IC_{50}$>50 (black line in FIG. 33), inactivation of ErbB2 sensitized cells to cisplatin with an $IC_{50}$~30 (green line FIG. 33), inactivation of TrkB also sensitized cells to cisplatin with an $IC_{50}$~50 (purple line in FIG. 33), whereas inactivation of BRCA1-IRIS (using IRIS peptide) sensitized the cells even more to cisplatin with an $IC_{50}$ of ~7.5 (red line in FIG. 33). Taken together, these data suggest that BRCA1-IRIS overexpression induces cisplatin resistance by activating ErbB2 and TrkB in parallel. In fact, simultaneous inhibition of TrkB and ErbB2 synergistically reduced cisplatin resistance to a level similar to that observed with IRIS peptide, especially at high cisplatin concentrations (compare blue to red line in FIG. 33). It is perhaps possible that at lower cisplatin concentrations, BRCA1-IRIS induces additional pathways that promote cisplatin resistance (compare red to blue line in FIG. 33).

Figure 34:
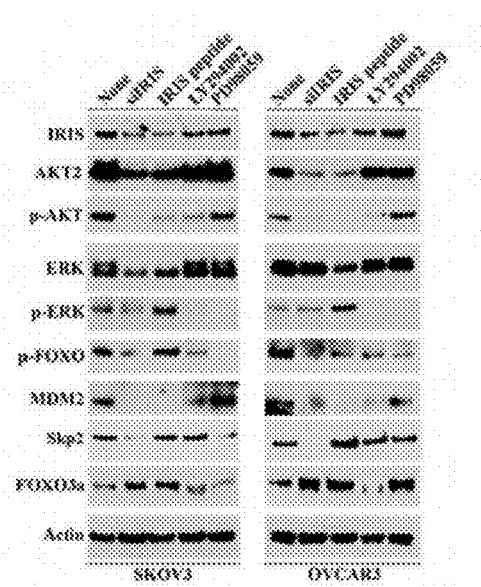
FIG. 34 shows the effect of BRCA1-IRIS siRNA or inhibitory peptide on the expression of the indicated proteins, IRIS, AKT2, p-AKT, ERK, p-ERK, p-FOXO, MDM2, Skp2, FOXO3a, and Actin, as compared to the PI3'K inhibitor, LY294002 and ERK inhibitor, PD98059.

Finally, to further dissect the IRIS-induced cisplatin resistance pathway, PI3'K/AKT (using LY2940002) and ERK (using PD98059) were inactivated and compared to IRIS peptide in two aggressive ovarian cancer cell lines. While LY2940002 and PD98059 had no effect on total AKT2 (or AKT1, not shown) and/or ERK respectively, they significantly inactivated their cognate protein in SKOV3 and OVCAR3 cells (FIG. 3G). In contrast, BRCA1-IRIS silencing (using siRNA) or inactivation (using IRIS peptide) decreased expression and inactivated AKT and ERK (FIG. 34).

Phosphorylation of cytoplasmic or nuclear FOXO3a by p-AKT and/or p-ERK promotes MDM2 binding and priming ubiquitylation, which is then followed by Skp2 branching ubiquitylation and FOXO3a degradation (Huang and Tindall, 2011). FOXO was less phosphorylated in LY, PD as well as IRIS-silenced/inactivated SKOV3 or OVCAR3 cells (FIG. 34). Moreover, LY reduced MDM2 and not Skp2 expression in both cell lines, and PD reduced Skp2 and not MDM2 expression at least in SKOV3 (FIG. 34), whereas, BRCA1-IRIS silencing/inactivation significantly decreased expression of MDM2 and Skp2 in both cell lines (FIG. 34). Consistently, in BRCA1-IRIS silenced/inactivated cells accumulation of unphosphorylated/stabilized FOXO3a was detected. In contrast, FOXO3a was still decreased to different degrees in LY or PD treated cells (FIG. 34). Taken together, the data suggest that BRCA1-IRIS activation promotes cisplatin resistance through activation of TrkB and ErbB2, which then activates AKT and/or ERK and inhibits FOXO3a.

Example 7

BRCA1-IRIS Silencing or Inactivation Decreases Ovarian Cancer Cells Aggressiveness.

To determine whether BRCA1-IRIS silencing or inactivation impacts ovarian cancer cells aggressiveness, several in vitro experiments were performed.

Figure 35:
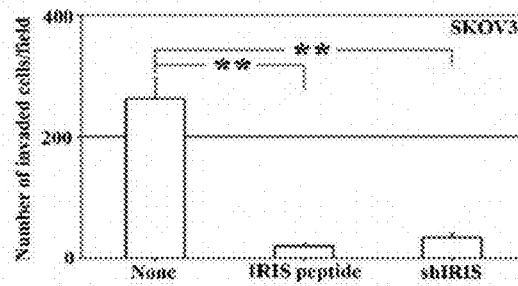
FIG. 35 provides a quantitative analysis of invasion in matrigel coated Boyden chambers by untreated SKOV3 cells or cells treated with IRIS peptide or transfected with BRCA1-IRIS shRNA.
Figure 36:
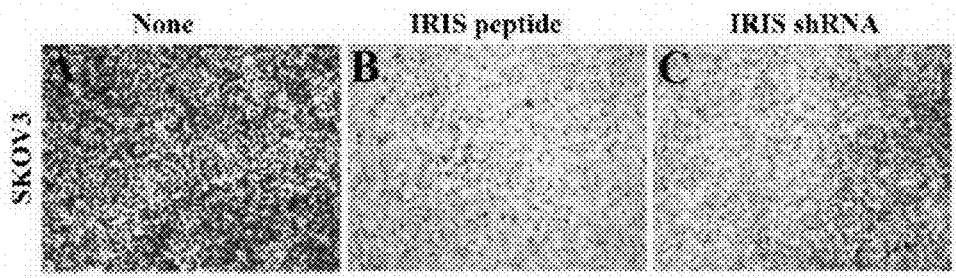
FIG. 36 shows an in vitro invasion assay done in matrigel-coated Boyden chambers using SKOV3 cells untreated (A), treated with IRIS peptide (B) or expressing BRCA1-IRIS shRNA (C).

Invasion assay: Control (transfected with siLuc or treated with scrambled peptide, 5 µM) or shIRIS expressing SKOV3 cells were layered on top of matrigel-coated Boyden chambers. Some cultures were treated with 5 µM IRIS peptide. Seventy-two hours later, cells that invaded the matrigel and migrated to the lower side of the chambers were stained with Crystal Violet, counted and photographed. Compared to control-treated SKOV3 cells, IRIS peptide-treated cells showed ~100 fold (see Suppl. FIG. 35) decreased ability to invade (compare B to A in FIG. 36). Similarly, BRCA1-IRIS silenced cells also lost their invasion ability by ~75 fold (compare C to A in FIG. 36 and FIG. 35).

Figure 37:
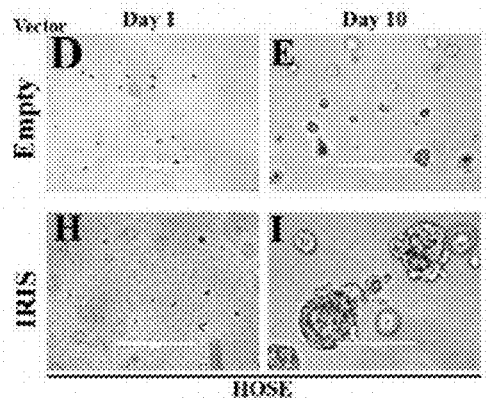
FIG. 37 provides the results of an acini formation assay done in matrigel-coated wells using HOSE cells expressing an empty vector (D and E) or BRCA1-IRIS cDNA (H and I) at day 1 or day 10.
Figure 38:
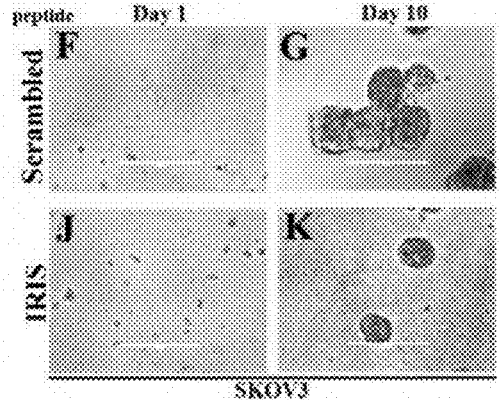
FIG. 38 provides the results of an acini formation assay done in matrigel-coated wells using SKOV3 cells treated with scrambled peptide (F and G) or IRIS peptide (J and K) at day 1 or day 10.
Figure 39:
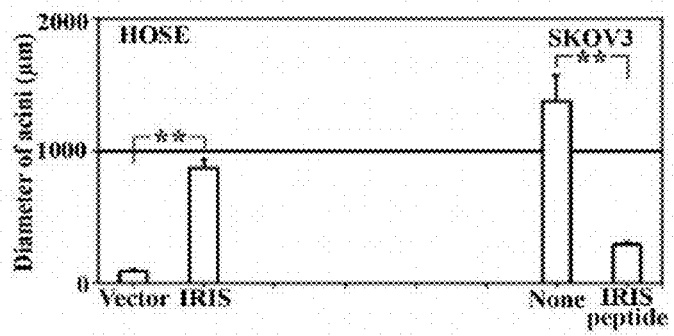
FIG. 39 shows a quantitative analysis of the size of acini (diameter in μm) formed by HOSE or HOSE/IRIS cells (left) as well as acini formed using SKOV3 or SKOV3 cells treated with IRIS peptide (right).

Three-dimensional (3D) growth: A day after HOSE (FIG. 37) or HOSE/IRIS (FIG. 37) cells were layered in matrigel, they formed small/organized/round acini. By day 10, while HOSE cells still showed slightly bigger/organized/round acini (FIG. 37), HOSE/IRIS cells showed large/disorganized/non-round acini (FIG. 37). Conversely, at day 1, SKOV3 treated with scrambled or IRIS peptide showed small/organized/round acini (FIG. 38), whereas by day 10 scrambled peptide treated cells formed large/disorganized/non-round acini, while IRIS peptide-treated cells (added every third day) showed slightly bigger/organized/round acini (FIG. 38). Notably, BRCA1-IRIS overexpression enhanced HOSE cells' ability to form invasive structures in matrigel by >500 fold (FIG. 39, left), whereas BRCA1-IRIS silencing decreased that same ability in SKOV3 cells by >500 fold.

Figure 40:
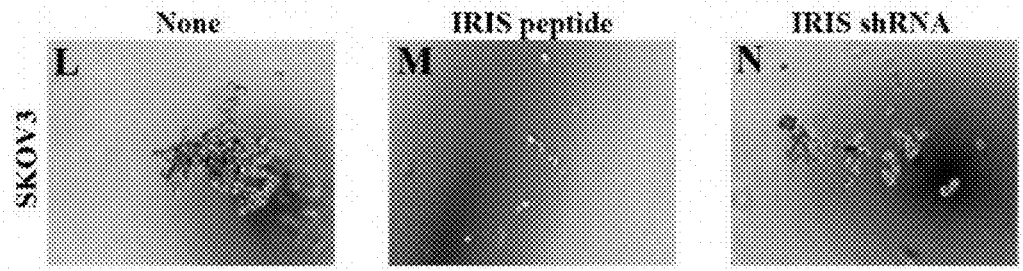
FIG. 40 shows a hanging drops assay done using untreated SKOV3 cells (L) or SKOV3 cells treated with IRIS peptide (M) or expressing BRCA1-IRIS shRNA (N) at day 7.
Figure 41:
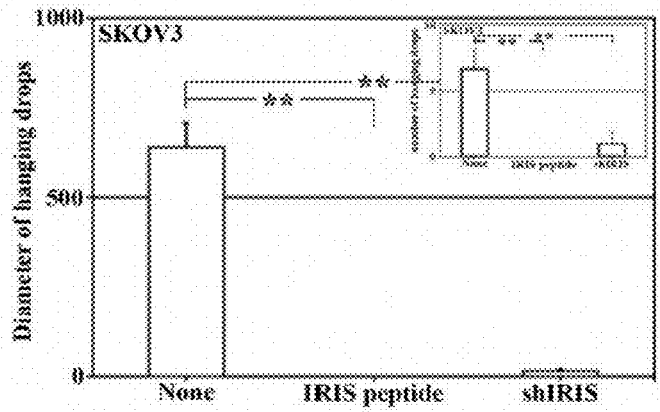
FIG. 41 provides a quantitative analysis of the diameter (μm) of hanging drops formed by SKOV3 cells untreated, treated with IRIS peptide or transfected with BRCA1-IRIS shRNA. The inset shows the actual numbers of these drops.

Hanging drops: In this technique, the anchorage independent growth ability of cells was measured. A complete loss of ability of SKOV3 cells was observed when treated with IRIS peptide (5 µM, FIG. 40 and FIG. 41) compared to scrambled peptide (5 µM, FIG. 40 and FIG. 41). Moreover, BRCA1-IRIS silenced cells also failed to form hanging drops (FIG. 40 and FIG. 41). As an illustrative measure, the diameter of the drops was significantly decreased by BRCA1-IRIS silencing or inactivation (see inset in FIG. 41).

Figure 42:
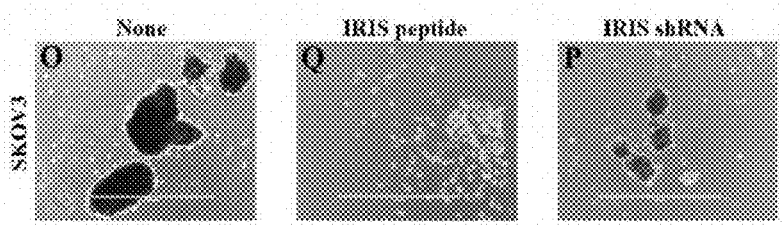
FIG. 42 shows a tumor-sphere assay done using SKOV3 cells untreated (O), treated with IRIS peptide (Q) or expressing BRCA1-IRIS shRNA (P).
Figure 43:
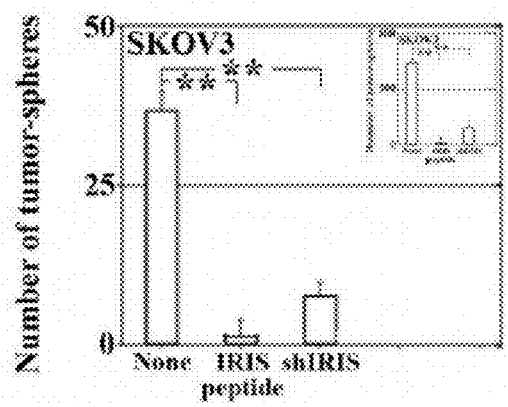
FIG. 43 provides a quantitative analysis of the number of tumor-spheres formed by SKOV3 cells untreated, treated with IRIS peptide or transfected with BRCA1-IRIS shRNA.
Figure 44:
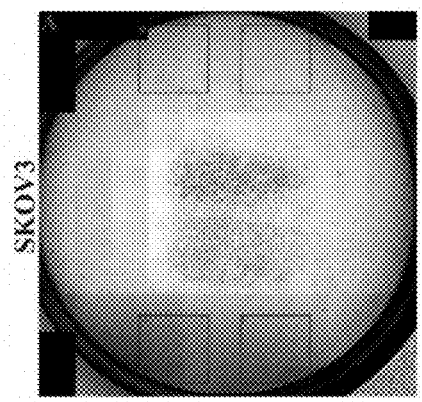
FIG. 44 shows migration by SKOV3 cells.
Figure 45:
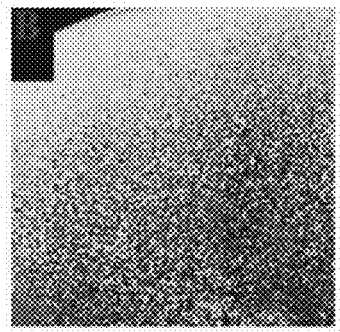
FIG. 45 provides an image that was isolated from the top, left box (B) shown in FIG. 44, showing the number of cells migrated, wherein the image was converted using a gradient mapping tool.
Figure 46:
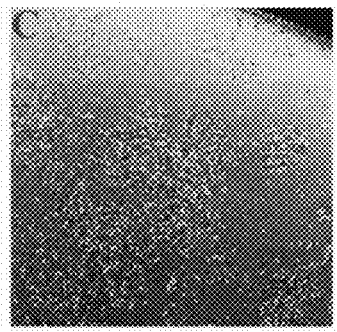
FIG. 46 provides an image that was isolated from the top, right box (C) shown in FIG. 44, showing the number of cells migrated, wherein the image was converted using a gradient mapping tool.
Figure 47:
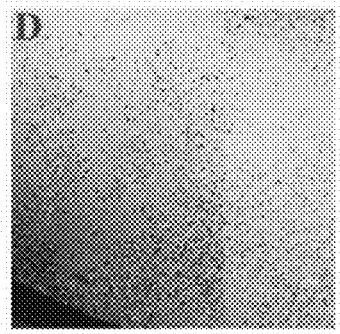
FIG. 47 provides an image that was isolated from the lower, left box (D) shown in FIG. 44, showing the number of cells migrated, wherein the image was converted using a gradient mapping tool.
Figure 48:
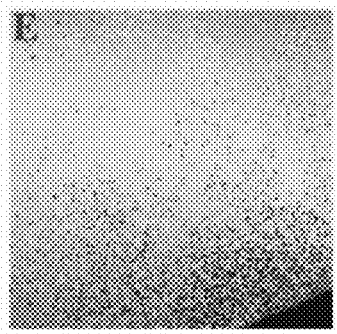
FIG. 48 provides an image that was isolated from the lower, right box (E) shown in FIG. 44, showing the number of cells migrated, wherein the image was converted using a gradient mapping tool.
Figure 49:
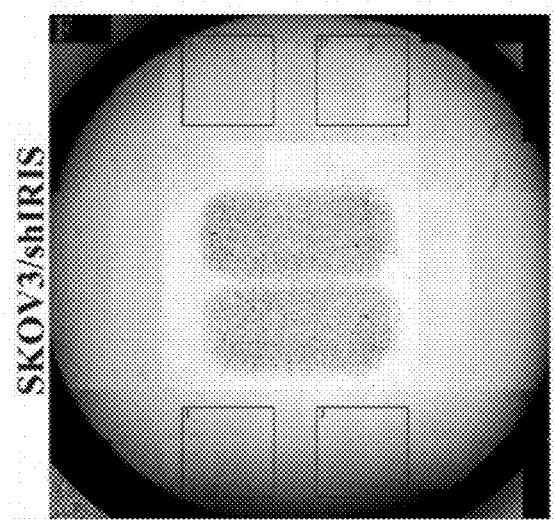
FIG. 49 shows migration by SKOV3/shIRIS cells.
Figure 50:
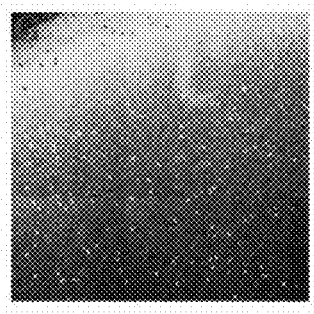
FIG. 50 provides an image that was isolated from the top, left box (G) shown in FIG. 49, showing the number of cells migrated, wherein the image was converted using a gradient mapping tool.
Figure 51:
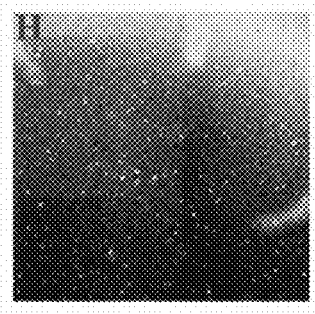
FIG. 51 provides an image that was isolated from the top, right box (H) shown in FIG. 49, showing the number of cells migrated, wherein the image was converted using a gradient mapping tool.
Figure 52:
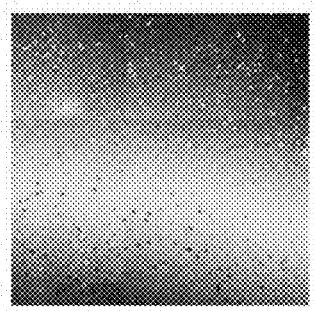
FIG. 52 provides an image that was isolated from the lower, left box (I) shown in FIG. 49, showing the number of cells migrated, wherein the image was converted using a gradient mapping tool.
Figure 53:
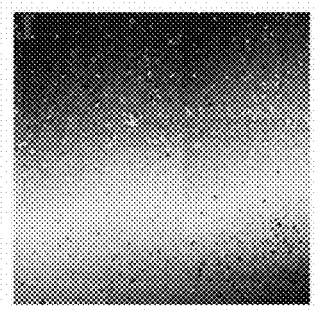
FIG. 53 provides an image that was isolated from the lower, right box (J) shown in FIG. 49, showing the number of cells migrated, wherein the image was converted using a gradient mapping tool.

Tumor-sphere: SKOV3 cells treated with scrambled or IRIS peptide (5 µM, added every third day) or expressing BRCA1-IRIS shRNA were grown in ultra-low binding culture dishes as single cells. Two weeks later, while SKOV3 cells formed large numbers of large tumor-spheres (FIG. 42 and FIG. 43), SKOV3 cells treated with 5 µM IRIS peptide formed no tumor-spheres (although they remained alive as single cells, FIG. 42 and FIG. 43). IRIS-silenced cells only formed few very small tumor-spheres (FIG. 42 and FIG. 43). BRCA1-IRIS silencing led to ~7 fold decrease in tumor-sphere number (FIG. 43) and diameter (FIG. 43, inset), and an even more pronounced effect was detected with IRIS peptide (FIG. 43, and inset).

Figure 54:
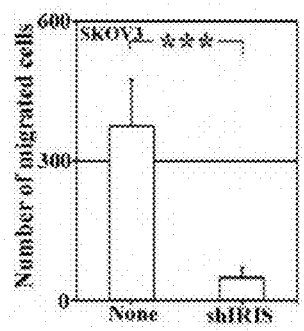
FIG. 54 is a bar graph that illustrates the number of SKOV3 or SKOV3 transfected with shIRIS cells that migrated.
Figure 55:
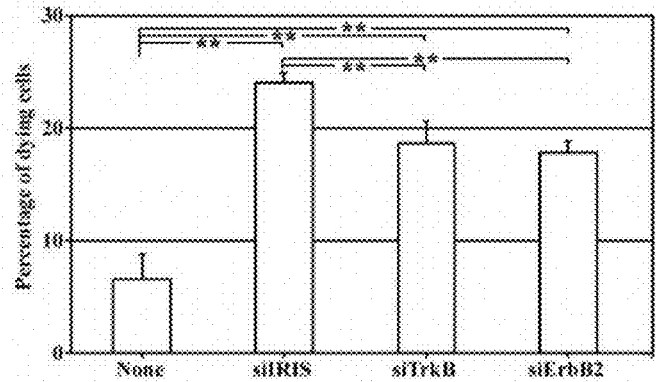
FIG. 55 presents the results of a polyHema assay, illustrating the percentage of SKOV3 cells that died following (i) no treatment, (ii) BRCA1-IRIS, (iii) TrkB or (iv) ErbB2 silencing using specific siRNA.
Figure 56:
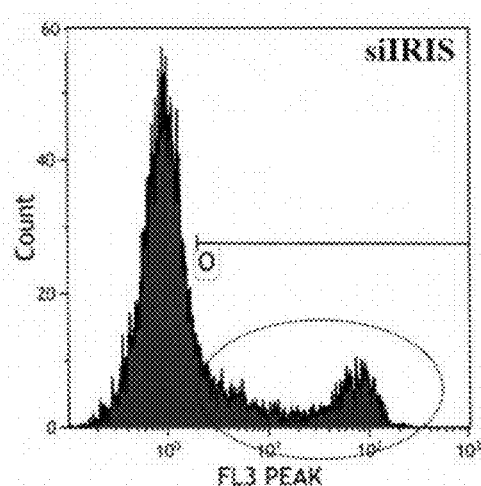
FIG. 56 shows a representative FACS analysis BRCA1-IRIS siRNA transfected cells stained with PI (n=3). The oval shows a fraction of PI stained/dying cells.
Figure 57:
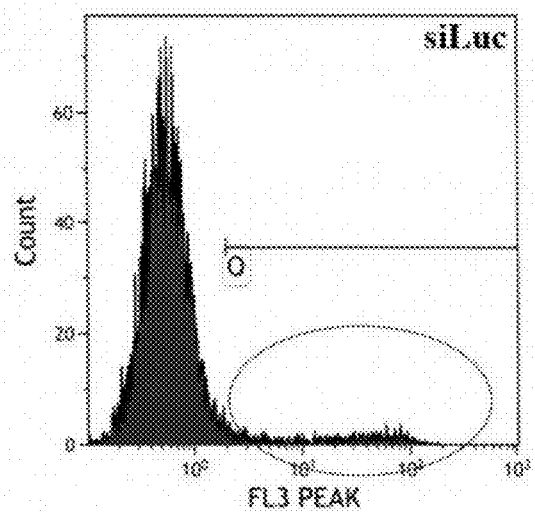
FIG. 57 shows a representative FACS analysis of luciferase siRNA transfected cells stained with PI (n=3). The oval shows a fraction of PI stained/dying cells.
Figure 58:
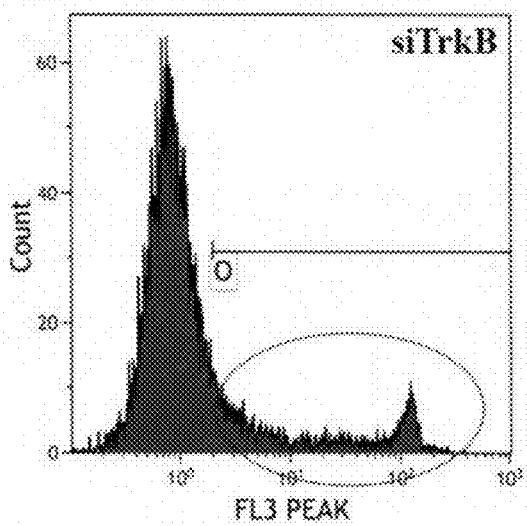
FIG. 58 shows a representative FACS analysis of TrkB siRNA transfected cells stained with PI (n=3). The oval shows a fraction of PI stained/dying cells.
Figure 59:
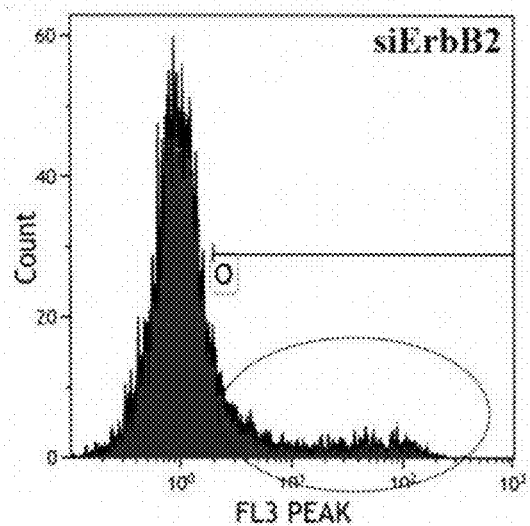
FIG. 59 shows a representative FACS analysis of ErbB2 siRNA transfected cells stained with PI (n=3). The oval shows a fraction of PI stained/dying cells.

Migration: To measure the BRCA1-IRIS effect(s) on ovarian cancer cell motility, inserts were positioned in the middle of wells of 6 well plates, where SKOV3 or SKOV3/shIRIS cells were layered in complete medium. When confluent, the inserts were removed, floating cell washed, the wells filled with medium, and cells' ability to migrate (outward) and the distance they travelled was monitored under microscope. As shown, compared to control SKOV3 cells (FIG. 44-48), BRCA1-IRIS silenced SKOV3 lost most of their ability to migrate (FIG. 49-53). Indeed, quantitatively, SKOV3/shIRIS cells had 10-fold reduction in their ability to migrate (FIG. 54). Similar results were obtained in all these assays using another aggressive ovarian cancer cell line; OVCR3. Taken together, these data strongly suggest that suppressing BRCA1-IRIS expression or activity significantly reduces the aggressiveness of ovarian cancer cells, in vitro. These properties could increase tumor-cell survival under tough conditions, such as anoikis.

Example 8

BRCA1-IRIS Overexpression Induces Anoikis Resistance in Ovarian Cancer Cells.

TrkB overexpression correlates with anoikis resistance and metastasis in ovarian cancer (Geiger and Peeper, 2007; Yu et al., 2008; Smit et al., 2009; Zheng et al., 2011). It is possible that BRCA1-IRIS overexpression promotes anoikis resistance and tumor cell survival in ascetic fluid before metastasis by enhancing TrkB and its ligand BDNF expression. To elucidate that point and to evaluate whether ErbB2 is also involved, SKOV3 cells were either transfected with luciferase, BRCA1-IRIS, TrkB or ErbB2-specific siRNAs for 48 hours. Cells were then collected by trypsinization, and equal numbers were re-plated in polyHema-coated wells. Twenty-four hours later, floating cells were collected, incubated for one minute in propidium iodide (PI) solution, and they were immediately analyzed by FACS. PI-stained cells should represent dead cells, since PI will only diffuse into cells with ruptured cell membranes (a hallmark of cell death by anoikis).

Indeed, BRCA1-IRIS silencing led to ~3.6 fold (FIG. 55 and compare FIG. 56 to FIG. 57), whereas TrkB silencing led to ~2.6 fold (FIG. 55 and compare FIG. 57 to FIG. 58) and ErbB2 silencing led to 2.4 fold (FIG. 55 and compare FIG. 59 to FIG. 57) increase in death by anoikis in SKOV3 cells. Taken together, the data suggest that BRCA1-IRIS overexpression enhances anoikis resistance in ovarian cancer cells in a TrkB and ErbB2 dependent manner.

Example 9

BRCA1-IRIS Overexpression Induces Ovarian Tumor Formation and Metastasis

Figure 60:
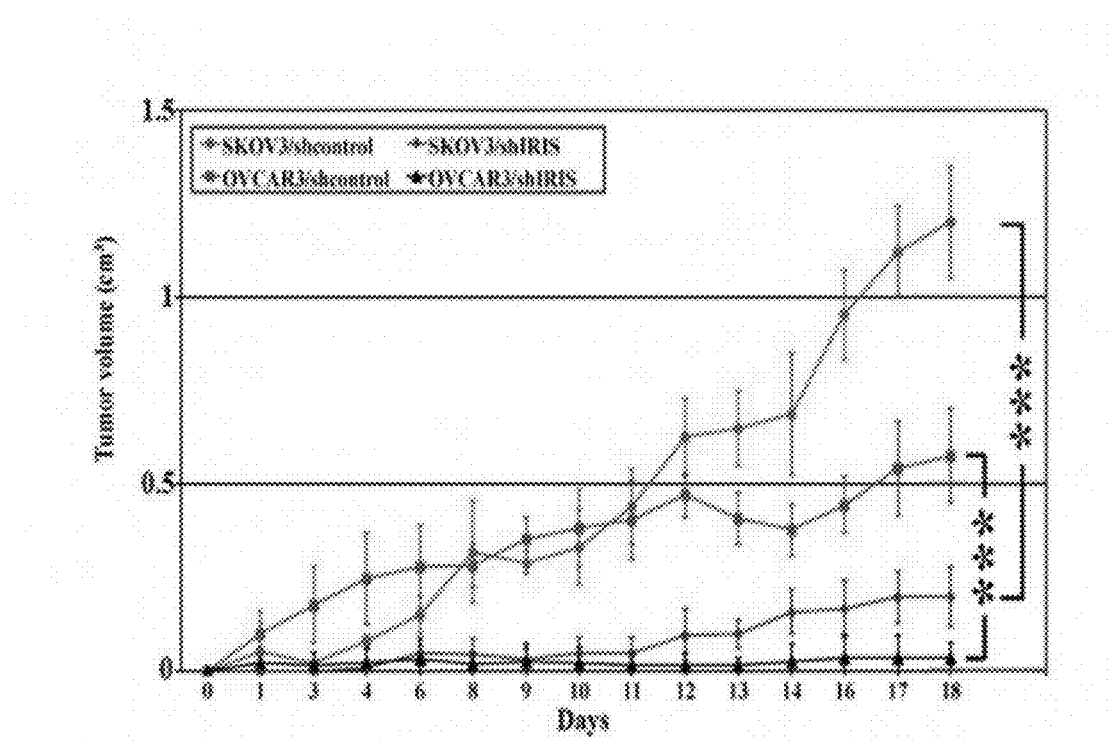
FIG. 60 presents the volumes of respective tumors developed in SCID mice. From highest to lowest tumor volume at 18 days, the first line, that is the line representing the highest tumor volume at 18 days, represents tumors developed using SKOV3 cells expressing control shRNA (n=6). The next line, that is the line extending just above 0.5 $cm^3$ at 18 days, represents tumors developed using OVCAR3 expressing control shRNA (n=6). The third line from the top represents tumors developed using SKOV3 cells expressing BRCA1-IRIS shRNA (n=6), and the lowest line of the graph (fourth from the top) represents tumors developed using OVCAR3 cells expressing BRCA1-IRIS shRNA (n=6). BRCA1-IRIS overexpression promotes ovarian tumor formation and metastasis.
Figure 61:
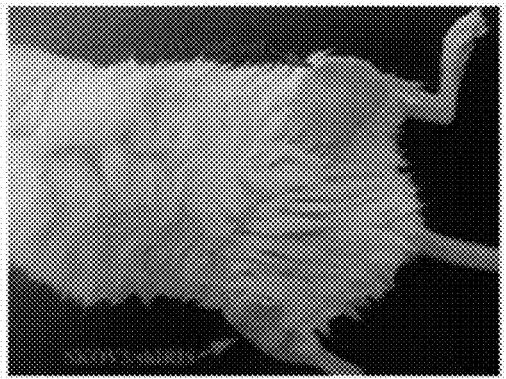
FIG. 61 is a representative image of tumors using SKOV3 cells expressing control shRNA (see right leg) or SKOV3 cells expressing BRCA1-IRIS shRNA (see left leg).
Figure 62:
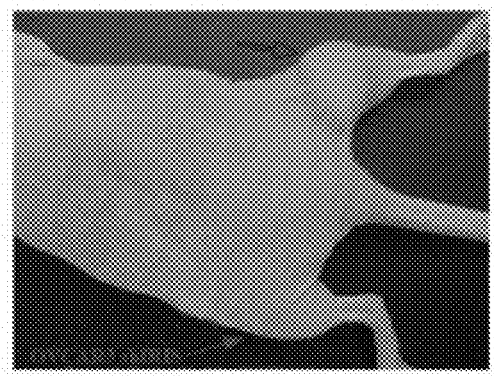
FIG. 62 is a representative image of tumors using OVCAR3 cells expressing control shRNA (see right leg) or OVCAR3 cells expressing BRCA1-IRIS shRNA (see left leg).

Tumor formation: SKOV3 and OVCAR3 cell lines (both express high levels of BRCA1-IRIS; see Chock et al., 2010 and FIGS. 12-14) expressing empty vector or BRCA1-IRIS shRNA (hereafter shIRIS) were injected subcutaneously in SCID or Nu/Nu mice (n=6/cell line). Control shRNA-expressing cells formed tumors (FIG. 6A-C), while BRCA1-IRIS-depleted cells did not (FIG. 60, FIG. 61, FIG. 62). Indeed a 6-fold decrease in the ability of both cells to form tumors was observed (FIG. 60). This suggests that BRCA1-IRIS overexpression promotes ovarian tumor formation.

Figure 63:
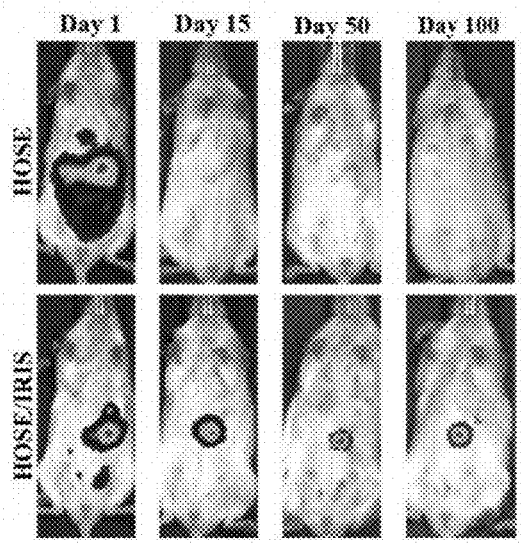
FIG. 63 provides representative images of mice injected in their respective abdomens with HOSE (upper panel) or HOSE/IRIS cells (lower panel) at day 1, 15, 50 and 100 post-injection.
Figure 64:
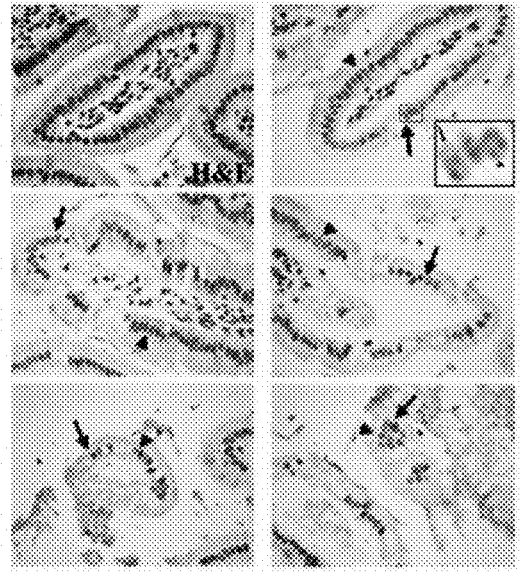
FIG. 64 presents metastases of the human HOSE/IRIS cells shown in FIG. 63, lower panel, at day 100 in the colon (arrows). Arrowheads show unstained mouse colon cells.

Metastasis formation: To evaluate next whether BRCA1-IRIS overexpression is also involved in ovarian cancer metastasis, HOSE and HOSE/IRIS cells expressing luciferase were injected directly into the peritoneal cavity (since this is the first site dislodged ovarian cancer cells move to before metastasizing) of SCID mice (n=6/cell line). Using the Xenogen in vivo imaging machine, these cells were followed for about 100 days. While both cell lines were present in the peritoneal at day 1 (FIG. 63, $1^{st}$ column), by day 15 all HOSE cells disappeared (most likely the body had cleared them), whereas HOSE/IRIS cells persisted in the abdomen at days 15, 50 and even 100 (FIG. 63, $2^{nd}$, $3^{rd}$ and $4^{th}$ columns, respectively). Interestingly, the HOSE/IRIS signal became more confined to a small area of the abdomen with time (compare 1st to $2^{nd}$, $3^{rd}$ and $4^{th}$ in FIG. 63, lower panels). This perhaps suggests that BRCA1-IRIS overexpressing cells might have moved into some of the organs occupying that part of the respective mice and formed metastasis. As such, further investigation revealed that tissues occupying this area (i.e. intestine, colon, liver, etc.), as well as the peritoneal membrane and ovaries, was isolated from these mice and IHC stained with anti-human BRCA1-IRIS antibody (does not cross react with mouse IRIS, not shown). No human cells were found in the peritoneal membrane (where the injection took place, data not shown), suggesting that the luciferase signal observed was omitted from cells that migrated out from there, as perhaps metastases to other organs. Among the tissues analyzed, foci of human BRCA1-IRIS-positive cells were found throughout the colon (see arrows in FIG. 64), intermingled with mouse colon cells (see arrowheads in FIG. 64). Taken together, these data show that BRCA1-IRIS overexpression also promotes ovarian cancer metastasis.

Example 10

BRCA1-IRIS Inactivation Sensitizes Ovarian Tumors to Cisplatin.

Further, to determine whether IRIS peptide could have any efficacy in vivo and/or whether it sensitizes ovarian tumors to low, clinically relevant concentrations of cisplatin, four sets of nude mice (n=6 each) were subcutaneously injected with SKOV3 cells. Ten days later, when tumors were ~250 mm$^3$ in volume, one group was treated with controls (i.e. DMSO delivered i.p. and scrambled peptide delivered directly into the tumors, i.t.), a second group was treated with cisplatin (5 mg/kg, delivered i.p.), a third group was treated with IRIS peptide (10 mg/kg, injected i.t.), and a fourth group was treated with both. Treatments were delivered every third day for a total of four times. For the next 16 days, tumors were measured daily with a caliper. Mice were then sacrificed, and their tumors or their remnants were taken.

Tumors in vehicle-treated mice continued to grow exponentially until they were ~5 times their size at the start of the treatment (see black line in FIG. 65 and inset). Cisplatin and IRIS peptide treatment at the concentrations used led to significant suppression of tumor growth. Indeed, at day 16, cisplatin treatment led to ~40% and IRIS treatment led to ~50% reduction in tumor size (see blue and red line, respectively in FIG. 7A and inset). Impressively, mice treated with the combination showed 90-95% reduction in their tumor size (see green line in FIG. 65 and inset), showing that in addition to its own efficacy, IRIS peptide also sensitizes ovarian tumors to killing by cisplatin.

Isolated tumors were mounted, sectioned and IHC stained for BRCA1-IRIS and survivin. Although cisplatin treatment significantly reduced tumor growth, as expected, the remaining tumor cells showed increased IRIS and survivin expression (FIG. 7B). In contrast, tumor treated with IRIS peptide or cisplatin and IRIS peptide, as well as tumor formed using shIRIS expressing SKOV3 cells, showed almost complete absence of BRCA1-IRIS and survivin staining (FIG. 66). It is possible that SKOV3 contain a heterogeneous population of cells that differ in their BRCA1-IRIS expression and thus that the remaining tumors are from those expressing no or low BRCA1-IRIS. These data show that BRCA1-IRIS inactivation sensitizes ovarian tumor cells to cell death by low concentrations of cisplatin.

BRCA1-IRIS is overexpressed in the majority of ovarian cancer cell lines (Chock et al., 2010b). BRCA1-IRIS expression and activity seem to be vital for their proliferation and survival since BRCA1-IRIS depletion reduces both proliferation and survival rates (Chock et al., 2010b). Indeed, BRCA1-IRIS silencing in two aggressive ovarian cancer cell lines, namely OVCAR3 and SKOV3, suppresses their growth and aggressiveness in culture and also suppresses tumor formation in SCID mice. Furthermore, as described above, BRCA1-IRIS overexpressing HOSE cells can engraft the abdomen and then form intestinal metastases. Interestingly, in a human, the colon is one of the organs that disseminated ovarian cancer cells metastasize to after they leave the peritoneal cavity (Ponnusamy et al., 2010; O'Hanlan et al., 1995). It is thus possible to suggest that BRCA1-IRIS is involved in the full spectrum of ovarian cancer, from initiation to metastasis, as well as in cisplatin-resistance recurrence.

Treating HOSE cells with low concentration of cisplatin upregulates BRCA1-IRIS. Like, intrinsic BRCA1-IRIS overexpression, cisplatin-acquired BRCA1-IRIS overexpression activates AKT, which led to FOXO3a downregulation (most likely due to degradation) and thus induction of survivin expression among other proliferation and survival factors. This suggests that whether it is disease-related or chemotherapy-induced, BRCA1-IRIS overexpression could induce growth of drug resistance recurrent ovarian cancer. Therefore, an anti-BRCA1-IRIS drug could sensitize ovarian cancers to cisplatin and enhance the chances of patients' survival.

Experimental Procedures and Materials

Cell culture and antibodies. OVCAR3 and SKOV3 cells were purchased from the American Type Culture Collection. OVCAR420 and OV90 cells were kind gift from Dr. Said (University of Virginia, Va., USA). Immortalized ovarian surface epithelial cell line (HOSE) was kindly provided by Dr. Nelly Auersperg (University of British Columbia, Vancouver, Canada). HOSE cells were grown in medium containing 45% Medium 199, 45% MCDB105, and 10% fetal bovine serum (FBS; HyClone, USA). All other cell lines were grown in RPMI 1640 (Invitrogen, USA) supplemented with 10% FBS.

Antibodies. The antibodies used in the aforementioned examples were: rabbit anti survivin (#2808), rabbit anti ErbB2 (#2165), rabbit anti CyclinD1 (#2978), rabbit anti PTEN (#9188), rabbit anti AKT (#2938), rabbit anti pAKT (Ser 473, #4060), rabbit anti ERK (#4695), rabbit anti Bcl2 (#2870), rabbit anti Bcl-XL (#2762) and rabbit anti Skp2 (#4358), and all were purchased from Cell Signaling Inc. Further, rabbit anti Foxo3a (ab47409), rabbit anti TrkB (ab 18987) and rabbit p(Y515)-TrkB (ab51187) were obtained from abcam Inc. Mouse anti NRG1 (MAB377) was purchased from R&D Systems, mouse anti NF-κB/p65 (IMG-150A) and rabbit anti MDM2 (s1357) were obtained from Imgenex and Epitomics, respectively, mouse anti actin (cp01) was obtained from Calbiochem, and mouse anti-human BRCA1-IRIS was developed by the present inventor(s).

Lentiviral and shRNA construction and transduction. Each of (i) ecotropic lentivirus with pLenti6/V5-D-TOPO-vector and (ii) pLenti6N5-D-TOPO-BRCA1-IRIS was produced using Lenti-X HTX packaging systems (Clonetech Laboratories, Inc. USA) To generate stable HOSE/VECTOR and HOSE/IRIS cell lines, HOSE cells were transduced with pLenti6/V5-D-TOPO-vector or with pLenti6N5-D-TOPO-BRCA1-IRIS viral supernatant in the presence of 4 µg/ml polybrene (Millipore). Infected cells were selected with blasticidin (10 µg/ml). The shRNA was designed using 'shRNA Design Tool' from the Integrated DNA Technologies web site. The designed oligonucleotides contain both the sense and antisense siRNA sequences separated by a short loop sequence and have BamHI and EcoR1 compatible overhanging ends. pSIREN-RetroQ plasmid from addgene was used to construct BRCA1-IRIS shRNA vector. The expression of small hairpin RNA (shRNA) is controlled via the U6 promoter. To generate shRNA duplex, the sense and antisense oligonucleotides were annealed and double-stranded oligonucleotides were cloned into the pSIREN-RetroQ plasmid. To establish BRCA1-IRIS shRNA-stable clones, ecotropic retroviral supernatants containing pSIREN-RetroQ-shRNA plasmid or the vector alone were produced. SKOV3 and OVCAR3 cells were infected with retroviral supernatant and infected cells were selected with puromycin 5 µg/ml.

Immunohistochemistry (IHC). Ovarian tissue microarrays comprised of normal, cancer and metastatic tissues were purchased from US Biomax, Inc. Paraffin-embedded tissue sections were de-waxed in xylene and rehydrated in alcohol. Antigen-retrieval for FOXO3a and survivin was performed by heating the slides in citrate buffer (10 µM, pH 6.0) using microwave for 10 minutes. Slides were then cooled to room temperature (RT) and washed with water followed by PBS for 15 minutes each. Antigen-retrieval for BRCA1-IRIS was performed by incubating the slides in pepsin (10 µM) for 20 minutes at 37° C. Endogenous peroxidase activity was suppressed by treating the slides with 3% hydrogen peroxide for 10 minutes. After washing steps slides were incubated for 1 hour at room temperature with antibodies to human FOXO3a (Cell Signaling Technology, USA 1:400) and survivin (Cell Signaling Technology, USA 1:400). For BRCA1-IRIS staining, slides were incubated overnight at 4° C. with monoclonal BRCA1-IRIS antibody at a 1:75 dilution. Washed slides were then incubated with horseradish peroxidase labeled secondary antibody (Vectastain Elite ABC Kit; 1 h at RT), developed with diaminobenzidine (DAB), and counterstained with Meyer's hematoxylin for 5 minutes. The same protocol was used for IHC of mouse tumor.

Scoring for immunohistochemical staining. All tumors and staining were evaluated under 4× and 10× magnifications. Staining scoring relied on visual examination of multiple fields within a single IHC-stained tissue slice. Scoring represents: overall stain intensity and the percentage of cancer cells stained. Average of overall staining intensity (score, see Hsu et al., 1981) was valued at Zero being negative (<1% of the cells stained); 1=weak (between 1-10% of cells stained); 2=medium (between 10%-50% of cells stained) and 3=strong (>50% of cells stained). The positive staining scoring method is subjective, and artifacts such as high background or variable stain deposition can skew the results (Choudhury et al., 2010).

Growth factor/cytokine profile. Differential secretion of growth factors and cytokines by HOSE and HOSE/IRIS cells was evaluated using human cytokine antibody array (Ray-Bio®). Conditioned media was prepared by plating equal number of HOSE and HOSE/IRIS cells in serum free medium for 20 hours under standard incubation conditions. Antibody array was developed according to manufactures protocol.

In vivo tumorigenicity assay. Six to eight week old athymic SCID (NOD.CB17-Prdc$^{scid}$ J, Jackson Laboratory) female mice were used for in vivo tumorigenicity assay. Mice were assigned into two groups and injected intraperitoneally with $10 \times 10^6$ HOSE cell expressing TERT and LT alone or TERT, LT and BRCAI-IRIS. Tumor growth was monitored weekly by bioluminescent imaging using IVIS™ Imaging System (Xenogen). Similarly, tumor growth attenuation by BRCA1-IRIS knockdown was studied using BRCA1-IRIS shRNA SKOV3 or OVCAR3 cells. Moreover, adult female athymic SCID mice were inoculated subcutaneously with $5 \times 10^6$ of SKOV3/VECTOR cells in right leg and with SKOV3/sh-BRCA1-IRIS in the left leg. Another set of similar experiments was performed using OVCAR3/VECTOR and OVCAR3/shBRCA1-IRIS cells. Tumors were measured with a caliper and the tumor volume was calculated using the formula $4/3\pi r^3$ (where r is the tumor radius). At the endpoint, tumors were dissected and fixed in 10% formalin for histological and immunohistochemical analysis.

BRCA1-IRIS inhibitory peptide. A synthetic peptide corresponding to amino acids 1365-1399 of BRCA1-IRIS protein (for example, per SEQ ID NO: 1) conjugated with cell and nuclear penetrating sequence (for example, per SEQ ID NO: 2) was used as the BRCA1-IRIS inhibitory peptide. Peptide was dissolved in water at a concentration 1 mM and stored in −80° C.

Cell viability measurement. Cell viability under different experimental conditions was determined using the MTS assay or cell. Briefly, SKOV3, OVACAR3, HOSE and HOSE/IRIS cells ($2.5 \times 10^4$ cells per well) were seeded in 96 well plates and incubated overnight at 37° C. in 10% humidified $CO_2$ atmosphere in varying concentrations of IRIS peptide, or inhibitors of ErbB2 (CP-724714), EGFR (Erlotinib), TrkB (K252a), JNK (SP600125), p38 (SB203580), ERK (PD98059) and PI3'K/AKT (LY294002) inhibitors for 24 hours at 37° C. Cell Titer 96® Aqueous (Promega, Madison, Wis., USA) was used to measure viability following manufactures instructions. Cell viability (%) was expressed as a ratio to control cells×100. Growth inhibition was also determined by manually counting cells in five different microscopic fields. Change in cell numbers (fold) was expressed as a ratio to control cells×100. All experiments were done in at least triplicates, three different times. * is $p \leq 0.05$,  is $p \leq 0.001$ and * is $p \leq 0.0001$.

Transfections of siRNA. siRNAs for human ErbB2 and TrkB were purchased from Ambion and Santa Cruz Biotechnology, USA. Custom synthesized siRNA against BRCA1 IRIS was used. siRNA against luciferase gene was used as the negative control. Sub-confluent cells were transfected in 6- or 96-well plates with ErbB2 (100 nM), TrkB (100 nM), BRCA1 IRIS (200 nM) or control siRNA using Oligofectamine™ reagent (GibcoBRL Inc, USA) following the instructions of the manufacturer. Protein expression was tested by Western blot after 72 hours of siRNA transfection. Cell viability was evaluated by MTS or by manual counting after 72 hours of siRNA exposure alone or in combination with cisplatin exposure (for an additional 24 hours).

Cell Migration Assay. Cell migration was determined using the μ-Dish 35 mm, high Culture-Inserts (ibidi GmbH, Munich, Germany). The insert is in rectangular shape and is separated into two equal compartments. Cells (control and shBRCA1-IRIS cells) were plated inside the compartment. After cells reached confluence, the inserts were removed, making space for the cells to migrate between the compartments and around the compartments. Floating cells were removed by washing the monolayer twice with serum-free medium and the cells were cultured for an additional 24 to 48 hours. Cell migration was recorded using a microscope.

Cell Invasion assay. Growth reduced BD Matrigel™ invasion chamber (24 well plate, 8.0 μm, BD BioCoat™) was used to study the invasion ability of control and shBRCA1-IRIS cells. Cells ($5 \times 10^3$) in complete medium (500 μl) were seeded on the upper compartment, and the lower compartment was filled with 750 μl of complete growth medium. Cells were incubated for 72 hours. The medium from the upper chamber was removed, and the cells on the upper surface of the membrane were removed carefully with a cotton swab. Invasive cells in lower side of the membrane were stained with crystal violet dye for 10 minutes. After staining, the upper chamber was rinse thoroughly with water until the water runs clear. Stained and dry chambers were visualized with microscope and photographed.

Tumor-sphere forming assay. Subconfluent monolayer cells were trypsinized and dissociated thoroughly to prepare single cell suspension. 1000 cells were plated, per well, onto ultra-low attachment 6-well plates (Corning Life Sciences, Union City, Calif.) in Dulbecco's modified Eagle's medium (DMEM)/F12 supplemented with 10% FBS, 2% B27 (Invitrogen), 10 ng/ml basic-fibroblast growth factor and 10 ng/mL epidermal growth factor. Cells were then incubated at 37° C. in humidified air with 10% $CO_2$. 500 μl of medium was added to each well every 3 days, the medium containing the scrambled or IRIS peptide. At day ten, the number of spheres in each well was counted using inverted microscope, and diameter was calculated using an internal microscopic scale.

Hanging Drop Method. Single-cell suspensions were made from monolayer cultures in growth medium. Cell density used was 250 cells per drop (20 μl) of medium dispensed onto a 6 cm dish (Corning Life Sciences, Union City, Calif.). The dish was then inverted, the drops were held in place by surface tension, and cells accumulated at the free liquid-air interface. The dishes were placed on a tray with water and incubated under standard conditions. Hanging cell-drops formed was analyzed using microscope. All experiments were done in triplicate.

Efficacy of BRCA1-IRIS inhibitory peptide, in vivo. Six to eight week old female athymic SCID mice were injected subcutaneously with $2.5 \times 10^6$ SKOV3 cells in the flank region. Their respective tumor growth was measured with a caliper. When the tumor volume reached 250 $mm^3$, mice were randomly grouped into four groups. One group (control) was treated with scrambled peptide (10 mg/kg) and DMSO. A second was treated with BRCA1-IRIS inhibitory peptide (10 mg/kg, body weight). The third group was treated with cisplatin (5 mg/kg, body weight). And finally, the fourth group was treated with a combination of BRCA1-IRIS inhibitory peptide (10 mg/kg) and cisplatin (5 mg/kg). Routes of administration were for peptides intratumoral (i.t.) and for DMSO/cisplatin intraperitoneal (i.p.). Peptide and cisplatin was given every third day for a total of four times. Change in tumor volume was measured to monitor the efficacy of the treatment. At the endpoint, tumors were dissected and fixed in 10% formalin for histological and immunohistochemical analysis.

II. Breast Cancer Related Examples

Taxanes, more particularly paclitaxel emerged recently as powerful chemotherapeutic compound for breast, prostate, ovarian, lung, head and neck and other cancers (Ozols, 2000; Kosmas et al., 2000; De Lena et al., 2000; Mekhail and Markman, 2002; Jimenez et al., 2013). Paclitaxel is also active against other chemotherapy refractory cancers, e.g., previously treated lymphomas, small cell lung cancers, bladder and germ cell tumors (Wong et al., 2012; Mekhail and Pal et al., 2013), and against AIDS-associated Kaposi's sarcoma (Dhillon et al., 2005). Paclitaxel polymerizes tubulin, which disrupts the normal microtubule dynamics causing cell death (Mekhail and Markman, 2002).

Despite paclitaxel's preclinical and clinical success, a few major obstacles remain. Primarily, intrinsic or acquired paclitaxel resistance that develops for instance following alterations of tubulin structure or amplification of drug-efflux pumps (Westerhoff et al., 2000). Another important obstacle is the toxicities that develop following treatment (by high dosages), which includes hypersensitivity reaction, neurotoxicity and hematological toxicities (Kadoyama et al., 2011; Tanimukai et al., 2013). It is therefore important to understand the various mechanisms leading to paclitaxel-resistance in order to design novel and more accurate therapies. Maximum paclitaxel effect could be achieved if an initial apoptotic response to relief some of the cell density and intra-tumoral pressure can be obtained (Symmans, 2001).

Moreover, survivin, a structurally unique member of the inhibitor of apoptosis proteins (IAP) family is involved in cell division control and inhibition of apoptosis (Zaffaroni and Daidone, 2002). Survivin anti-apoptotic function stems from direct or indirect ability to inhibit caspases (Nassar et al., 2008; Tang et al., 2009). Survivin is a poor prognostic factor in several tumor types, and appears to be involved in tumor cell resistance to ionizing radiation and some anticancer agents e.g., paclitaxel (Su et al., 2010; Xie et al., 2012; Waligórska-Stachura et al., 2012; Erpolat et al., 2012; Ekeblad et al., 2012). Survivin expression is induced following paclitaxel exposure in breast cancer cells (Capalbo et al., 2007; Pennati et al., 2007; Shen et al., 2012). Survivin expression is negatively controlled by Forkhead Box Class O (FOXO) transcription activity, which is suppressed in tumor cells by AKT (Yang and Hung, 2009; Hagenbuchner and Ausserlechner, 2013).

FOXO proteins play a pivotal role in the regulation of a myriad of cellular functions including cell cycle arrest, cell death and protection from stress stimuli (Yang and Hung, 2009). Perturbation of FOXO's function deregulates cell proliferation and leads to accumulation of DNA damage (Hu et al., 2004; Yang and Hung, 2009). PI3'K/AKT or RAS/MAPK, cell survival pathways increases phosphorylation of FOXOs at different sites, causing FOXOs nuclear exclusion and degradation (Finnberg and El-Deiry, 2004; Yang and Hung, 2009). Indeed, constitutive AKT-activation is frequently correlated with cytoplasmic FOXO3a and decreased patient survival in breast, prostate, glioblastoma, rhabdomyosarcoma and leukemia (Hu et al., 2004; Zhange et al., 2011; Huang and Tindall, 2011). Drugs like paclitaxel, imatinib and doxorubicin have been shown to achieve their therapeutic effects through activation of FOXO3a and FOXO3a targets (Sunters et al., 2003; Kikuchi et al., 2007; Gomes et al., 2008).

Triple negative (TNBC), or basal-like breast cancer (BLBC), is the most aggressive breast cancer subtype. TNBC is defined by the lack of estrogen (ER) and progesterone (PR) receptors, and ErbB2 is not amplified. Therefore patients with this subtype cannot be treated with Tamoxifen or Herceptin. About 20% of all breast cancer patients in the USA have TNBC or BLCL tumors. TNBC is prevalent in young African American women, has the poorest prognosis, and tumors tend to grow faster and likely to spread to other parts faster and often also harbor BRCA1 mutation. Although TNBC patients are initially responsive to chemotherapeutic drugs, such as paclitaxel, they often recur with chemotherapy-resistant visceral, bone and brain metastasis.

Although the BRCA1 locus product; BRCA1-IRIS shares 1365 residues with the full-length product of this locus; the tumor suppressor BRCA1/p220 (ElShamy and Livingston, 2004; Furuta et al., 2005), unlike BRCA1/p220, BRCA1-IRIS possesses oncogenic functions. For example, BRCA1-IRIS overexpression induces over-replication by inhibiting geminin negative function at DNA replication origins (ElShamy and Livingston, 2004), over-proliferation by up-regulating Cyclin D1 expression (Nakuci et al., 2006; Hoa and ElShamy, 2007), apoptosis-resistance in the face of chemo-, geno- and cell-toxic stresses in human mammary epithelial (HME) and ovarian surface epithelial (HOSE) cells by inhibiting p53 and/or enhancing AKT and survivin expression and activation (Chock et a., 2010a and b). Moreover, a negative feedback mechanism between BRCA1/p220 and BRCA1-IRIS has been reported, in which one inhibits the other (Shimizu et al., 2012a and b). The majority of breast tumors, especially high-grade, aggressive and metastatic TN/BL tumors overexpress BRCA1-IRIS, AKT and survivin, and lacked BRCA1/p220 expression (Shimizu et al., 2012b). Xenograft tumors developed using HME cells overexpressing BRCA1-IRIS were also invasive, showed increase expression of AKT and survivin and lacked BRCA1/p220 expression (Shimizu et al., 2012).

The experimental evidence of the present disclosure supports, among other things, a role for BRCA1-IRIS overexpression in paclitaxel resistance in TNBC tumors.

Indeed, BRCA1-IRIS overexpression triggers expression of EGFR and ErbB3 expression and activation, activates AKT and ERK, inactivates and/or promotes degradation of FOXO3a and induces survivin expression. BRCA1-IRIS depletion from aggressive TNBC cell lines sensitizes them to EGFR, ErbB2, ERK and PI3'K drugs, in part by de-repressing of FOXO3a. To confirm the utility of using BRCA1-IRIS inhibition as a tool to sensitize TNBC tumors to paclitaxel treatment, the effect of a novel BRCA1-IRIS mimic inhibitory peptide, as a single agent and in combination with paclitaxel, has been developed and pre-clinically validated. IRIS peptide enhanced BRCA1-IRIS protein degradation, reduced tumor proliferation, blocked their aggressiveness and promoted apoptosis in them in in vitro and in vivo. More importantly, as expected treatment with this peptide sensitized TNBCs to low paclitaxel concentrations, in vitro and in vivo. This work shows that BRCA1-IRIS inhibition can be pursued as a novel and effective tool to enhance paclitaxel toxicity and to prevent intrinsic and acquired paclitaxel resistance in TNBC.

Here, it is reported that BRCA1-IRIS activates two autocrine signaling loops, EGF/EGFR-ErbB2 and NRG1/ErbB2-ErbB3, known paclitaxel resistance inducing pathways in breast cancers. With BRCA1-IRIS, these loops are overexpressed in the majority of TNBC cell lines and BRCA1-IRIS silencing or inactivation, using an inhibitory peptide, renders them non-functional in these cells.

In a mouse xenograft model, inhibiting BRCA1-IRIS expression using specific shRNA or activity using this novel inhibitory peptide results in significant reduction in TNBC growth. More importantly, at low concentrations, this peptide sensitized aggressive TNBC cells to low paclitaxel concentrations. Taken together, these data strongly suggest that BRCA1-IRIS could serve as rational target for metastatic TNBCs.

Example 11

BRCA-IRIS Overexpression Induces Paclitaxel Resistance.

An intrinsic cisplatin resistance in ovarian tumors overexpressing BRCA1-IRIS and an acquired cisplatin resistance in normal ovarian surface epithelial or low expressing cancer cells that is correlated with cisplatin (especially at lower concentrations) has been shown to induce BRCA1-IRIS expression (Chock et al., 2010b). Intrinsic or acquired paclitaxel resistance is a serious problem in the treatment of the devastating TNBC (Westerhoff et al., 2000; Mekhail and Markman, 2002). To investigate whether BRCA1-IRIS is also involved in TNBC intrinsic and/or acquired paclitaxel resistance, human mammary epithelial (HME) cells were used to study acquired paclitaxel resistance and HME overexpressing BRCA1-IRIS (hereafter HME/IRIS); and three TNBC cell lines; MDA-MB-231, MDA-MB-468 and BT549 were used to study intrinsic paclitaxel resistance.

Figure 67:
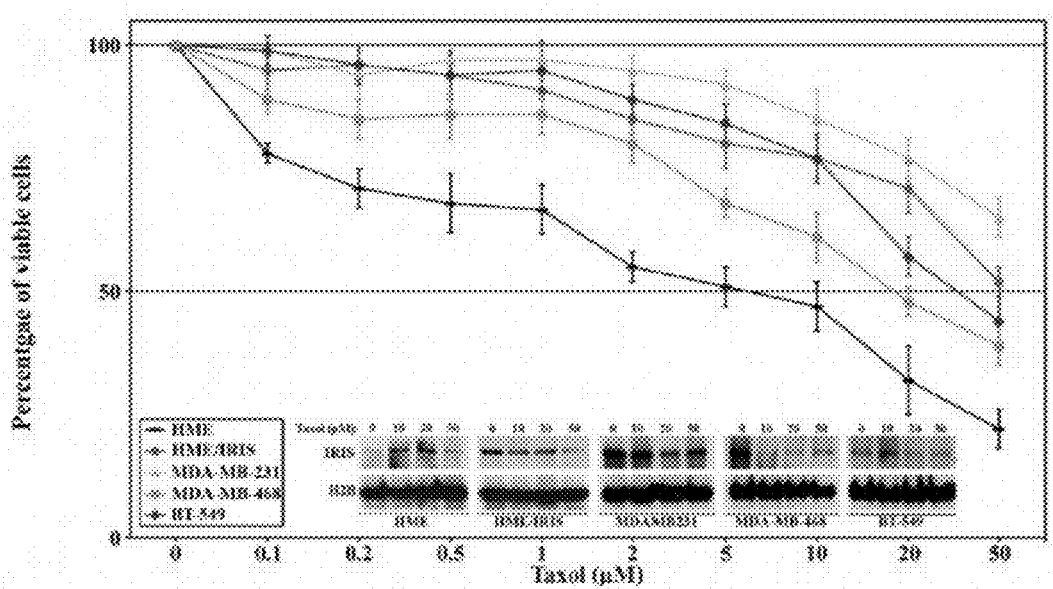
FIG. 67 shows the survival of HME, HME/IRIS and the indicated TNBC cell lines following treatment with increasing concentrations of paclitaxel. Inset shows BRCA1-IRIS expression in these cell lines following exposure to increasing concentrations of Taxol® (paclitaxel). Values represent the means of experiments that were performed in triplicate. BRCA1-IRIS overexpression promotes intrinsic or paclitaxel-acquired resistance in breast cancer cells.

All cell lines were exposed to increasing concentrations of paclitaxel and BRCA1-IRIS expression, and cells' viability was then measured. As expected, HME cells were sensitive to paclitaxel, showing an $IC_{50}$ of ~5 µM (FIG. 67, black line). In agreement with previous reports, MDA-MB-468 was the most sensitive TNBC cell line to paclitaxel (McCloskey et al., 1996; Fang et al., 2000), showing an $IC_{50}$ of <20 µM (FIG. 67, orange line). BT549 cells showed an $IC_{50}$ of ~35 µM (FIG.

1A, blue line); HME/IRIS showed an $IC_{50}$ of ~50 µM (FIG. 67, red line); and MDA-MB-231 showed an $IC_{50}$ of >50 µM (FIG. 67, green line). Interestingly, these $IC_{50}$ values were associated with the expression of BRCA1-IRIS in cells following treatment with different concentrations of paclitaxel. Cell lines that maintained high levels of BRCA1-IRIS following paclitaxel treatment were more resistant to the drug (FIG. 67, inset). These data show a direct correlation between the level of BRCA1-IRIS and the intrinsic paclitaxel resistance in TNBC cells.

Example 12

Survival Pathways Triggered by Low Concentration of Paclitaxel-Induced BRCA1-IRIS Expression.

Figure 68:
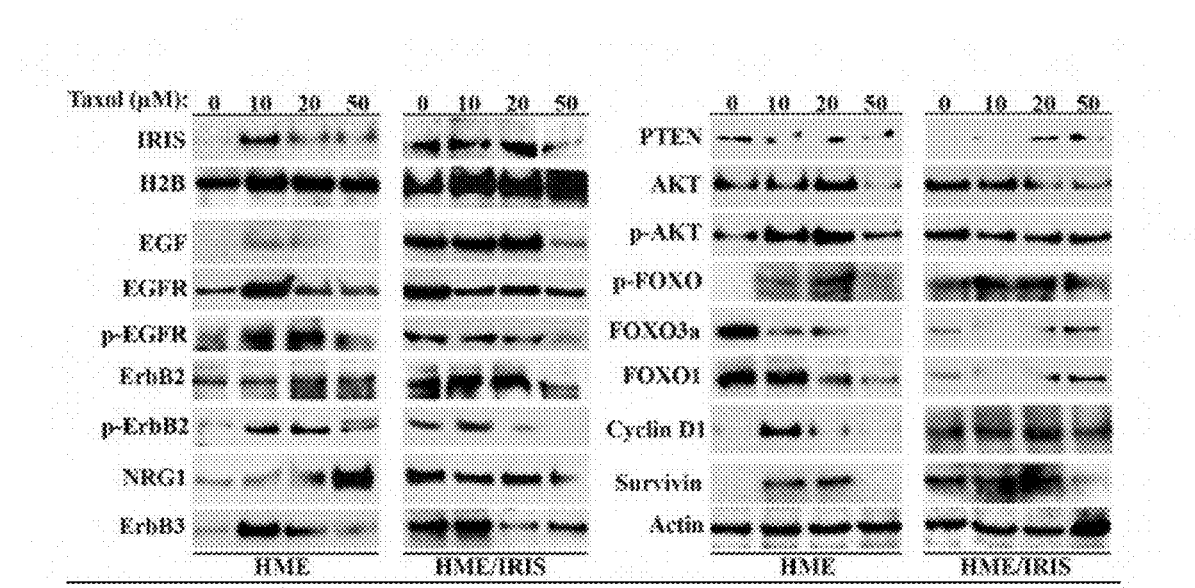
FIG. 68 shows the expression of the indicated proteins in HME or HME/IRIS cells following exposure to 0, 10, 20 or 50 μM of paclitaxel.

HME and HME/IRIS cells were treated with 10, 20 and 50 µM of paclitaxel for 24 hours. Compared to HME/IRIS cells, untreated HME cells express very low level of BRCA1-IRIS (FIG. 68, left). While paclitaxel did not alter the expression of BRCA1-IRIS in HME/IRIS cells until ~50 µM, when it was slightly decreased (FIG. 68, left), low concentrations of paclitaxel, namely 10 and 20 µM significantly upregulated BRCA1-IRIS expression in HME cells (FIG. 68, left). Unlike untreated HME/IRIS that showed high levels of EGFR, ErbB2 and ErbB3 that remained high following paclitaxel treatment (until ~50 µM, FIG. 68, left) in untreated HME cells, paclitaxel (especially low concentrations) increased the expression of EGFR and ErbB3 but not ErbB2 (FIG. 68, left). Both EGF and NRG1, which were secreted at higher levels from untreated HME/IRIS cells, remained high after paclitaxel (until ~50 µM, FIG. 68, left), whereas in HME cells, both were induced by low paclitaxel treatment (FIG. 68, left). Consistently, in HME/IRIS cells EGFR was phosphorylated on Y1173 (activated by EGF when EGFR is in complex with ErbB2) and ErbB2 on Y1248 (activated by NRG1 when ErbB2 is in complex with ErbB3) remained the same after paclitaxel treatment (until ~50 µM, FIG. 68, left). Phosphorylated EGFR-Y1173 and ErbB2-Y1248 was only observed in paclitaxel treated HME cells, especially at low concentration (FIG. 68, left).

In untreated HME/IRIS, PTEN expression was intrinsically low (FIG. 68, right). In contrast, high level PTEN was detected in untreated HME cells but began to decrease following paclitaxel treatment-induced BRCA1-IRIS expression FIG. 68, right). The total AKT level slightly decreased, starting at 50 µM in both cell lines (FIG. 68, right). In contrast, an intrinsic high level of phosphorylated AKT (p-AKT on S308/T473) in untreated HME/IRIS cells remained high after paclitaxel treatment (FIG. 68, right) and an acquired increase following paclitaxel treatment in HME cells (FIG. 68, right). This could be correlated to an intrinsic and an acquired increase in p-FOXO (T32, AKT target site, FIG. 1B, right), which could be matched with decrease in FOXO3a and FOXO1 expression in both cell lines (FIG. 68, right). This led to intrinsic increase in FOXO targets; Cyclin D1 and survivin in untreated HME/IRIS cells, that remained high following paclitaxel treatment (except at ~50 µM, FIG. 68, right), and a paclitaxel acquired increase in their expression in HME cells (especially at 10 and 20 µM, FIG. 68, right). Interestingly, Cyclin D1 and survivin are known targets of BRCA1-IRIS in breast and ovarian cancer cells (Nakuci et al., 2006; Hoa and ElShamy, 2007, Chock et al., 2010a and b).

Example 13

Paclitaxel-Resistance Induced by BRCA1-IRIS Overexpression.

Figure 69:
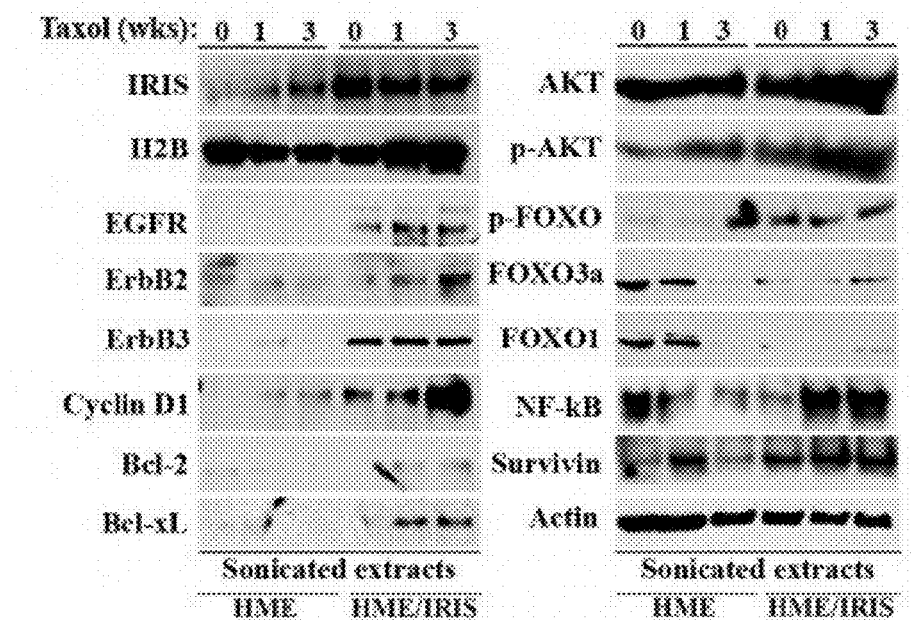
FIG. 69 shows the expression of the indicated proteins in HME versus HME/IRIS cells following exposure to 1 μM of paclitaxel for 0, 1 or 3 weeks.
Figure 70:
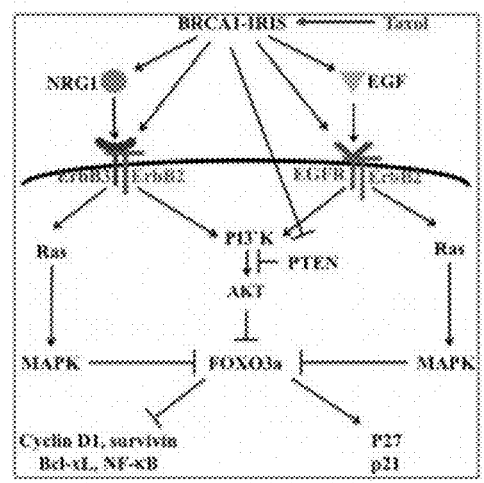
FIG. 70 provides a schematic of the data presented in FIG. 69.

To further confirm these data, HME and HME/IRIS cells were incubated with 1 µM of paclitaxel for 1 or 3 weeks. Survived/paclitaxel-resistant cells were then propagated in the absence of paclitaxel and analyzed. Again, the intrinsically high level of BRCA1-IRIS was not affected by paclitaxel in HME/IRIS cells (FIG. 69, left). In HME cells, even at this low concentration, paclitaxel acquired-induction in BRCA1-IRIS expression was detected (FIG. 69, left). The expressions of EGFR, ErbB2 and ErbB3 were high in HME/IRIS and HME cells (FIG. 69, left). Despite an intrinsic increase in HME/IRIS and paclitaxel-acquired increase in HME cells in AKT activation, FOXO inactivation/degradation and thus activation increase in CyclinD1, survivin, Bcl-2, Bcl-xL and NF-κB was observed (FIG. 69, right). These data suggest that whether intrinsic or paclitaxel-acquired, the elevation in BRCA1-IRIS expression promotes EGFR and ErbB3 expression, which in turn activates AKT that inactivates FOXO3a, which ultimately leads to induction in CyclinD1 and survivin expression. A schematic presentation of these data is shown in FIG. 70.

Example 14

Intrinsic and Paclitaxel-Acquired FOXO3a Degradation by BRCA1-IRIS.

AKT and ERK phosphorylation of FOXO3a promotes its degradation (Huang and Tindall, 2011). It was assessed whether FOXO3a degradation is involved in BRCA1-IRIS overexpression and/or promotion of intrinsic and paclitaxel-acquired resistance. HME and HME/IRIS cells that were made resistant to paclitaxel by exposing them to 1 µM of paclitaxel for 1 or 3 weeks were fractionated into cytoplasmic and nuclear extracts.

Figure 71:
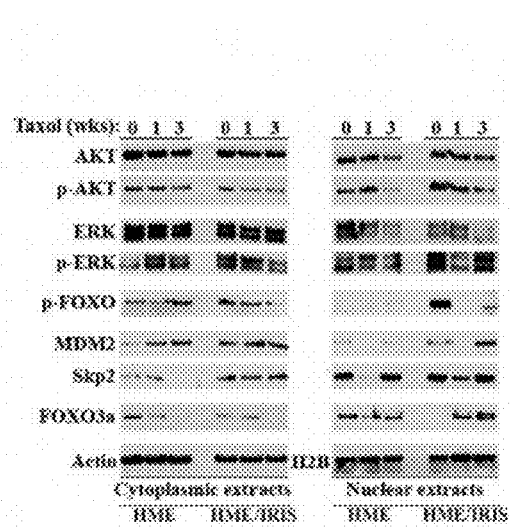
FIG. 71 shows the expression of the indicated proteins in HME versus HME/IRIS cells following exposure to 1 μM of paclitaxel for 0, 1 or 3 weeks.

The expression levels of total AKT in the cytoplasm or the nucleus of both cell lines was similar in parental and paclitaxel-resistant cells (FIG. 71). The expression levels of p-AKT in the cytoplasm and nucleus of HME cells was the same, whereas higher levels of p-AKT in the nucleus than the cytoplasm in parental as well as paclitaxel-resistant HME/IRIS cells was detected (FIG. 71). In HME or HME/IRIS, cells the levels of total ERK in the cytoplasm were similar in parental and paclitaxel-resistant cells (FIG. 71). In the nucleus, however, parental cells showed much higher levels of total ERK than paclitaxel-resistance cells (FIG. 71). In contrast, p-ERK level increased in the cytoplasm of paclitaxel-resistant HME cells (FIG. 71, left), while decreased in the cytoplasm of paclitaxel resistance HME/IRIS cells (FIG. 71, left). In the nucleus, the level of p-ERK decreased slightly in paclitaxel-resistance HME cells (FIG. 71, right) but increased slightly in paclitaxel-resistant HME/IRIS cells (FIG. 71, right). In both cell lines, the level of p-FOXO increased in the cytoplasm, while only in the nucleus of parental HME/IRIS cells (FIG. 71). Similar trends were detected for cytoplasmic and nuclear MDM2 and Skp2 (FIG. 71). These effects together led to significant intrinsic decrease in FOXO3a levels in HME/IRIS and a paclitaxel acquired decrease in HME cells in the cytoplasm and the nucleus (FIG. 71). Together, these data suggest that in paclitaxel-resistant HME cells, an acquired AKT and ERK activation and nuclear translocation occur, whereas in HME/IRIS cells these are intrinsic traits.

Example 15

Additional Signaling Pathways Induced by Intrinsic and Paclitaxel-Acquired BRCA1-IRIS Overexpression.

Figure 72:
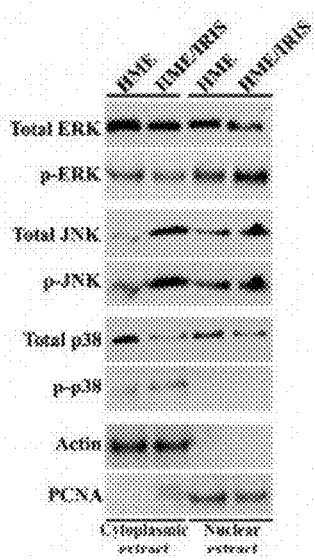
FIG. 72 shows the expression of the indicated proteins as total or phosphorylated/activated proteins in HME or HME/IRIS cells. ERK, .INK and p38 activation was detected by the species phosphorylated on T202/Y204 (for p-ERK), T183/Y185 (for p-JNK), and T180/Y182 (for p-p38).

These data implicate PI'3K/AKT/mTOR pathway in the induction of the paclitaxel-resistance by BRCA1-IRIS overexpression in TNBC cells. To study what other proliferation/survival signaling pathways might be activated by intrinsic or paclitaxel-acquired BRCA1-IRIS overexpression, HME and HME/IRIS cells were fractionated into cytoplasmic and nuclear extracts. The level of total ERK was slightly lower in the cytoplasmic and nuclear extracts of HME/IRIS compared to HME cells (FIG. 72). Although the nuclear extracts from both cell lines contained higher levels of phosphorylated/activated ERK (p-ERK), lower level of p-ERK in HME/IRIS cytoplasmic extract but higher level in nuclear HME/IRIS extract compared to HME extracts was detected (FIG. 72). The level of total and p-JNK was higher in cytoplasmic and nuclear extracts of HME/IRIS cells compared to HME cells (FIG. 72). The level of total p38 was lower in cytoplasmic and nuclear extracts from HME/IRIS cells compared to HME cells, whereas p-p38 was lower in the cytoplasmic extract from HME/IRIS cells compared to HME cells. In nuclear extracts from both cell lines there were no p-p38 (FIG. 72). Taken together, these data suggest that in addition to PI3'K/AKT/mTOR, the MAPK; ERK and JNK are activated in BRCA1-IRIS overexpressing cells (see Nakuci et al., 2006; Hao and ElShamy, 2007) while p38 in inactivated (Chock et al., 2010a)

Figure 73:
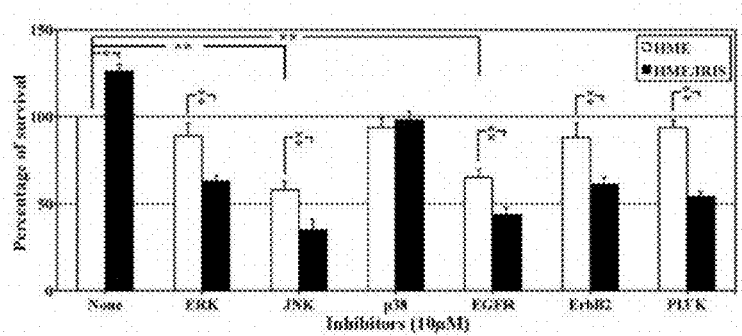
FIG. 73 provides a graph that shows the effect of inhibiting ERK (using PD98059), JNK (using SP600125), p38 (using SB203580), EGFR (using Erlotinib), ErbB2 (using CP-724714) and PI3'K/AKT (using LY294002) on the survival of HME or HME/IRIS cells. Values represent the means of experiments that were performed in triplicate. *=p≤0.05, **=p≤0.001.
Figure 74:
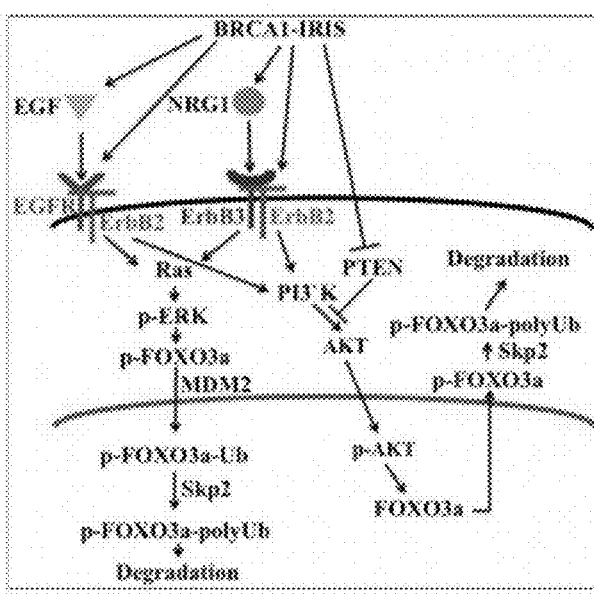
FIG. 74 is a schematic representation of the data from FIGS. 69, 71, and/or 72.

Further, these data imply that BRCA1-IRIS overexpressing cells might be more sensitive to inactivation of these pathways. Similar numbers of HME or HME/IRIS were grown in the presence of 10 µM of ERK (PD98059), JNK (SP600125), p38 (SB203580), EGFR (Erlotinib), ErbB2 (CP-724714) or PI3'K/AKT (LY294002) inhibitors for 24 hours. In keeping with published data (Nakuci et al., 2006; Hao and ElShamy, 2007; Chock et al., 2010a), BRCA1-IRIS overexpression promoted cells proliferation (FIG. 73). Thus, data are represented as percentage of treatment compared to no treatment in each cell line separately. This analysis showed that p38 inhibition had no effect on either cell line, JNK and EGFR inhibition reduced survival of both cell lines, whereas ERK, ErbB2 and PI3'K/AKT inhibition specifically reduced survival in HME/IRIS and not HME cells (FIG. 73). Thus, as expected, cells overexpressing BRCA1-IRIS exerts some of their functions through EGFR/ErbB2 that feeds into PI3'K/AKT/mTOR and MAPK signaling pathways (FIG. 74).

Example 16

BRCA1-IRIS Silencing Sensitizes Breast Cancer Cells to Death Induced by EGFR/ErbB2 or ErbB2/ErbB3 Signaling Pathways Inhibitors.

Figure 75:
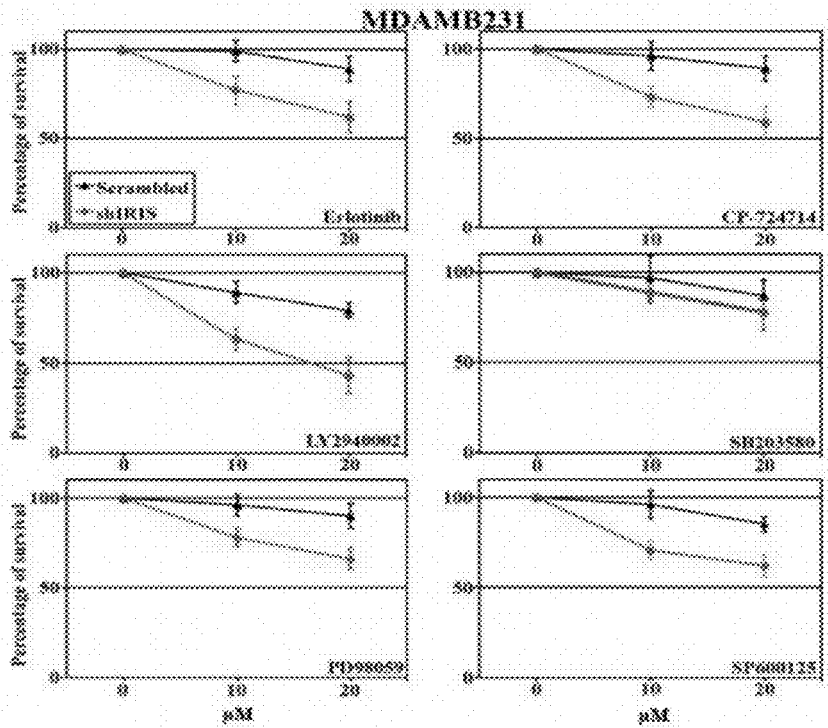
FIG. 75 shows the cooperative effect of BRCA1-IRIS silencing (using cells stably expressing BRCA1-IRIS shRNA) with the inhibition of EGFR (using Erlotinib), ErbB2 (using CP-724714), PI3'K/AKT (using LY294002), p38 (using SB203580), ERK (using PD98059), JNK (using SP600125) on the survival of MDAMB231 cells. Values represent the means of experiments that were performed in triplicates done three separate times.
Figure 76:
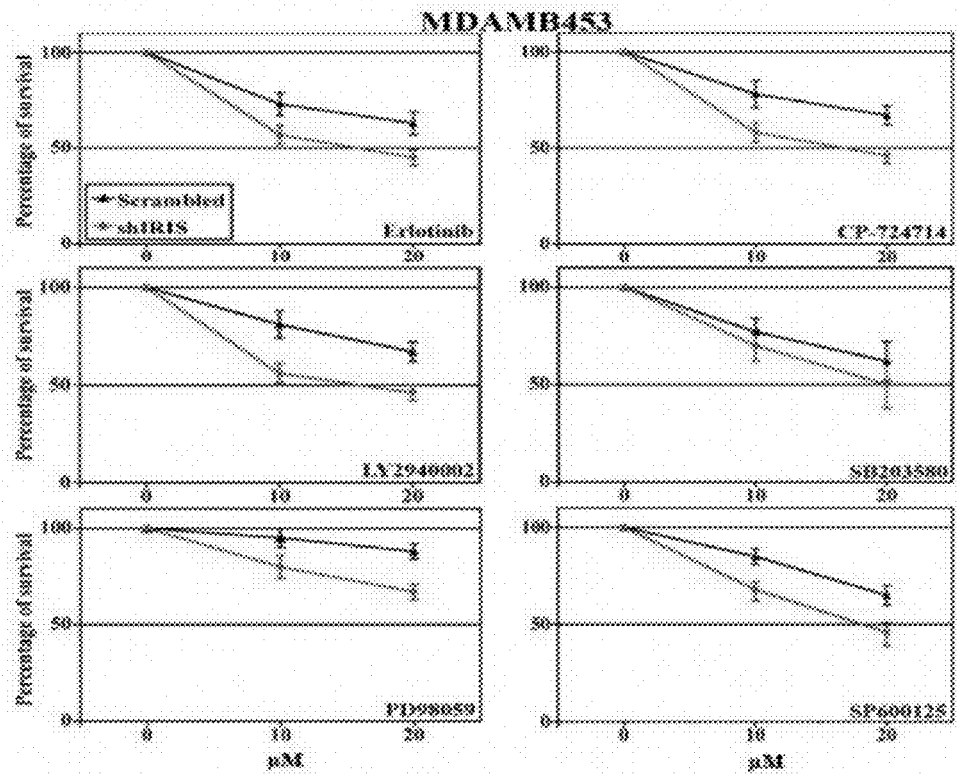
FIG. 76 shows the cooperative effect of BRCA1-IRIS silencing (using cells stably expressing BRCA1-IRIS shRNA) with the inhibition of EGFR (using Erlotinib), ErbB2 (using CP-724714), PI3'K/AKT (using LY294002), p38 (using SB203580), ERK (using PD98059), JNK (using SP600125) on the survival of MDAMB453 cells. Values represent the means of experiments that were performed in triplicates done three separate times.
Figure 77:
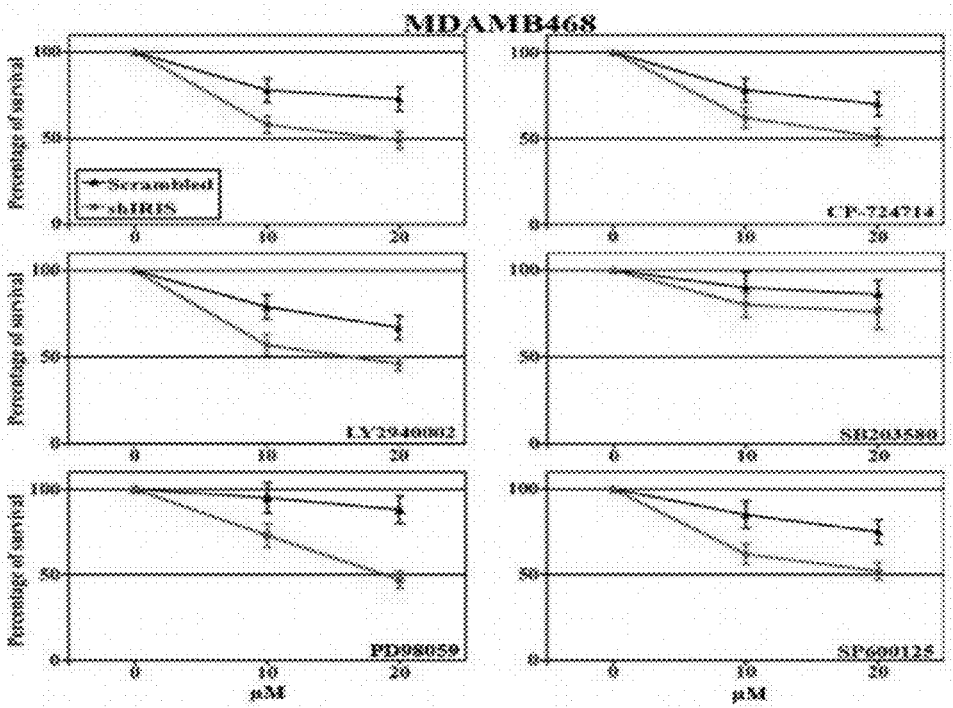
FIG. 77 shows the cooperative effect of BRCA1-IRIS silencing (using cells stably expressing BRCA1-IRIS shRNA) with the inhibition of EGFR (using Erlotinib), ErbB2 (using CP-724714), PI3'K/AKT (using LY294002), p38 (using SB203580), ERK (using PD98059), JNK (using SP600125) on the survival of MDAMB468 cells. Values represent the means of experiments that were performed in triplicates done three separate times.
Figure 78:
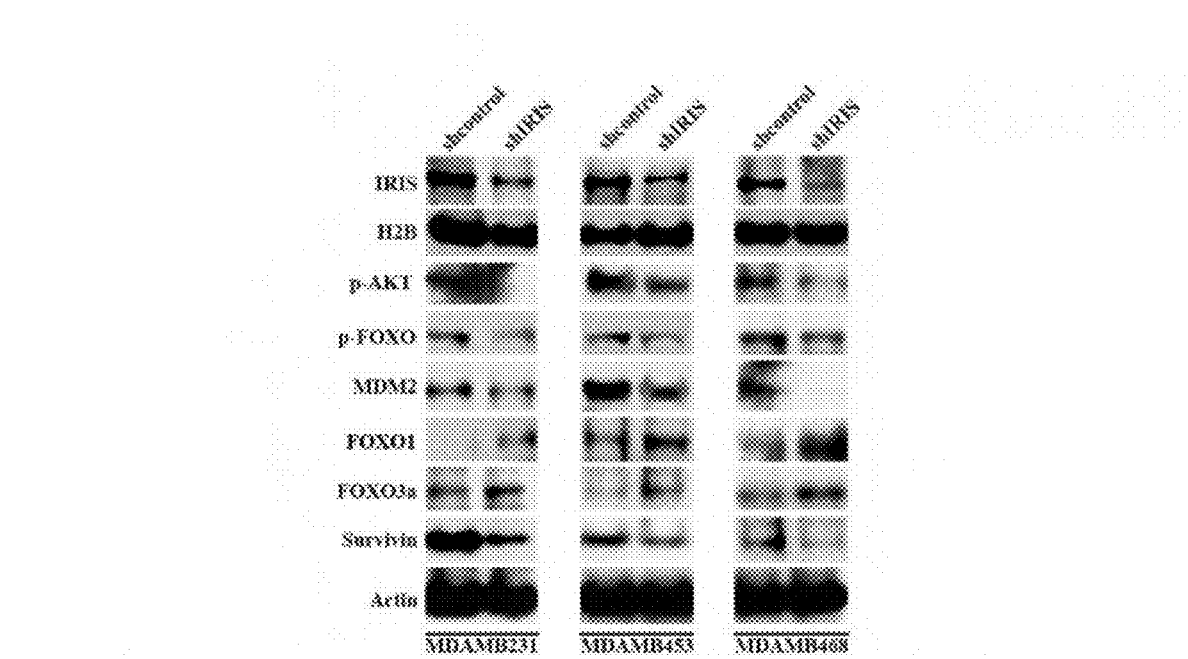
FIG. 78 shows the effect of BRCA1-IRIS silencing following stable expression of BRCA1-IRIS shRNA on the expression of the indicated proteins in MDA-MB-231, MDA-MB-453 and MDA-MB-468 cells, respectively.

To study BRCA1-IRIS overexpression role in TNBC aggressiveness, two TNBC cell lines, MDA-MB-231, MDA-MB-468 and luminal A, MDA-MB-453 (Lehmann et al., 2011) were infected with scrambled or BRCA1-IRIS specific shRNA expressing virus. Stable clones were then exposed to 0, 10 or 20 µM of EGFR (Erlotinib), ErbB2 (CP-724714), PI3'K/AKT (LY294002), p38 (SB203580), ERK (PD98059) or JNK (SP600125) inhibitors for 24 hours. MDA-MB-231 cells: Only LY294002 decreased the survival of scrambled shRNA expressing cells (FIG. 75, black lines). BRCA1-IRIS silencing sensitized cells to death by all except p38 inhibitors (see red lines in FIG. 75). MDA-MB-453 cells: Significant decrease in survival of scrambled shRNA expressing cells was observed in the presence of all except ERK inhibitors (FIG. 76, black lines). BRCA1-IRIS silencing again sensitized cells to death by all the inhibitors (FIG. 76, red lines). MDA-MB-468 cells: All but p38 and ERK inhibitors decreased survival of scrambled shRNA expressing cells, (FIG. 77, black line). BRCA1-IRIS silencing sensitized the cells to all except p38 inhibitor (red lines in FIG. 77). On the molecular level, compared to control shRNA-expressing cells, BRCA1-IRIS shRNA-expressing MDA-MB-231 (FIG. 78, left), MDA-MB-453 (FIG. 78, middle), MDA-MB-468 (FIG. 78, right) showed low p-AKT, p-FOXO3a and MDM2 levels (FIG. 78), which led to accumulation of unphosphorylated FOXO1 and FOXO3a and hence low levels of survivin in the three cell lines (FIG. 78). Together, this data suggests that BRCA1-IRIS silencing in TNBC cells and perhaps cells of other breast cancer subtypes, sensitizes to EGFR, ErbB2, PI3'K/AKT, ERK and JNK inhibitors, in part by downregulating survivin expression.

Example 17

BRCA1-IRIS Silencing Blocks Anoikis-Resistance in TNBC Cells.

Figure 79:
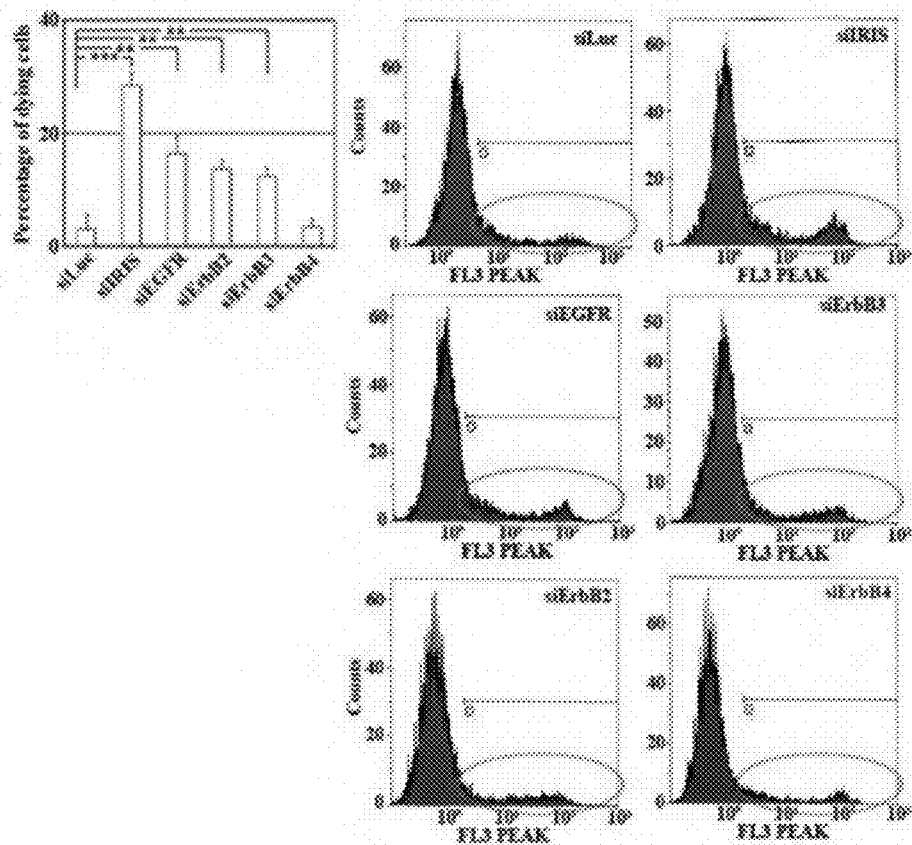
FIG. 79 shows the effect on anoikis resistance in MDA-MB-468 cells following BRCA1-IRIS, EGFR, ErbB2, ErbB3 and ErbB4 silencing using specific siRNAs. Values in the histograms and shown in the representative images inside the ovals represent the means of experiments that were performed in triplicate. Synergy is observed between BRCA1-IRIS and several signal transductions in breast cancer cell lines.

Another property of aggressive breast cancer cells is their ability to resist anoikis, which allows them to survive in the circulation in the absence of attachment. To study whether BRCA1-IRIS, EGFR/ErbB2 or ErbB2/ErbB3 pathways are involved in TNBC cells anoikis resistance, MDA-MB-468 cells were silenced from BRCA1-IRIS, EGFR, ErbB2, ErbB3 and ErbB4 using specific siRNAs for 48 hours. The cells were then trypsinized, and an equal number of each culture was re-plated onto a poly[2-hydroxyethyl methacrylate] (poly-HEMA)-coated dishes for another 24 hours. After that, the floating cells were collected and incubated with propedium iodide (PI) solution for 1 minute and directly analyzed by FACS. Because dying cells' membrane is ruptured, PI can easily diffuse into them; and thus, they can be scored in FACS. This analysis showed that while <3% of luciferase siRNA (control) transfected cells showed PI staining ($PI^+$), >30% of BRCA1-IRIS silenced cells were $PI^+$ (FIG. 79). On the other hand, only 15-18% of EGFR, ErbB2 and ErbB3 silenced cells were $PI^+$ (FIG. 79), while only <3% in ErbB4 silenced cells were $PI^+$ (FIG. 79). These data show that BRCA1-IRIS overexpression is important for MDA-MB-468 cells anoikis resistance. Because the effects are lower in receptor-silenced cells, this data reaffirms that BRCA1-IRIS affect anoikis is through two independent signaling pathways, EGFR/ErbB2 and ErbB2/ErbB3.

Example 18

An Inhibitory BRCA1-IRIS Peptide Abolishes BRCA1-IRIS Expression and Kills TNBC Cells.

Having shown that BRCA1-IRIS overexpression promotes paclitaxel resistance in breast cancer cells, and because a drug that specifically targets BRCA1-IRIS have yet to be developed, other modalities were explored to inhibit BRCA1-IRIS in order to sensitize breast cancer cells to paclitaxel. Published and unpublished data previously showed: 1) BRCA1-IRIS connected with many of its binding partners with a domain in its C-terminus (ElShamy and Livingston, 2004; Nakuci et al., 2006), and 2) unlike full length BRCA1-IRIS, overexpression of an intron-less BRCA1-IRIS (missing the domain expressed by intron 11) failed to induce expression of Cyclin D1, survivin and vimentin (FIG. 25). This data suggests that most if not all BRCA1-IRIS oncogenic functions reside in that intron domain. However, this domain is only 34 amino acid (aa) and holds no structural similarities to any know functional domains in the protein database. It is possible that BRCA1-IRIS uses this domain to establish interactions with other factors and that the complexes and but BRCA1-IRIS per se are oncogenic. If true, it would be possible to inhibit BRCA1-IRIS oncogenic activities by interrupting these interactions.

Figure 80:
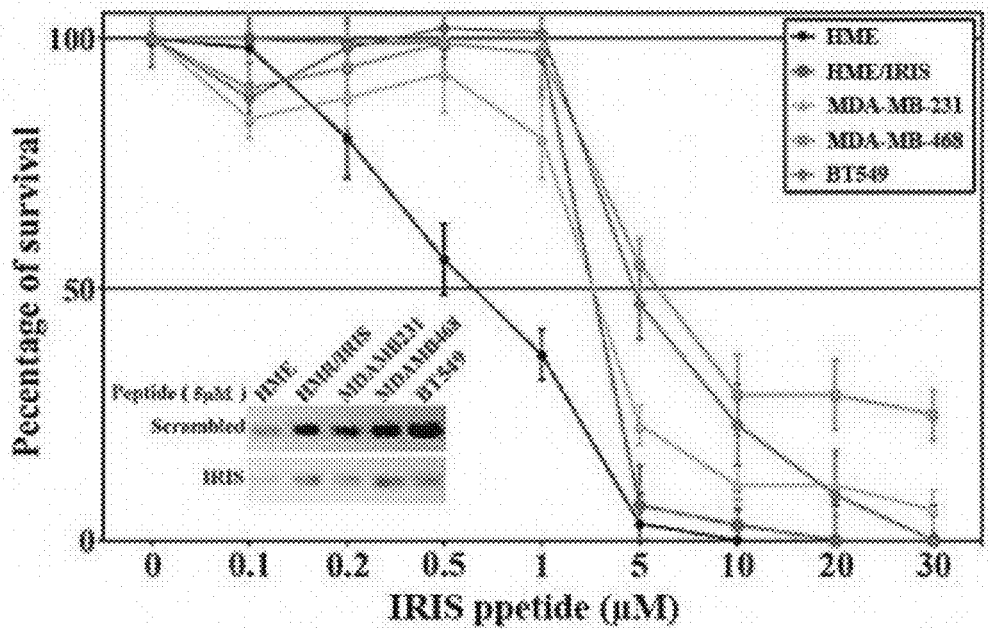
FIG. 80 shows the survival of HME, HME/IRIS and the indicated TNBC cell lines following exposure to increasing concentrations of IRIS peptide. Values represent the means of experiments that were performed in triplicate. The inset shows the effect of 5 μM of IRIS peptide on BRCA1-IRIS expression in these cell lines.

To test that hypothesis, an intron 11 peptide (right in FIG. 26) fused to a cell/nucleus penetrating signal at its N-terminus (left in FIG. 26) was synthesized (hereafter IRIS peptide). First, to assess the effect of this IRIS peptide, equal numbers of HME, HME/IRIS, MDA-MB-231, MDA-MB-468 and BT549 cells were exposed to increasing concentrations of scrambled or IRIS peptide for 48 hours. Percentage of survival comparing the effect of IRIS to scrambled peptide in each cell lines showed, as expected, that BRCA1-IRIS inactivation decreased survival of all cell lines (FIG. 80). The most pronounced effect was seen on HME cells, with an $IC_{50}$ of ~0.5 µM, HME/IRIS and all TNBC cell lines had an $IC_{50}$ of ~5 µM, (FIG. 80). This correlated well with the significant reduction in BRCA1-IRIS expression when these cells were exposed to 5 µM of IRIS peptide for 24 hours (FIG. 80, inset). It is possible that preventing BRCA1-IRIS-X complex formation destabilizes BRCA1-IRIS and perhaps leads to its degradation.

Figure 81:
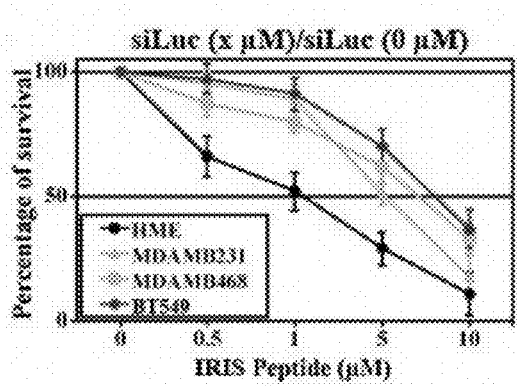
FIG. 81 shows the effect of IRIS peptide on HME and the indicated TNBC cell lines following mock silencing using siRNA.
Figure 82:
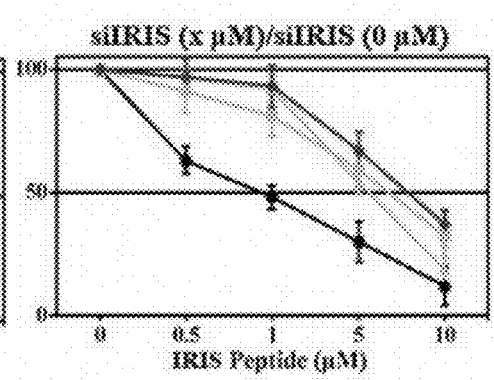
FIG. 82 shows the effect of IRIS peptide on HME and the indicated TNBC cell lines following BRCA1-IRIS silencing using siRNA.
Figure 83:
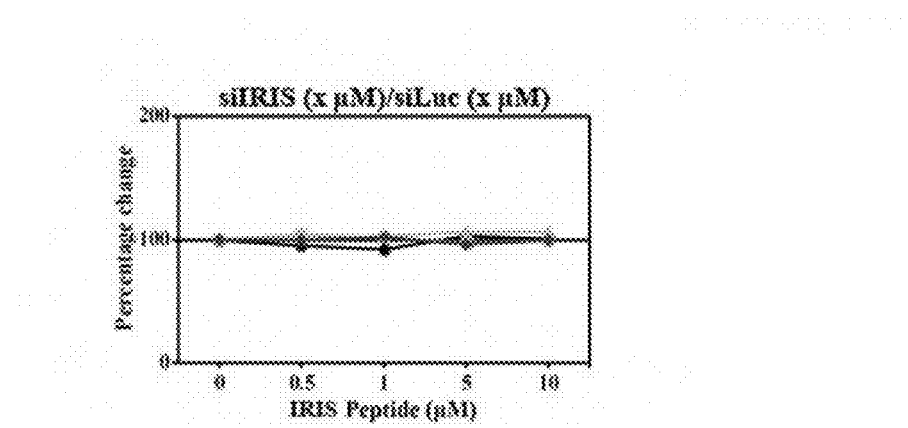
FIG. 83 shows the percentage change between cells treated with the peptide after BRCA1-IRIS silencing compared to control silencing. Values represent the means of experiments that were performed in triplicates, done 3 separate times.

To rule out any off target effect of this peptide, HME, MDA-MB-231, MDA-MB-468 and BT549 cells were first transfected with luciferase (siLuc) or BRCA1-IRIS (siIRIS) siRNA for 48 hours before they were exposed to increasing concentrations of IRIS peptide for an additional 24 hours. As would be expected from treatments that target the same target, whether inactivating BRCA1-IRIS (FIG. 81) or depleting its mRNA first (FIG. 82) the percentages of cells remained following these treatments were identical (see FIG. 83). These data confirm that the peptide is indeed specifically targeting BRCA1-IRIS.

Example 19

BRCA1-IRIS Inhibition Sensitizes Breast Cancer Cells to Low Paclitaxel Concentrations.

Figure 84:
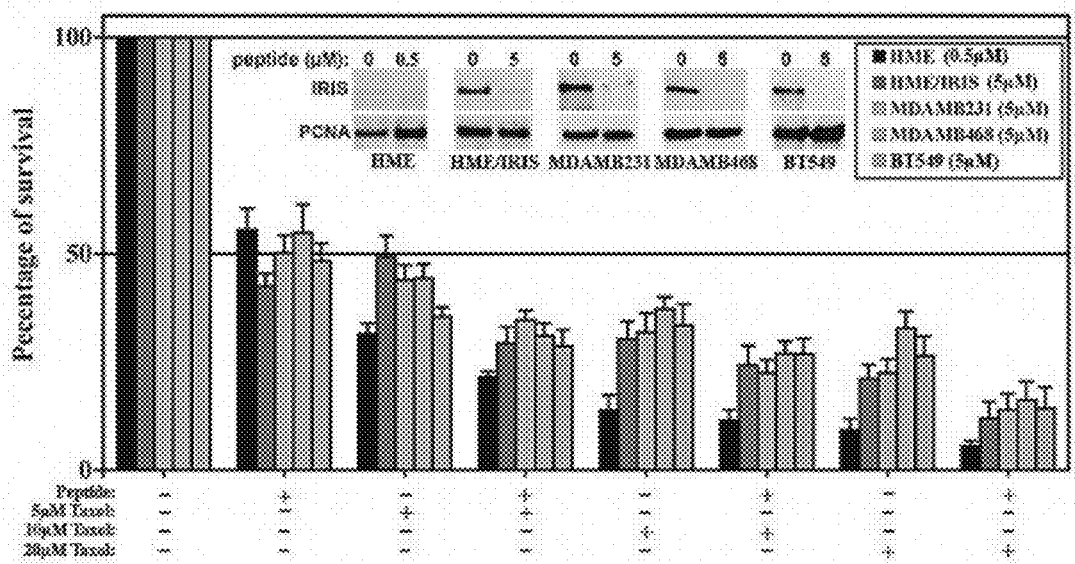
FIG. 84 shows the synergistic effect between certain IRIS peptide concentrations in every cell line (based on $IC_{50}$ for every cell line, as determined in FIG. 80) and 0, 5, 10 and 20 μM of paclitaxel. Values represent the means of experiments that were performed in triplicate. The inset shows the effect of the certain IRIS peptide concentrations on the expression of BRCA1-IRIS in the cell lines.

To investigate whether inactivating BRCA1-IRIS could sensitize TNBC to paclitaxel-induced cell death, HME cells were exposed to 0.5 µM, while HME/IRIS, MDA-MB-231, MDA-MB-468 and BT549 cells were exposed to 5 µM of IRIS peptide alone or with 5, 10 or 20 µM of paclitaxel for 24 hours. In keeping with the data in FIG. 80, IRIS peptide completely abolished BRCA1-IRIS expression in all cell lines (FIG. 84, inset). Again, IRIS peptide alone at these concentrations led to 50% reduction in survival of all cell lines. Paclitaxel alone gradually reduced survival of all cell line with increasing concentration (~50% at 5 µM, ~60% at 10 µM and ~70% at 20 µM, FIG. 84). Impressively, adding IRIS peptide at the concentrations mentioned above significantly increased the killing effect of cisplatin at all concentrations. Indeed, in the presence of IRIS peptide >60%, >70% and >90% reduction in the survival of all cell lines in the presence of 5, 10 and 20 µM of paclitaxel, respectively (FIG. 84).

To assess whether BRCA1-IRIS inactivation can sensitize TNBC cells to lower paclitaxel concentrations, MDA-MB-231 and MDA-MB-468 were exposed to 1 µM of paclitaxel 0, 1, 2, 5 and 10 µM of IRIS peptide for 24 hours. First, at 1 µM, paclitaxel did not affect the survival of either of the cell lines (white bars in FIG. 85). As shown, IRIS peptide reduced survival of both cell lines with an $IC_{50}$ of ~5 µM (light color lines in FIG. 85). This was also confirmed by increase cleaved caspase 3/7 in both cell lines following IRIS peptide treatment (FIG. 86). Perhaps more importantly, in the presence of only 1 µM of paclitaxel, the $IC_{50}$ of IRIS peptide was reduced to <2 µM in both cell lines (dark color lines in FIG. 85). Taken together, these data suggest synergy between very low paclitaxel and IRIS peptide concentrations in killing TNBC cells.

Example 20

IRIS Peptide Inhibits AKT and ERK Activation and Increases FOXO3a Expression.

To relate the effect of IRIS peptide on cell survival to the effect of BRCA1-IRIS on AKT and ERK survival pathways, MDA-MB-231 and MDA-MB-468 were treated with vehicle, 5 µM of IRIS peptide, 10 µM LY294002, 10 µM PD98059 for 24 hours or were transfected with BRCA1-IRIS siRNA for 72 hours. BRCA1-IRIS expression was significantly decreased in both cell lines by BRCA1-IRIS silencing or inactivation (FIG. 87). Notably, however, treatment with LY294002 or PD98059 also significantly reduced BRCA1-IRIS expression in MDA-MB-231 and to a lesser degree in MDA-MB-468 (FIG. 87). Conversely, BRCA1-IRIS silencing or inactivation decreased the levels of total and activated AKT (p-AKT) in both cell lines. LY294002 reduced only p-AKT levels in both cell lines (FIG. 87). These data suggest a positive-feedback loop between BRCA1-IRIS and AKT signaling.

Total ERK1/2 expression was not significantly affected by BRCA1-IRIS silencing or BRCA1-IRIS, AKT or ERK1/2 inactivation (FIG. 87). BRCA1-IRIS silencing did not affect ERK activation (p-ERK) in both cell lines; however, BRCA-IRIS like AKT and ERK inactivation increased instead of decreased p-ERK levels in both cell lines (FIG. 87). Taken together, these data suggest that BRCA1-IRIS and/or AKT inactivation shifts cells towards activating ERK1/2 pathway for survival (FIG. 88), re-enforcing the notion that a positive-feedback mechanism between BRCA1-IRIS and AKT signaling pathways exists. Moreover, since BRCA1-IRIS silenced or inactivated cells still die, this suggests that the AKT is more important than ERK pathway in this context. However, it cannot be ruled out as a possibility that to completely eradicate BRCA1-IRIS overexpressing TNBC, ERK1/2 inhibitors should be combined with AKT or BRCA1-IRIS inhibitors. It is also possible—since ERK1 or ERK2 activation is indistinguishable in these assays—that the two acting in a differential manner. Regardless, the AKT pathway is directly correlated with BRCA1-IRIS role in TNBC survival.

Figure 88:
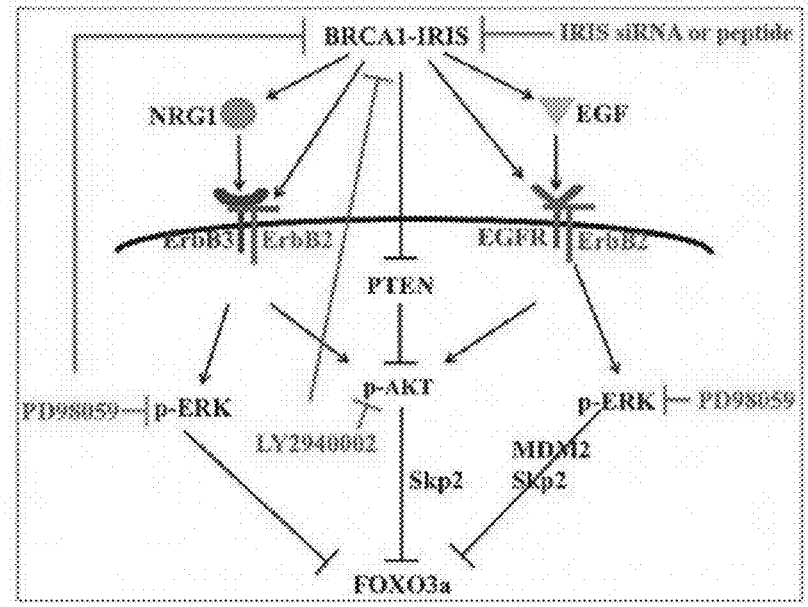
FIG. 88 is a schematic representation of the data presented in FIGS. 80, 84, 85, 86 and 87.

Based on the analysis represented above, BRCA1-IRIS depletion or inactivation, like treatment with LY294002, decreased p-FOXO level and increased the levels of FOXO3a in both cell lines, while PD98059 had no effect (FIG. 87). This was completely in line with decreased MDM2 and Skp2 (the ubiquitin ligases responsible for p-FOXO degradation) expression in BRCA1-IRIS silenced and BRCA1-IRIS and AKT inactivated cells (FIG. 87). Taken together, it is proposed that like BRCA1-IRIS depletion, its inactivation significantly decreases tumor cell survival, sensitize tumor cell lines to low concentration of paclitaxel, in part by inactivating AKT and thus activating of FOXO3a. A schematic representation of these data is shown in FIG. 88.

Example 21

BRCA1-IRIS Silencing or Inactivation Inhibits Aggressive Behavior in Breast Cancer Cell Lines.

Figure 89:
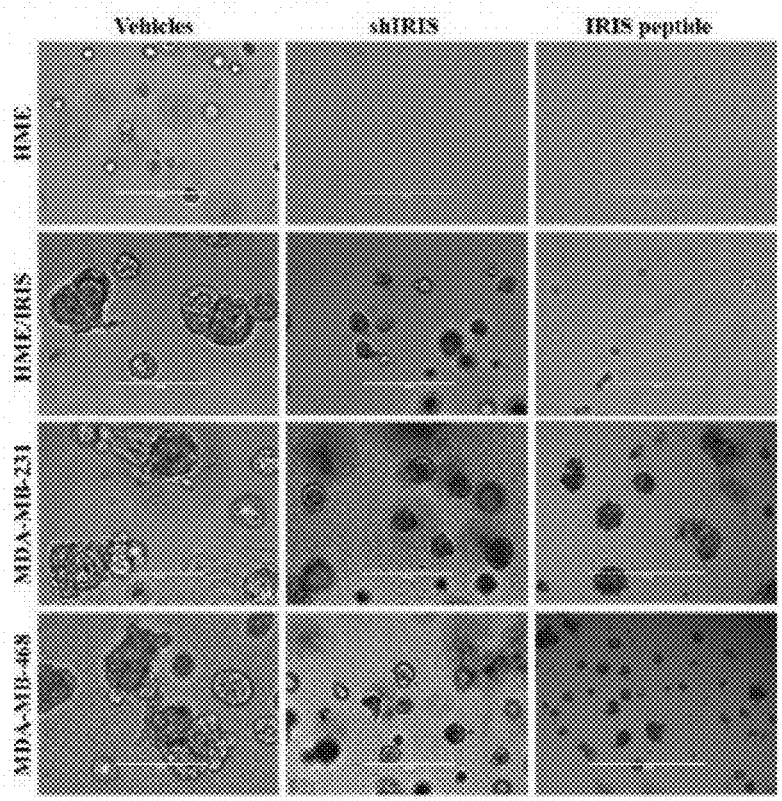
FIG. 89 presents representative images showing acini formation using HME, HME/IRIS, MDA-MB-231 and MDA-MB-468 cell lines at day 10 following no treatment (first column), BRCA1-IRIS silencing (second column) or exposure to 0.5 μM (HME) or 5 μM (HME/IRIS, MDA-MB-231 and MDA-MB-468) IRIS peptide (third column) in matrigel-coated wells.
Figure 90:
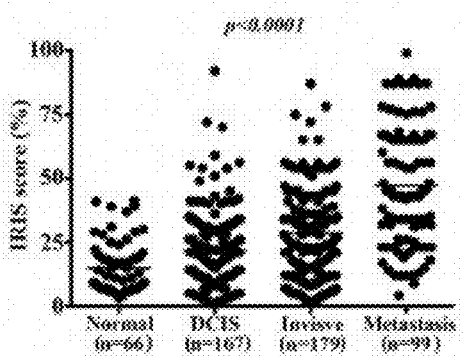
FIG. 90 shows BRCA1-IRIS staining scores in normal (n=66), DCIS (n=167), invasive (n=179) and metastatic (n=99) breast cancer tissue samples found after paraffin-embedded tissue microarray sections were examined by immunohistochemistry.
Figure 91:
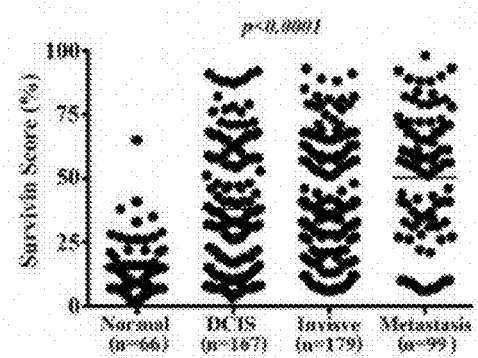
FIG. 91 shows survivin staining scores in normal (n=66), DCIS (n=167), invasive (n=179) and metastatic (n=99) breast cancer tissue samples found after paraffin-embedded tissue microarray sections were examined by immunohistochemistry. Notably, elevated BRCA1-IRIS and survivin and lack of FOXO3a expression are correlated with breast cancer tumor aggressiveness.

Next, it was considered whether BRCA1-IRIS depletion or inactivation could impact the aggressive behavior in breast cancer cell lines. BRCA1-IRIS silenced HME, HME/IRIS, MDA-MB-231 and MDA-MB-468 cells were layered on matrigel-coated wells. Moreover, parental cell lines were layered on the matrigel and grown in the presence of scrambled or IRIS peptide (added every third day). One day later, all cell lines showed small/round acini (Suppl. FIGS. 6A and B). On day 10, HME acini became slightly bigger but remained round (FIG. 89, $1^{st}$ column and FIG. 90). Acini formed by HME/IRIS, MDA-MB-231 and MDA-MB-468 were large/non-round on day 10 (FIG. 89, $1^{st}$ column and FIGS. 90 and 91). BRCA1-IRIS depletion (FIG. 89, $2^{nd}$ column and FIG. 91) or inactivation (FIG. 89, 3rd column and Suppl. FIG. 91) reverted this phenotype back to near normal "small/round" acini. Quantitatively, BRCA1-IRIS overexpression led to >3-fold increase in HME cells aggressiveness, and its depletion or inactivation reduced that phenotype in tumor cells by >3 fold (FIG. 90 and FIG. 91).

Figure 92:
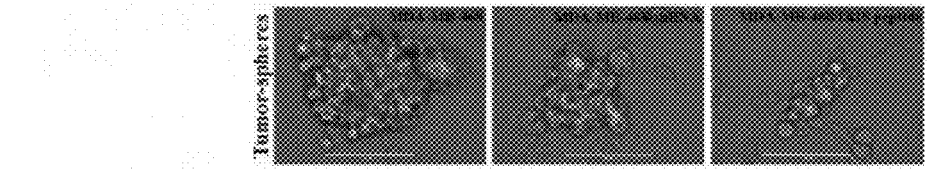
FIG. 92 presents representative images showing mammosphere formation in MDA-MB-468 cells following no treatment (left), BRCA1-IRIS silencing (middle) or inactivation (right) at day 10. BRCA1-IRIS inactivation inhibits aggressiveness in TNBC cell lines.
Figure 93:
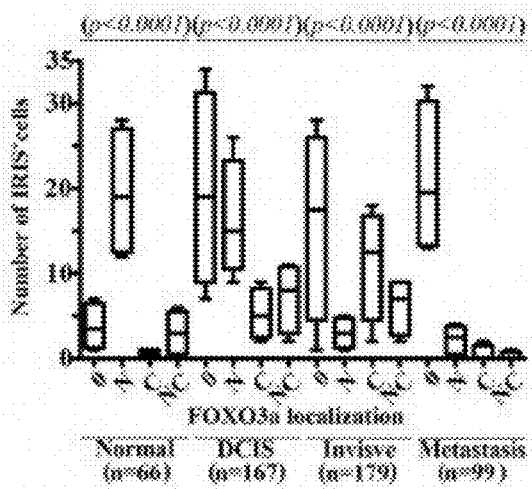
FIG. 93 shows BRCA1-IRIS staining scores per field as compared to the localization of FOXO3a in each cell in normal (n=66), DCIS (n=167), invasive (n=179) and metastatic (n=99) breast cancer tissue samples.
Figure 94:
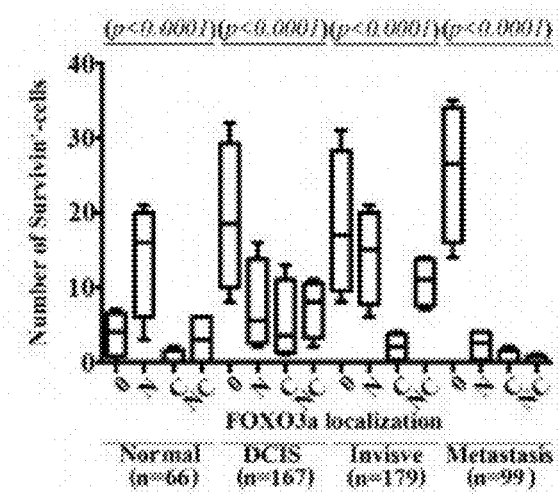
FIG. 94 shows survivin staining scores per field as compared to the localization of FOXO3a in each cells in normal (n=66), DCIS (n=167), invasive (n=179) and metastatic (n=99) breast cancer tissue samples.

Next, MDA-MB-231 and MDA-MB-468 cells expressing shcontrol or shIRIS were plated in ultra low binding dishes or parental cell lines were plated in ultra low binding dishes in the presence or absence of IRIS peptide (added every third day). Ten days later, the number and size of the mammospheres formed by each cell line under each condition was counted and photographed. Again, BRCA1-IRIS silencing or inactivation led to 3-4 fold reduction in the number (FIG. 92 and FIG. 93) and 3-6 fold reduction in the diameter of MDA-MB-231 and MDA-MB-468 mammospheres (FIG. 92 and FIG. 94).

To assess the effect of BRCA1-IRIS silencing on TNBC cell migration, MDA-MB-468 expressing control or BRCA1-IRIS shRNA were plated inside inserts placed in the middle of a well in 24-well plate. When confluent, inserts were removed, dying and dislodged cells were washed away and cells were allowed to migrate outward for 24 hours. The number of cells and the distance each shcontrol expressing cell covered was much greater than those shIRIS expressing cells covered (data not shown). In fact, ~500 fold reduction in cells ability to migrate was measured following BRCA1-IRIS silencing.

Figure 95:
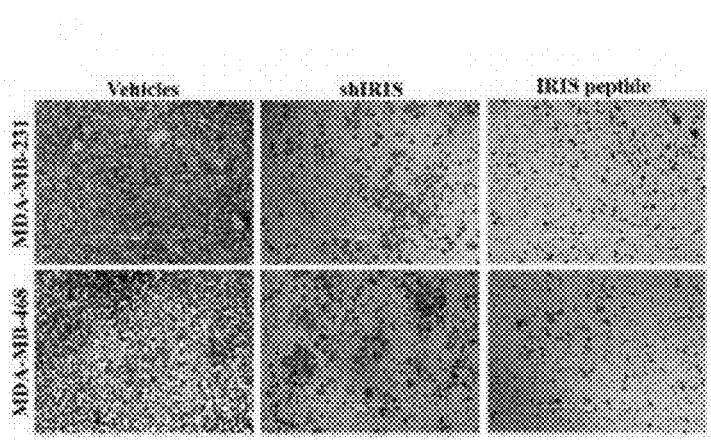
FIG. 95 provides representative images showing the invasion ability of MDA-MB-231 and MDA-MB-468 cells through matrigel-coated Boyden chambers following no treatment (left), BRCA1-IRIS silencing (middle) or inactivation (right) at day 7.
Figure 96:
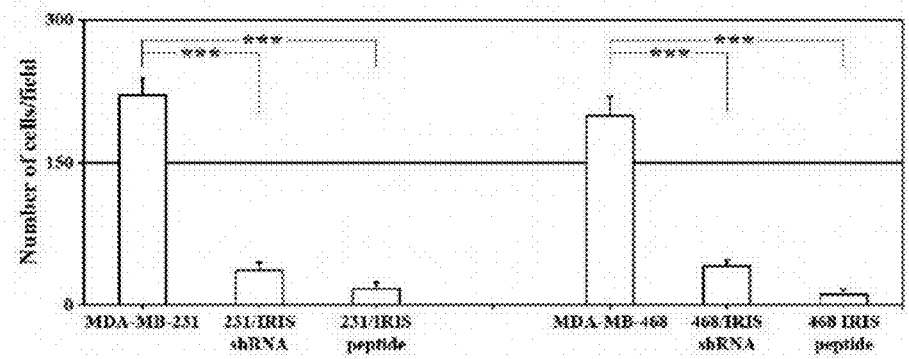
FIG. 96 shows a quantitative analysis of the number and phenotype of acini in the indicated cell lines following BRCA1-IRIS overexpression or silencing at day 10. A number of MDA-MB-231 or MDA-MB-468 cells per field invaded the matrigel and migrated to the lower side of the Boyden chamber, as shown in FIG. 96, following BRCA1-IRIS silencing or inactivation seven days later. Values in all parts represent the means of experiments that were performed in triplicates done three separate times, where =$p \leq 0.001$ and *=$p \leq 0.0001$. BRCA1-IRIS silencing or inactivation decreases aggressiveness in TNBC cells in vitro.
Figure 97:
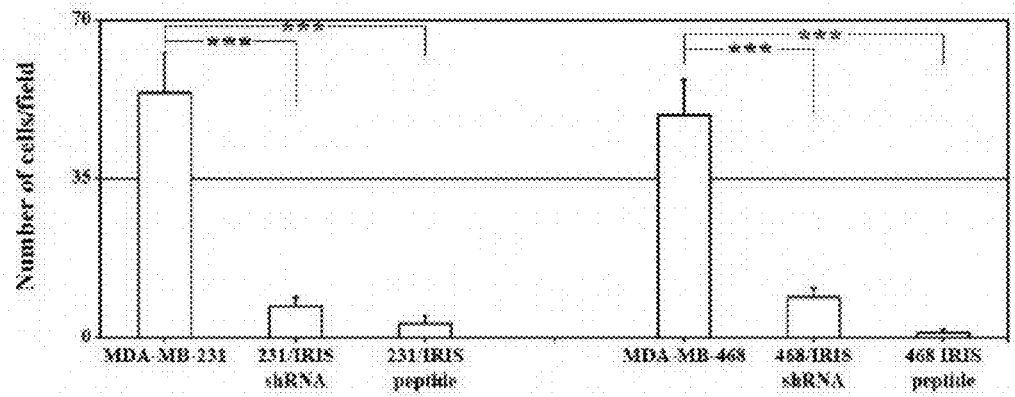
FIG. 97 shows a quantitative analysis of the number and phenotype of acini in the indicated cell lines following BRCA1-IRIS overexpression or silencing at day 10. A number of MDA-MB-231 or MDA-MB-468 cells per field invaded the matrigel and migrated to the lower well, as shown in FIG. 97, following BRCA1-IRIS silencing or inactivation seven days later. Values in all parts represent the means of experiments that were performed in triplicates done three separate times, where =$p \leq 0.001$ and *=$p \leq 0.0001$. BRCA1-IRIS silencing or inactivation decreases aggressiveness in TNBC cells in vitro.
Figure 98:
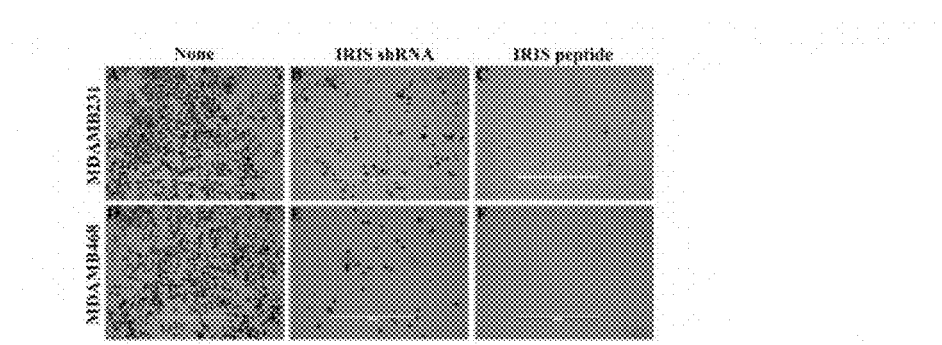
FIG. 98 presents crystal violet staining of untreated MDA-MB-231 or MDA-MB-468 cells (A and D), those stably expressing BRCA1-IRIS shRNA (B and E) or those treated with IRIS peptide (5 µM added every third day, C and F) and shows their respective abilities to invade matrigel-coated Boyden chambers and migrate to the bottom well at day 7. BRCA1-IRIS silencing or inactivation inhibits invasive behavior in TNBC cells.

To study invasion in vitro, matrigel coated Boyden chambers were layered with MDA-MB-231 or MDA-MB-468 cells expressing shcontrol of shIRIS expressing cells, also parental cells were layered and grown in the presence of scrambled or IRIS peptide (added every $3^{rd}$ day). To migrate to the lower side of the chamber or the bottom well, cells must first digest the matrigel. Four days later, a significant number of control treated cells invaded the matrigel and migrated to the lower side of the chambers (FIG. 95, $1^{st}$ column and FIG. 96) and the bottom well (FIG. 97 and FIG. 98, $1^{st}$ column) in both cell lines. BRCA1-IRIS silenced (FIG. 95, 2nd column, FIG. 96 and FIG. 97 and FIG. 98, $2^{nd}$ column) or inactivated (FIG. 95, $3^{rd}$ column, FIG. 96 and FIG. 97 and FIG. 98, $3^{rd}$ column) cells ability to invade and migrate was significantly reduced. Quantitatively, BRCA1-IRIS silencing or inactivation reduced the invasive/migratory ability of these TNBC cells by ~100 fold (FIG. 96 and FIG. 97).

Example 22

Elevated BRCA1-IRIS and Survivin while Lack of FOXO3a Expression in Aggressive Breast Cancer Samples.

Elevated BRCA1-IRIS expression has been shown in ~80% of breast tumors (~900 tumors analyzed, Shimizu et al., 2012b). Thus, the present examples aim to correlate BRCA1-IRIS expression to survivin and FOXO3a expression.

A tissue microarray consisting of normal/cancer adjacent (n=66), DCIS (n=167), invasive (n=179) and metastatic (n=99) samples were immunohistochemically (IHC) stained with anti-BRCA1-IRIS, -survivin and -FOXO3a antibodies. A semi-quantitative scoring system was used in which considering the staining intensity and extent of positivity was adopted. The percentage of tumor cells showing positive staining was first obtained in 4 different high magnification (×60) field of the tumor according to earlier reports (Grayson and Cooper, 2003; Yao et al., 2009; Miller et al., 2002). The consideration of positive staining score was based on validated methods taking in consideration intensity of the nucleic or cytoplasmic staining (no staining=0, weak staining=1, moderate staining=2, strong staining=3) and the extent of stained cells (0%=0, 1-10%=1, 11-50%=2, 51-80%=3, 81-100%=4).

BRCA1-IRIS and survivin expression significantly increases concurrently with the increase in tumor aggressiveness (FIGS. 90 AND 91). Indeed, aside from the fact that more cells per field showed upregulation in BRCA1-IRIS and survivin expression the intensity of the staining itself increased as disease progressed (data not shown). Next, FOXO3a staining in BRCA1-IRIS-positive (IRIS$^+$) and survivin-positive (survivin$^+$) tumors/sections was analyzed. The staining was described as negative (0) when no cells were positively stained, exclusively nuclear (N) when only nuclear staining was observed, exclusively cytoplasmic (C) when only cytoplasmic staining was observed and NC when the staining was observed in both the nucleus and the cytoplasm. Normal IRIS$^+$ or survivin$^+$ tumors/sections show mostly nuclear FOXO3a staining (FIG. 93 and FIG. 94), the majority of IRIS$^+$ or survivin$^+$ DICS tumors/sections were negative or showed nuclear staining (FIG. 93 and FIG. 94), IRIS$^+$ invasive tumors/sections showed negative or showed cytoplasmic FOXO3a staining, while survivin$^+$ invasive tumors were negative or showed nuclear FOXO3a staining (FIG. 93 and FIG. 94), and finally IRIS$^+$ or survivin$^+$ metastatic breast cancer tissues/sections were largely negative for FOXO3a (FIG. 93 and FIG. 94). These data show that during breast cancer progression of, BRCA1-IRIS expression is elevated, which leads to suppression of FOXO3a expression, followed by an increase in surviving expression.

Further, association assessment between BRCA1-IRIS overexpression-signature and disease-free survival (DFS) was conducted using a combined breast cancer cohort from seven Gene Expression Omnibus (GEO) studies (GSE2034, GSE2603, GSE3494, GSE4922, GSE6532, GSE7390 and GSE12093). Patients with positive status of estrogen, progesterone and HER2 were excluded (i.e. only TNBC patients were included), leading to a size of 598 cases. In this analysis, the BRCA1-IRIS signature that was evaluated started with the set "EGFR, ErbB2, AKT, MDM2, Skp2 and survivin" since all were increased by BRCA1-IRIS overexpression. Since ErbB2 was excluded, the set analyzed consisted instead of the 5 genes upregulated by BRCA1-IRIS: "EGFR, AKT, MDM2, Skp2 and survivin" named IRIS-related genes.

Figure 99:
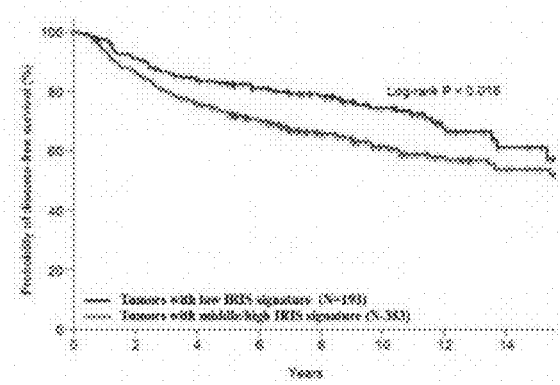
FIG. 99 shows the percentage of probability of disease-free survival in patients with TNBC tumors overexpressing low versus middle/high levels of EGFR/MDM2/Skp2 as a surrogate for BRCA-IRIS overexpression.

The standardized IRIS-related genes expression levels were pooled together and considered as explanatory variables in a Cox model on DFS. Based on the estimation result of the Cox model, a prognostic index was developed, combining the expression levels of IRIS-related genes using the formula: "Prognostic index=EGFR+2×AKT+2×MDM2+2×Skp2+2×survivin". The prognostic index was evaluated for the entire sample. The patient cohort was further categorized into low expressing group versus middle/high expressing group by using the lower tertile as the cutoff value. Kaplan-Meier method was implemented to produce the DFS curves of these two groups. Group-wise comparison in DFS was done using the log-rank test. Analysis of the survival data suggested that patients with low expression levels of the BRCA1-IRIS overexpression-related genes (EGFR, AKT, MDM2, Skp2 and survivin) are associated with longer DFS (FIG. 99, Log-rank p=0.016).

Example 23

BRCA1-IRIS Silencing or Inactivation Blocks TNBC Tumor Formation and Sensitizes Established TNBC Tumors to Low Paclitaxel Concentrations, in vivo.

Figure 100:
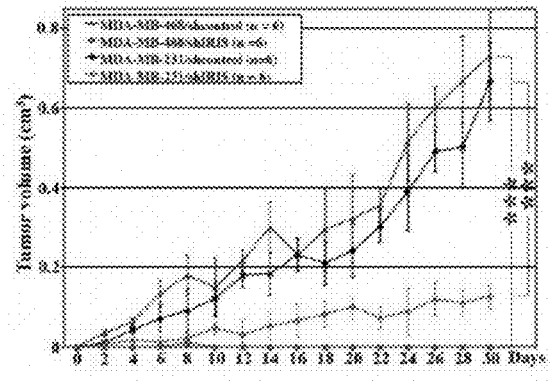
FIG. 100 shows the volumes of tumors developed in SCID mice using MDA-MB-23/shcontrol (line with the second highest tumor volume at day 30, n=6), MDA-MB-231/shIRIS (line with the third highest tumor volume at day 30, n=6), MDA-MB-468/shcontrol (line with the highest tumor volume at day 30, n=6) or MDA-MB-468/shIRIS (line with the lowest tumor volume at day 30, n=6)

Further, whether BRCA1-IRIS overexpression is required for TNBC tumor formation and whether its silencing or inactivation can impact TNBC tumor survival and their response to paclitaxel was addressed in a SCID mice model of TNBC xenografts. Two million MDA-MB-231 or MDA-MB-468 cells expressing vector (control) or BRCA1-IRIS shRNA were injected in the fat pads of 6-8 weeks old female SCID mice (n=6/cell line). Tumor formation was followed daily using caliper. Control shRNA-expressing cells formed tumors that reached ~750 mm$^3$ within four weeks (blue and black lines in FIG. 100), although MDA-MB-231 kinetics were slightly higher (compare blue to black line in FIG. 100). BRCA1-IRIS shRNA expressing MDA-MB-468 cells formed no tumors during this 30-day period (green line in FIG. 100), whereas BRCA1-IRIS silenced MDA-MB-231 formed tumors that did not exceed 100 mm$^3$ in volume (red line in FIG. 100). Quantitatively, BRCA1-IRIS silencing reduced the TNBC cell line; MDA-MB-231 to form tumors by >10-fold and completely blocked the TNBC cell line MDA-MB-468 ability, suggesting that BRCA1-IRIS overexpression is important for TNBC tumor formation.

Next, it was demonstrated that BRCA1-IRIS overexpression is also important for TNBC tumor survival (i.e. maintenance), and it was determined whether BRCA1-IRIS inactivation or inhibition could sensitize TNBC tumors to lower paclitaxel concentrations, in vivo. Nude 6-8 weeks female mice were injected with 2×10$^6$ of MDA-MB-468 cells in the 2$^{nd}$ left and 4$^{th}$ right mammary fat pads. When all tumors reached ~0.1 cm$^3$ in volume, mice were divided into four groups, one received vehicles (i.e. DMSO injected intraperitoneally [i.p.] and scrambled peptide injected directly into tumors [i.t.]), another received paclitaxel (10 mg/kg, i.p.), the third received IRIS peptide at (10 mg/kg, i.t.), and the last received paclitaxel and IRIS peptide at half the concentrations, injected as above. Drugs were delivered every third day for total of four injections.

Figure 101:
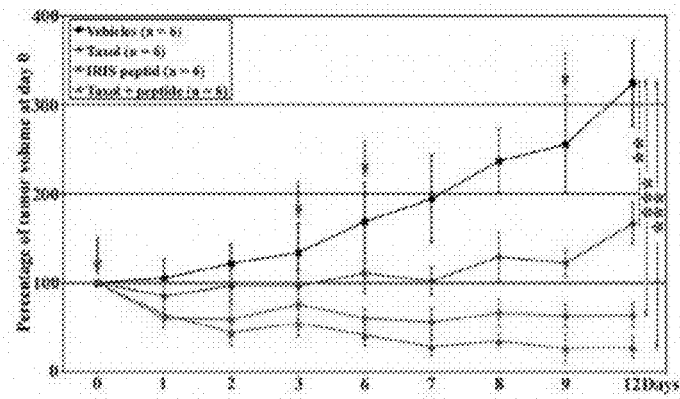
FIG. 101 shows the effect of vehicle (line with the highest percentage of tumor volume at day 12, n=6), paclitaxel (10 mg/kg, delivered i.p., line with the second highest percentage of tumor volume at day 12, n=6), IRIS peptide (10 mg/kg, delivered i.t., line with the third highest tumor volume at day 12, n=6), or both (at half the concentrations, delivered through the same routes, line showing the lowest percentage of tumor volume at day 12, n=6) on an established MDA-MA-468 tumors. Arrows show the times of the drug administration. =$p \leq 0.001$ and *=$p \leq 0.0001$. BRCA1-IRIS overexpression promotes TNBC formation maintenance and its inactivation sensitizes them to low paclitaxel concentrations.
Figure 102:
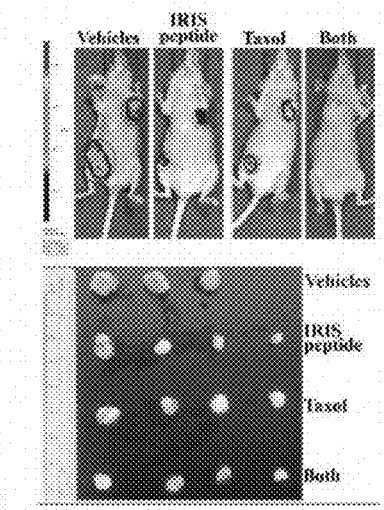
FIG. 102 shows representative images of treated mice as described in FIG. 101 at day 12 (upper) or representative images of tumors isolated from these mice following the treatments also at day 12 (lower).

Tumors in vehicle-treated mice continued to grow exponentially and reached ~0.35 cm$^3$ in 12 days (see black line in FIG. 101 and FIG. 102). Paclitaxel treatment showed some effect, but tumors still grew; however, they only reached half the size of the control tumors in 12 days (see blue line in FIG. 101 and FIG. 102). Impressively, tumors in IRIS peptide treated mice actually regressed during this period and were ~75% of their original size (at day 0) by day 12 (see red line in FIG. 101 and FIG. 102). Also important, tumors in mice treated with both at only half the concentrations also regressed to <25% of their original size (at day 0) by day 12 (see green line in FIG. 101 and FIG. 102). These data show that BRCA1-IRIS is important for TNBC tumor maintenance and its inactivation could sensitize TNBC tumors to lower paclitaxel concentrations, in vivo.

Figure 103:
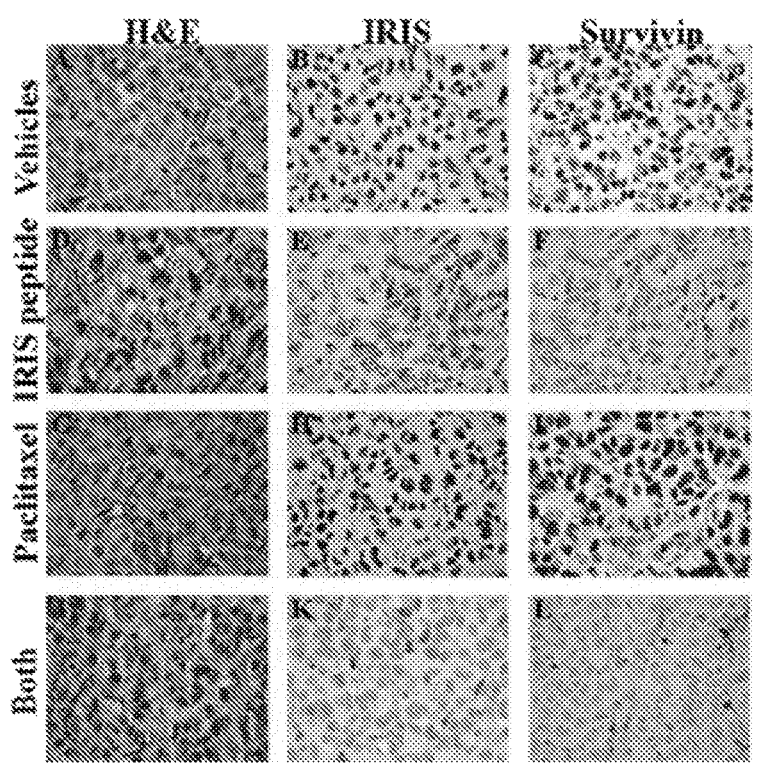
FIG. 103 shows representative images of the sections from TNBC tumors that were stained with hematoxylin and eosin (left) or for BRCA1-IRIS (middle) or survivin (right) using immunohistochemistry.

To study that on the molecular level, sections from these tumors were stained with H&E or for BRCA1-IRIS or survivin using immunohistochemistry. While in control treated tumors BRCA1-IRIS and survivin expressions were high (FIG. 103, upper row), the expression of both was almost completely absent from tumors treated with IRIS peptide (FIG. 103, 2$^{nd}$ row), but, as described above, in vitro, paclitaxel significantly increase BRCA1-IRIS and survivin expression in these tumors (FIG. 103, 3$^{rd}$ row, which perhaps explain the recurrence observed after treatment of patients with this drug). In complete contrast, tumors treated with half the concentrations of both showed complete absence of the expression of both proteins (FIG. 103, 4$^{th}$ row). Accordingly, it is proposed that inactivating BRCA1-IRIS in TNBC patients might sensitize to lower paclitaxel concentrations to avoid the adverse side effects and also to prevent the recurrence of these tumors at a later point.

Experimental Procedures.

Cell culture and Lentiviral transduction. MDA-MB-231, MDA-MB-468, MDA-MB-453 and BT549 cells were grown in RPMI 1640 (Invitrogen, USA) supplemented with 10% FBS. Generation and maintenance of the immortalized mammary epithelial cell (HME) cells was described earlier (ElShamy and Livingston, 2004; Chock et al., 2010a). Ecotropic lentivirus with pLenti6/V5-D-TOPO-vector and pLenti6N5-D-TOPO-BRCA1-IRIS were produced using Lenti-X HTX packaging systems (Clonetech Laboratories, Inc. USA). To generate stable HME/vector and HME/IRIS cell lines, HME cells were transduced with pLenti6/V5-D-TOPO-vector or with pLenti6N5-D-TOPO-BRCA1-IRIS viral supernatant in the presence of 4 µg/mL polybrene (Millipore). Infected cells were selected with blasticidin (10 µg/mL). Cells were also infected with a luciferase expressing retrovirus for in vivo imaging.

Antibodies. The following antibodies were used: Rb anti-survivin (#2808), Rb anti-EGF (ab9695), Rb anti-EGFR (ab23430), m anti-p-EGFR (Y1173; ab24912), Rb anti-p-ErbB2 (ab131104), Rb anti-ErbB3 (ab20161), Rb anti-FOXO3a (ab47409) Rb anti-FOXO1 (ab39670), Rb anti-p-FOXO (T32, ab26649), m anti-H2B (ab52484) and m anti-PCNA (ab18197) were from abcam. Rb anti-ErbB2 (#2165), Rb anti-Cyclin D1 (#2978), Rb anti-PTEN (#9188), Rb anti-AKT (#2938), Rb anti-p-AKT (S463, #4060), Rb anti-ERK (#4695), Rb anti-p-ERK (T202/Y204, #4370), Rb anti-JNK (#9258), Rb anti-p-JNK (T183/Y185, #9255), Rb anti-p38 (#8690), Rb anti-p-p38 (T180/Y182, #2387), Rb anti-Bcl2 (#2870), Rb anti-Bcl-xL (#2762) and Rb anti-Skp2 (#4358) were from Cell Signaling. The m anti-NRG1 (MAB377) was from R&D Systems. Mouse anti-NF-κB/p65 (IMG-150A) and Rb anti-MDM2 (s1357) were obtained from Imgenex and Epitomics, respectively. Mouse anti actin (cp01) was obtained from Calbiochem. Mouse monoclonal anti-human anti-BRCA1-IRIS was developed by the present inventors.

Small hairpin RNA construction and generation of stable knock down cell lines. The small hairpin RNA (shRNA) was designed using 'shRNA Design Tool' from the Integrated DNA Technologies web site. The designed oligonucleotides contain both the sense and antisense siRNA sequences separated by a short loop sequence and have BamHI and EcoR1 compatible overhanging ends for plasmid construction in pSIREN-RetroQ plasmid (Addgene), in which the expression of the shRNA is controlled via the U6 promoter. To establish BRCA1-IRIS shRNA-stable clones, ecotropic retroviral supernatants containing pSIREN-RetroQ-IRISshRNA plasmid or the vector alone were produced. MDAMB231, MDAMB453, MDAMB468 and SKBR3 cells were all infected with retroviral supernatant. Infected cells were selected with puromycin (5 μg/ml). Again, cells were also infected with a luciferase expressing retrovirus for in vivo imaging.

Immunohistochemistry (IHC). Breast tissue microarrays comprised of normal, DCIS, invasive and metastatic were purchased from US Biomax, Inc. Paraffin embedded tissue sections were de-waxed in xylene and rehydrated in alcohol. Antigen-retrieval: for FOXO3a and survivin was by heating the slides in citrate buffer (10 μM, pH 6.0) using microwave (Power level 4) for 10 minutes, for BRCA1-IRIS by incubating slides in pepsin (10 μM) for 20 min at 37° C. Endogenous peroxidase activity was suppressed by treating the slides with 3% $H_2O_2$ for 10 min. Slides were then incubated for 1 hour at room temperature with antibodies to human FOXO3a or survivin (Cell Signaling Technology, USA 1:400), or overnight at 4° C. with monoclonal anti-human BRCA1-IRIS (1:75). Vectastain Elite ABC Kit was used to develop the staining using horseradish peroxidase labeled secondary antibodies (1 hour at room temperature).

Scoring for immunohistochemical staining. All tumors and staining were evaluated under 4× and 10× magnifications. Staining scoring relied on visual examination of multiple fields within a single IHC-stained tissue slice. Scoring represents: overall stain intensity and the percentage of cancer cells stained. Average of overall staining intensity (score, see Hsu et al., 1981) was valued at Zero being negative (<1% of the cells stained); 1=weak (between 1-10% of cells stained); 2=medium (between 10%-50% of cells stained) and 3=strong (>50% of cells stained). The positive staining scoring method is totally subjective and artifacts such as high background or variable stain deposition can skew the results (Choudhury et al., 2010). This method is also limited because the scores for the two categories remain as separate functions and cannot be combined for analysis and comparison (Choudhury et al., 2010).

In vivo tumorigenicity assay. All animal experiments were approved by the 'institutional animal care and use committee' (IACUC) of the University of Mississippi Medical Center. Six to eight week old athymic SCID (NOD.CB17-Prdc$^{scid}$ J, Jackson Laboratory) female mice were used. Two groups of mice were injected subcutaneously with five million MDAMB231 or MDAMB468 expressing control shRNA in the right legs and expressing BRCA1-IRIS shRNA in the left legs (n=6/cell line/shRNA). Tumor growth was monitored weekly by bioluminescent imaging using IVIS™ Imaging System (Xenogen), and daily by visual inspection until tumors became palpable at this time tumors measurements were followed by a caliper and calculated using the formula $4/3\pi r^3$ (where r is the tumor radius). At experiment endpoint, tumors were collected and fixed in 10% formalin for histological and immunohistochemical analysis.

BRCA1-IRIS inhibitory peptide. A synthetic peptide corresponding to amino acids 1365-1399 of BRCA1-IRIS protein conjugated to cell and nuclear penetrating sequence (See FIG. 26) was used as the BRCA1-IRIS inhibitory peptide (IRIS peptide). Peptide was dissolved in water at a concentration of 1 mM and stored in ~80° C.

Cell viability measurement. Cell viability under different experimental conditions was determined using the MTS assay. Briefly, cells ($2.5\times10^4$ cells per well) were seeded in 96-well plates and incubated overnight at 37° C. in 10% humidified $CO_2$ atmosphere. The next day they were incubated with varying concentration of peptide, or inhibitors for 24 hours at 37° C. Cell viability was determined using cell Titer 96® Aqueous (Promega, Madison, Wis., USA) following manufacturer's instructions. Cell viability (%) was expressed as a ratio of treated cells to control cells×100. Growth inhibition was also determined by manually counting cells in five different microscopic fields. Change in cell numbers (fold) was expressed as a ratio of the means of these recording of treated cells compared to control cells×100. Each experiment was done in triplicate, repeated three separate times.

Small interfering RNA transfections. Specific siRNAs for luciferase (negative control) or human BRCA1-IRIS were obtained from Ambion, USA. Transfection was done using Oligofectamine™ reagent (GibcoBRL Inc, USA) and standard protocol (for reference see ElShamy and Livingston, 2004). Knockdwon of the target protein was usually confirmed by Western blotting 72 hours later. Cell viability was evaluated by MTS or by manual counting after 72 hours of siRNA transfection or combined with paclitaxel (24 hour exposure). Each experiment was done in triplicate, repeated three separate times Cell Migration Assay. Cell migration was determined using the μ-Dish (35 mm, high Culture-Inserts, ibidi GmbH, Munich, Germany). Rectangular-shaped inserts surrounded control or BRCA1-IRIS shRNA MDAMB231 or MDAMB468 expressing cells until confluence. At that time inserts were removed, floating cells were removed by washing the monolayer twice with serum-free medium and cells were allowed to migrate outward for 24 hours. Pictures of the whole field (at lower magnification) as well as parts (at higher magnifications) were mounted together to construct a full view, and migration was calculated digitally from fixed points. Each experiment was done in triplicate, repeated three separate times.

Cell Invasion assay. Growth reduced BD Matrigel™ invasion chamber (24 well plate, 8.0 μm, BD BioCoat™) was used to study the invasion ability of control shRNA and BRCA1-IRIS shRNA expressing MDAMB231 cells. Cells ($5\times10^3$) in complete medium (500 μl) were seeded on the upper compartment, and the lower compartment was filled with 750 μl of complete growth medium. Cells were incubated for 7 days, before the medium from the upper chamber was removed, and the cells that remained on the upper surface of the membrane were removed carefully with a cotton swab. Cells invaded into the lower side of the membrane as well as those migrate to the bottom well were stained with Crystal Violet, visualized under microscope, photographed and counted. Each experiments was done in triplicate, repeated three separate times.

Mammo-sphere assay. Sub-confluent MDAMB231, MDAMB468 or SKBR3 monolayer cells were trypsinized and dissociated thoroughly to prepare single cell suspension. One thousand cells were plated per well onto an ultra-low attachment 6-well plates (Corning Life Sciences, Union City, Calif.) in a DMEM/F12 medium supplemented with 10% FBS, 2% B27 (Invitrogen), 10 ng/ml bFGF and 10 ng/ml EGF and incubated at 37° C. in humidified air with 10% $CO_2$. Every third day, a 500 μl of medium containing the treatment required was added to each well. Ten days later, the number of mammo-spheres in each well was counted under an inverted microscope, and mammo-spheres were photographed. Each experiment was done in triplicate, repeated three separate times.

In Vivo efficacy of BRCA1-IRIS-inhibitory peptide. Six to eight week old female athymic SCID mice were injected in the second right and the fourth left mammary gland with $2.5\times10^6$ of MDAMB468 cells. Tumor growth was followed daily until tumors reached 100 mm$^3$. At this time mice were randomly grouped into four different groups that were injected: a) with DMSO (i.p.) and scrambled peptide (10 mg/kg) intra-tumoral (i.t.), b) injected with IRIS peptide (10 mg/kg, i.t.), c) injected with paclitaxel (10 mg/kg, i.p.), d) injected with IRIS peptide (5 mg/kg, i.t.), and paclitaxel (5 mg/kg, i.p.). Peptide and paclitaxel were given every third day for a total of four times/experiment. Change in tumor volume was measured to monitor the efficacy of the treatments using caliper and is represented as percentage of volume at day 0 of treatment. At the endpoint, tumors and/or their remnants were collected and fixed in 10% formalin for histological and immunohistochemical analysis.

DISCUSSION

Intrinsic or acquired paclitaxel resistance is a major problem in oncology. Triple negative breast cancer (TNBC) tumors initially respond to paclitaxel but later show resistance. The aforementioned examples investigate whether BRCA1-IRIS overexpression seen in the majority of TNBCs is involved in paclitaxel resistance.

Summarily, it is established herein that low paclitaxel concentrations trigger BRCA1-IRIS expression, leading to activation of AKT, inactivation of FOXO3a, and both positively impacted survivin expression leading to acquired paclitaxel resistance. Further, it is shown herein that at least two autocrine signaling loops; EGF/EGFR-ErbB2 and NRG1/ErbB2-ErbB3, enhanced by BRCA1-IRIS overexpression, could be involved in this resistance. Treatment with a novel BRCA1-IRIS inhibitory peptide promotes cell death in BRCA1-IRIS overexpressing cells, in vitro and xenograft tumors in vivo. Further, the BRCA1-IRIS peptide sensitized TNBCs to low paclitaxel concentrations. Thus, it is suggested that BRCA1-IRIS as an attractive target for the treatment of paclitaxel resistant TNBCs.

BRCA1-IRIS expression is elevated in the majority of breast cancers, including TNBC, and is correlated with tumor progression, recurrence and metastasis (Shimizu et al., 2012b). One of the fundamental reasons behind breast cancer recurrence and mortality is the development of chemotherapy resistance (Gerber et al., 2010). Anti-mitotic chemotherapeutic agents, like paclitaxel promotes cell death by inducing a permanent mitotic arrest (Weaver and Cleveland, 2005), however, this can lead to adaptation (aka paclitaxel-resistance) and tumor progression (Rieder and Maiato, 2004). Paclitaxel-mediated resistance to therapy has been previously shown in ovarian cancer cells in vitro (Lee and Swain, 2005; Chow et al., 2007). Here, extensive evidence is presented, showing the chemo-resistance-promoting role of BRCA1-IRIS in TNBC cells using both in vitro and in vivo models.

BRCA1-IRIS overexpression drastically diminishes paclitaxel efficacy as evidenced by increased apoptosis of treated cells in vitro and prominent tumors retardation in vivo following BRCA1-IRIS silencing or inactivation using a novel BRCA1-IRIS inhibitory peptide. BRCA1-IRIS is specifically responsible for mediating paclitaxel-resistance by upregulating expression of survivin through activation of AKT and/or inactivation of FOXO3a in vitro and in vivo, in addition to other prominent apoptosis suppressing proteins, such as Bcl-2, Bcl-xL and NF-κB. These findings indicate that BRCA1-IRIS upregulation is involved in the intrinsic, as well as the acquired, paclitaxel resistance in TNBC tumors, and its inhibition can be used as a functional option to prevent tumor resistance and deadly recurrences in TNBC patients.

The specificity of BRCA1-IRIS overexpression that induced acquired paclitaxel resistance is shown here by genetic manipulation of BRCA1-IRIS in three aggressive TNBC lines and by sensitization to lower concentrations of paclitaxel-induced apoptosis, in vitro and in vivo and the corresponding reduction in the aforementioned pathways when BRCA1-IRIS activity was also reduced in these cell lines using the novel IRIS peptide. This was further supported by the fact that one of the most prominent effects of low concentrations paclitaxel induced resistance in HME cells was BRCA1-IRIS overexpression, which was followed by upregulation of the survival pathways described above. Taken together, these data strongly support the notion that whether intrinsically or acquired following paclitaxel (especially low concentrations) treatment, the upregulation in BRCA1-IRIS in TNBC cells is a major obstacle against obtaining major efficacy for paclitaxel, especially in patients with metastatic breast cancer. Therefore, it is proposed that inhibiting BRCA1-IRIS expression and/or activity should sensitize these tumors to paclitaxel and perhaps, as the data suggest, lower and less toxic concentrations of this chemotherapy.

Mechanistically, BRCA1-IRIS-dependent paclitaxel-resistance could be mediated by pro-survival autocrine signaling loops, such as those shown here, namely EGF/EGFR-ErbB2 and NRG1/ErbB2-ErbB3. Although paclitaxel-mediated increases in the expression of some oncogenes have been previously reported in both human patients with breast cancer (Pusztai et al., 2004; Tsavaris et al., 2008) and experimental breast cancer models (Volk et al., 2008; 2011), this is the first study that analyzed co-expression of BRCA1-IRIS and ErbB family members. This evidence strongly suggests that therapy-induced activation of BRCA1-IRIS pathway promotes tumor cell survival through autocrine signaling loops however, secondary pathways activation from the in host environment is also possible. Indeed, the fact that intrinsic or paclitaxel acquired upregulation of BRCA1-IRIS induced expression and activation of NF-κB, as evidence by increase expression and nuclear accumulation of p65 (Chock et al., 2010a and this study) could lead to among other effects, transcription and secretion of a plethora of inflammatory cytokines, such as IL-6, IL-8, TNF-α and MCP-1 that alter the tumor microenvironment through autocrine and paracrine loops (Rajput et al., 2013). Many of these cytokines were recently shown to act in autocrine but mostly in paracrine fashion between tumor cells and the surrounding microenvironment. These factors bind on the surface of stroma cells to specific receptors and induce expression of other factors that promote breast cancer cells aggressiveness in this case in a paracrine manner (Prasad et al., 2010; Eiróet al., 2012; Zubair and Frieri, 2013).

Interestingly, the data of the present disclosure also suggest that BRCA1-IRIS overexpression, which has been shown earlier to be associated with metastasis and poor survival in invasive ductal breast carcinoma, is linked to the uncoupling of the AKT-FOXO3a signaling axis. This conclusion has been reached based on the lack of FOXO3a in the nucleus in more aggressive tumors, which is known to house activated AKT. Thus it was predicted that survivin expression would be positively correlated with BRCA1-IRIS overexpression in aggressive and drug-resistant tumors. This also can explain the fact that paclitaxel failed to induce cell cycle arrest in BRCA1-IRIS overexpressing cells, except after BRCA1-IRIS silencing or inactivation since this would require FOXO3a nuclear translocation to activate gene expression of cell cycle inhibitors, such as p21 and p27, both were not expressed in intrinsic or paclitaxel-acquired BRCA1-IRIS overexpressing cells.

Thus, BRCA1-IRIS signaling in TNBC cells may significantly reduce therapeutic efficacy by promoting survival of damaged cells, which most likely a major reason for the prevalent metastasis detected in TNBC patients overexpressing BRCA1-IRIS. BRCA1-IRIS inactivation should be pursued as a first line therapy to combat TNBC (as well as many other subtypes) metastasis and their drug-resistant recurrence in order to reduce TNBC related motilities.

The presently-disclosed subject matter further includes any references mentioned herein, each which are incorporated in its entirety by this reference.

REFERENCES

Throughout this document, various references are mentioned. All such references, including those listed below, are incorporated herein by reference.

1. Alcantara S, Frisén J, del Rio J A, Soriano E, Barbacid M, Silos-Santiago I. (1997). TrkB signaling is required for postnatal survival of CNS neurons and protects hippocampal and motor neurons from axotomy-induced cell death. J. Neurosci. 17(10), 3623-3633.
2. Auersperg N. (2013). Ovarian surface epithelium as a source of ovarian cancers: Unwarranted speculation or evidence-based hypothesis? Gynecol. Oncol. 130(1), 246-251.
3. Banerjee S, Gore M. (2009). The future of targeted therapies in ovarian cancer. Oncologist. 14(7), 706-716.
4. Birling M C, Price J. (1995). Influence of growth factors on neuronal differentiation. Curr. Opin. Cell Biol. 7(6), 878-884.
5. Blank S V, Christos P, Curtin J P, Goldman N, Runowitcz C D, Sparano J A, Liebes L, Chen H X, Muggia F M. (2010). Erlotinib added to carboplatin and paclitaxel as first-line treatment of ovarian cancer: a phase II study based on surgical reassessment. Gynecol. Oncol. 119, 451-456.
6. Brader S, Eccles S A. (2004). Phosphoinositide 3-kinase signalling pathways in tumor progression, invasion and angiogenesis. Tumori. 90(1), 2-8.
7. Capalbo G, Rödel C, Stauber R H, Knauer S K, Bache M, Kappler M, Rödel F. (2007). The role of survivin for radiation therapy. Prognostic and predictive factor and therapeutic target. Strahlenther Onkol. 183(11), 593-599.
8. Chandarlapaty S, Sawai A, Scaltriti M, Rodrik-Outmezguine V, Grbovic-Huezo Ol Serra V, Majumder P K, Baselga J, Rosen N. (2010). AKT inhibition relieves feedback suppression of receptor tyrosine kinase expression and activity. Cancer Cell. 19(1), 58-71.
9. Chen J, Gomes A R, Monteiro U, Wong S Y, Wu L H, Ng T T, Karadedou C T, Millour J, Ip Y C, Cheung Y N, Sunters A, Chan K Y, Lam E W, Khoo U S. (2010). Constitutively nuclear FOXO3a localization predicts poor survival and promotes Akt phosphorylation in breast cancer. PLoS One. 5(8), e12293.
10. Chen, L., Liang, L., Yan, X., Liu, N., Gong, L., Pan, S., Lin, F., Zhang, Q., Zhao, H., Zheng, F. (2013). Survivin status affects prognosis and chemosensitivity in epithelial ovarian cancer. Int. J. Gynecol. Cancer. 23(2), 256-263.
11. Chock K, Allison J M, ElShamy W M. (2010a). BRCA1-IRIS overexpression abrogates U V-induced p38MAPK/p53 and promotes proliferation of damaged cells. Oncogene. 29(38), 5274-5285.
12. Chock K L, Allison J M, Shimizu Y, ElShamy W M. (2010b). BRCA1-IRIS overexpression promotes cisplatin resistance in ovarian cancer cells. Cancer Res. 70(21), 8782-8791.
13. Chow L, Yip A, Lang B. (2007). A phase II trial of vinorelbine and pegylated liposomal doxorubicin in patients with pretreated metastatic breast cancer. Am. J. Clin. Oncol. 30, 133-138.
14. Choudhury K, Yagle K, Swanson P, Krohn K, Rajendran J. (2010). A Robust Automated Measure of Average Antibody Staining in Immunohistochemistry Images. J Histochem Cytochem. 58(2), 95-107.
15. De Lena M, Latorre A, Calabrese P, Catino A, Lorusso V, Mazzei A, Aloe A. (2000). High efficacy of paclitaxel and doxorubicin as first-line therapy in advanced breast cancer: a phase I-II study. J Chemother. 12(4), 367-373.
16. Dhillon T, Stebbing J, Bower M. (2005). Paclitaxel for AIDS-associated Kaposi's sarcoma. Expert Rev Anticancer Ther. 5(2), 215-219.
17. Douma S, Van Laar T, Zevenhoven J, Meuwissen R, Van Garderen E, Peeper D S. (2004). Suppression of anoikis and induction of metastasis by the neurotrophic receptor TrkB. Nature. 430(7003), 1034-1039.
18. Eiró N, Gonzalez L, Gonzalez L O, Fernandez-Garcia B, Lamelas M L, Marin L, Gonzalez-Reyes S, del Casar J M, Vizoso F J. (2012). Relationship between the inflammatory molecular profile of breast carcinomas and distant metastasis development. PLoS One. 7(11), e49047.
19. Elenbaas B, Spirio L, Koerner F, Fleming M, Zimonjic D, et al (2001) Human breast cancer cells generated by oncogenic transformation of primary mammary epithelial cells. Genes Dev 15(1): 50-65.
20. Ekeblad S, Lejonklou M H, Stalberg P, Skogseid B. (2012). Prognostic relevance of survivin in pancreatic endocrine tumors. World J Surg. 36(6), 1411-1418.
21. ElShamy W M, and Livingston, D M. (2004). Identification of BRCA1-IRIS, a BRCA1 locus product. Nat. Cell Biol. 6(10), 954-967.
22. Engelman J A, Zejnullahu K, Mitsudomi T, Song Y, Hyland C, Park J O, Lindeman N, Gale C M, Zhao X, Christensen J, Kosaka T, Holmes A J, Rogers A M, Cappuzzo F, Mok T, Lee C, Johnson B E, Cantley L C, Janne P A. (2007). MET amplification leads to gefitinib resistance in lung cancer by activating ERBB3 signaling. Science. 316, 1039-1043.
23. Erpolat O P, Gocun P U, Akmansu M, Karakus E, Akyol G. (2012). High expression of nuclear survivin and Aurora B predicts poor overall survival in patients with head and neck squamous cell cancer. Strahlenther Onkol. 188(3), 248-254.
24. Fang M, Liu B, Schmidt M, Lu Y, Mendelsohn J, Fan Z. (2000). Involvement of p21Waf1 in mediating inhibition of paclitaxel-induced apoptosis by epidermal growth factor in MDA-M B-468 human breast cancer cells. Anticancer Res. 20(1A), 103-111.
25. Felsher D W. (2008). Tumor dormancy and oncogene addiction. APMIS. 116(7-8), 629-637.
26. Finnberg N, El-Deiry W S. (2004). Activating FOXO3a, NF-kappaB and p53 by targeting IKKs: an effective multifaceted targeting of the tumor-cell phenotype? Cancer Biol. Ther. 3(7), 614-616.
27. Furuta S, Jiang X, Gu B, Cheng E, Chen P L, et al. (2005). Depletion of BRCA1 impairs differentiation but enhances proliferation of mammary epithelial cells. Proc Natl Acad Sci USA 102(26):9176-81.
28. Geiger T R, Peeper D S. (2007). Critical role for TrkB kinase function in anoikis suppression, tumorigenesis, and metastasis. Cancer Res. 67(13), 6221-6229.
29. Gerber B, Freund M, Reimer T. (2010). Recurrent breast cancer: treatment strategies for maintaining and prolonging good quality of life. Dtsch Arztebl Int. 107(6), 85-91.
30. Gomes A R, Brosens J J, Lam E W. (2008). Resist or die: FOXO transcription factors determine the cellular response to chemotherapy. Cell Cycle. 7(20), 3133-3136.
31. Gordon M S, Matei D, Aghajanian C, Matulonis U A, Brewer M, Fleming G F, Hainsworth J D, Garcia A A, Pegram M D, Schilder R J, Cohn D E, Roman L, Derynck M K, Ng K, Lyons B, Allison D E, Eberhard D A, Pham T Q, Dere R C, Karlan B Y. (2006). Clinical activity of pertuzumab (rhuMAb 2C4), a HER dimerization inhibitor, in advanced ovarian cancer: potential predictive relationship with tumor HER2 activation status. J. Clin. Oncol. 24, 4324-4332.
32. Grayson W, Cooper K. (2003). Application of immunohistochemistry in the evaluation of neoplastic epithelial lesions of the uterine cervix and endometrium. *Curr. Diag. Path.* 9, 19-25.
33. Habashy H O, Rakha E A, Aleskandarany M, Ahmed M A, Green A R, Ellis J O, Powe D G. (2011). FOXO3a nuclear localisation is associated with good prognosis in luminal-like breast cancer. Breast Cancer Res Treat. 129(1), 11-21.
34. Hagenbuchner J, Ausserlechner M J. (2013). Mitochondria and FOXO3: breath or die. Front Physiol. 4, 147.
35. Hao L, ElShamy W M. (2007). BRCA1-IRIS activates cyclin D1 expression in breast cancer cells by downregulating the JNK phosphatase DUSP3/VHR. Int. J. Cancer. 121(1), 39-46.
36. Hondermarck H. (2012). Neurotrophins and their receptors in breast cancer. Cytokine Growth Factor Rev. 23(6), 357-365.
37. Hsu S-M, Raine L, Fanger H. (1981). Use of avidin-biotin-peroxidase complex (ABC) in immunoperoxidase techniques: a comparison between ABC and unlabeled antibody (PAP) procedures. J Histochem Cytochem. 29, 577-580.
38. Hu M C, Lee D F, Xia W, Golfman L S, Ou-Yang F, Yang J Y, Zou Y, Bao S, Hanada N, Saso H, Kobayashi R, Hung M C. (2004). IkappaB kinase promotes tumorigenesis through inhibition of forkhead FOXO3a. Cell. 117(2), 225-237.
39. Huang Y T, Lai P C, Wu C C, Cheng C C, Chiu T H. (2010). TrkB antibody elicits cytotoxicity and suppresses migration/invasion of transitional cell carcinoma cells. Int. J. Oncol. 37(4), 943-949.
40. Huang H, Tindall D J. (2011). Regulation of FOXO protein stability via ubiquitination and proteasome degradation. Biochim. Biophys. Acta. 1813(11), 1961-1964.
41. Jiang L, Cao X C, Cao J G, Liu F, Quan M F, Sheng X F, Ren K Q. (2013). Casticin induces ovarian cancer cell apoptosis by repressing FoxM1 through the activation of FOXO3a. Oncol. Lett. 5(5),1605-1610.
42. Jiménez B, Trigo J M, Pajares B I, Sáez M I, Quero C, Navarro V, Llácer C, Medina L, Rueda A, Alba E. (2013). Efficacy and safety of weekly paclitaxel combined with cetuximab in the treatment of pretreated recurrent/metastatic head and neck cancer patients. Oral Oncol. 49(2), 182-185.
43. Jungbluth S, Koentges G, Lumsden A. (1997). Coordination of early neural tube development by BDNF/trkB. Development. 124(10), 1877-1885.
44. Kadoyama K, Kuwahara A, Yamamori M, Brown J B, Sakaeda T, Okuno Y. (2011). Hypersensitivity reactions to anticancer agents: data mining of the public version of the FDA adverse event reporting system, AERS. J Exp Clin Cancer Res. 30, 93.
45. Kahl B S, Bailey H H, Smith E P, Turman N, Smith J, Werndli J, Williams E C, Longo W L, Kim K M, McGovern J, Jumonville A. (2005). Phase II study of weekly low-dose paclitaxel for relapsed and refractory non-Hodgkin's lymphoma: a Wisconsin Oncology Network Study. Cancer Invest. 23(1), 13-18.
46. Kikuchi S, Nagai T, Kunitama M, Kirito K, Ozawa K, Komatsu N. (2007). Active FKHRL1 overcomes imatinib resistance in chronic myelogenous leukemia-derived cell lines via the production of tumor necrosis factor-related apoptosis-inducing ligand. Cancer Sci. 98(12), 1949-1958.
47. Kim H, Li Q, Hempstead B L, Madri J A. (2004). Paracrine and autocrine functions of brain-derived neurotrophic factor (BDNF) and nerve growth factor (NGF) in brain-derived endothelial cells. *J. Biol. Chem.* 279(32), 33538-33546.
48. Kosmas C, Tsavaris N B, Polyzos A, Kalofonos H P, Sepsas E, Malamos N A, Vadiaka M, Dosios T, Antonopoulos M J. (2000). A phase II study of paclitaxel-ifosfamide-cisplatin combination in advanced non-small cell lung carcinoma. Cancer. 89(4), 774-782.
49. Kupferman M E, Jiffar T, El-Naggar A, Yilmaz T, Zhou G, Xie T, Feng L, Wang J, Holsinger F C, Yu D, Myers J N. (2010). TrkB induces EMT and has a key role in invasion of head and neck squamous cell carcinoma. Oncogene. 29(14), 2047-2059.
50. Lafky J M, Wilken J A, Baron A T, Maihle N J. (2008). Clinical implications of the ErbB/epidermal growth factor (EGF) receptor family and its ligands in ovarian cancer. Biochim. Biophys. Acta. 1785, 232-265.
51. Lee J, Swain S. (2005). Development of novel chemotherapeutic agents to evade the mechanisms of multidrug resistance (MDR). Sem. Oncol. 32, S22-S26.
52. Lehmann B D, Bauer J A, Chen X, Sanders M E, Chakravarthy A B, Shyr Y, Pietenpol J A. (2011). Identification of human triple-negative breast cancer subtypes and preclinical models for selection of targeted therapies. J Clin Invest. 121(7), 2750-2567.
53. Liguang Z, Peishu L, Hongluan M, Hong J, Rong W, Wachtel M S, Frezza E E. (2007). Survivin expression in ovarian cancer. Exp Oncol. 29(2), 121-125.
54. Liu A X, Testa J R, Hamilton T C, Jove R, Nicosia S V, Cheng J Q. (1998). AKT2, a member of the protein kinase B family, is activated by growth factors, v-Ha-ras, and v-src through phosphatidylinositol 3-kinase in human ovarian epithelial cancer cells. Cancer Res. 58(14), 2973-2977.
55. McCormick F. (2011). Cancer therapy based on oncogene addiction. J. Surg. Oncol. 103(6), 464-467.
56. Makhija S, Amler L C, Glenn D, Ueland F R, Gold M A, Dizon D S, Paton V, Lin C Y, Januario T, Ng K, Strauss A, Kelsey S, Sliwkowski M X, Matulonis U. (2010). Clinical activity of gemcitabine plus pertuzumab in platinum-resistant ovarian cancer, fallopian tube cancer, or primary peritoneal cancer. J. Clin. Oncol. 28, 1215-1223.
57. Masana Y, Wanaka A, Kato H, Asai T, Tohyama M. (1993). Localization of trkB mRNA in postnatal brain development. J. Neurosci. Res. 35(5), 468-479.
58. Matsuo K, Lin Y G, Roman L D, Sood A K. (2010). Overcoming platinum resistance in ovarian carcinoma. Expert. Opin. Investig. Drugs. 19(11), 1339-1354.
59. McCloskey D E, Kaufmann S H, Prestigiacomo L J, Davidson N E. (1996). Paclitaxel induces programmed cell death in MDA-M B-468 human breast cancer cells. Clin Cancer Res. 2(5), 847-854.
60. Mekhail T M, Markman M. (2002). Paclitaxel in cancer therapy. Expert Opin Pharmacother. 3(6), 755-66.
61. Miller R T. (2002). Endocervical versus endometrial adenocarcinoma. THE FOCUS—*Immunohistochemistry*. 1-2.
62. Monsalve M, Olmos Y. (2011). The complex biology of FOXO. Curr. Drug. Targets. 12(9), 1322-1350.
63. Nakuci E, Mahner S, Direnzo J, ElShamy W M. (2006). BRCA1-IRIS regulates cyclin D1 expression in breast cancer cells. Exp. Cell Res. 312(16), 3120-3131.
64. Nassar A, Lawson D, Cotsonis G, Cohen C. (2008). Survivin and caspase-3 expression in breast cancer: correlation with prognostic parameters, proliferation, angiogenesis, and outcome. Appl Immunohistochem Mol Morphol. 16(2), 113-120.
65. O'Hanlan K A, Kargas S, Schreiber M, Burrs D, Mallipeddi P, Longacre T, Hendrickson M. (1995). Ovarian carcinoma metastases to gastrointestinal tract appear to spread like colon carcinoma: implications for surgical resection. Gynecol. Oncol. 59(2), 200-206.
66. Okamura K, Harada T, Wang S, Ijichi K, Furuyama K, Koga T, Okamoto T, Takayama K, Yano T, Nakanishi Y. (2012). Expression of TrkB and BDNF is associated with poor prognosis in non-small cell lung cancer. Lung Cancer. 78(1), 100-106.
67. Ozols R F. (2000). Paclitaxel (Taxol)/carboplatin combination chemotherapy in the treatment of advanced ovarian cancer. Semin Oncol. 27(3 Suppl 7), 3-7.
68. Pece S, Chiariello M, Murga C, Gutkind J S. (1999). Activation of the protein kinase Akt/PKB by the formation of E-cadherin-mediated cell-cell junctions. Evidence for the association of phosphatidylinositol 3-kinase with the E-cadherin adhesion complex. J. Biol. Chem. 274(27), 19347-19351.
69. Page C, Lin H J, Jin Y, Castle V P, Nunez G, Huang M, Lin J. (2000). Overexpression of Akt/AKT can modulate chemotherapy-induced apoptosis. Anticancer Res. 20(1A), 407-416.
70. Pal S K, Yamzon J, Sun V, Carmichael C, Saikia J, Ferrell B, Frankel P, Hsu J, Twardowski P, Stein C A, Margolin K. (2013). Paclitaxel-based high-dose chemotherapy with autologous stem cell rescue for relapsed germ cell tumor: clinical outcome and quality of life in long-term survivors. Clin Genitourin Cancer. 11(2), 121-127.
71. Pennati M, Folini M, Zaffaroni N. (2007). Targeting survivin in cancer therapy: fulfilled promises and open questions. Carcinogenesis. 28(6), 1133-1139.
72. Ponnusamy M P, Lakshmanan I, Jain M, Das S, Chakraborty S, Dey P, Batra S K. (2010). MUC4 mucin-induced epithelial to mesenchymal transition: a novel mechanism for metastasis of human ovarian cancer cells. Oncogene. 29(42), 5741-5754.
73. Prasad S, Ravindran J, Aggarwal B B. (2010). NF-kappaB and cancer: how intimate is this relationship. Mol Cell Biochem. 2010336(1-2), 25-37.
74. Puehringer D, Orel N, Lüningschrör P, Subramanian N, Herrmann T, Chao M V, Sendtner M. (2013). EGF transactivation of Trk receptors regulates the migration of newborn cortical neurons. Nat. Neurosci. 16(4), 407-415.
75. Pusztai L, Mendoza T, Reuben J, Martinez M, Willey J, Lara J, et al. (2004). Changes in plasma levels of inflammatory cytokines in response to paclitaxel chemotherapy. *Cytokine* 25, 94-102.
76. Rajput S, Volk-Darper L, Ran S. (2013). TLR4 Is a Novel Determinant of the Response to Paclitaxel in Breast Cancer. Mol. Cancer Ther. 12, 1676-1687.
77. Rieder C, Maiato H. (2004). Stuck in division or passing through: what happens when cells cannot satisfy the spindle assembly checkpoint. Dev. Cell. 7, 637-651.
78. Ricci A, Mariotta S, Pompili E, Mancini R, Bronzetti E, De Vitis C, Pisani L, Cherubini E, Bruno P, Gencarelli G, Giovagnoli M R, Terzano C, Ciliberto G, Giarnieri E, Fumagalli L. (2010). Neurotrophin system activation in pleural effusions. Growth Factors. 28(4), 221-231.
79. Santo E E, Stroeken P, Sluis P V, Koster J, Versteeg R, Westerhout E M. (2013). FOXO3a is a major target of inactivation by PI3K/AKT signaling in aggressive neuroblastoma. Cancer Res. 73(7), 2189-2198.
80. Sergina N V, Rausch M, Wang D, Blair J, Hann B, Shokat K M, Moasser M M. (2007). Escape from HER-family tyrosine kinase inhibitor therapy by the kinase-inactive HER3. Nature. 445, 437-441.
81. Shen J, Yin Q, Chen L, Zhang Z, Li Y. (2012). Co-delivery of paclitaxel and survivin shRNA by pluronic P85-PEI/TPGS complex nanoparticles to overcome drug resistance in lung cancer. Biomaterials. 33(33), 8613-8624.
82. Sheng Q, Liu X, Fleming E, Yuan K, Piao H, Chen J, Moustafa Z, Thomas R K, Greulich H, Schinzel A, Zaghlul S, Batt D, Ettenberg S, Meyerson M, Schoeberl B, Kung A L, Hahn W C, Drapkin R, Livingston D M, Liu J F. (2010). An activated ErbB3/NRG1 autocrine loop supports in vivo proliferation in ovarian cancer cells. Cancer Cell. 17, 298-310.
83. Shimizu Y, Mullins N, Blanchard Z, ElShamy W M. (2012a). BRCA1/p220 loss triggers BRCA1-IRIS overexpression via mRNA stabilization in breast cancer cells. Oncotarget. 3(3), 299-313.
84. Shimizu Y, Luk H, Horio D, Miron P, Griswold M, Iglehart D, Hernandez B, Killeen J, ElShamy W M. (2012b). BRCA1-IRIS overexpression promotes formation of aggressive breast cancers. PLoS One. 7(4), e34102.
85. Siwak D R, Carey M, Hennessy B T, Nguyen C T, McGahren Murray M J, Nolden L, Mills G B. (2010). Targeting the epidermal growth factor receptor in epithelial ovarian cancer: current knowledge and future challenges. J. Oncol. 2010, 568938.
86. Smit M A, Geiger T R, Song J Y, Gitelman I, Peeper D S. (2009). A Twist-Snail axis critical for TrkB-induced epithelial-mesenchymal transition-like transformation, anoikis resistance, and metastasis. Mol. Cell Biol. 29(13), 3722-3737.
87. Smit M A, Peeper D S. (2011). Zeb1 is required for TrkB-induced epithelial-mesenchymal transition, anoikis resistance and metastasis. Oncogene. 30(35), 3735-3744.
88. Storz P, Döppler H, Copland J A, Simpson K J, Toker A. (2009). FOXO3a promotes tumor cell invasion through the induction of matrix metalloproteinases. Mol Cell Biol. 29(18), 4906-4917.
89. Su L, Wang Y, Xiao M, Lin Y, Yu L. (2010). Up-regulation of survivin in oral squamous cell carcinoma correlates with poor prognosis and chemoresistance. Oral Surg Oral Med Oral Pathol Oral Radiol Endod. 110(4), 484-491.
90. Sunters A, Fernandez de Mattos S, Stahl M, Brosens J J, Zoumpoulidou G, Saunders C A, Coffer P J, Medema R H, Coombes R C, Lam E W. (2003). FoxO3a transcriptional regulation of Bim controls apoptosis in paclitaxel-treated breast cancer cell lines. J Biol Chem. 278(50), 49795-49805.
91. Symmans F W. (2001). Breast cancer response to paclitaxel in vivo. Drug Resist. Updat. 4(5), 297-302.
92. Tang C, Lu Y H, Xie J H, Wang F, Zou J N, Yang J S, Xing Y Y, Xi T. (2009). Downregulation of survivin and activation of caspase-3 through the PI3K/Akt pathway in ursolic acid-induced HepG2 cell apoptosis. Anticancer Drugs. 20(4), 249-258.
93. Tanimukai H, Kanayama D, Omi T, Takeda M, Kudo T. (2013). Paclitaxel induces neurotoxicity through endoplasmic reticulum stress. Biochem Biophys Res Commun. 437(1), 151-155.
94. Tanner B, Hasenclever D, Stern K, Schormann W, Bezler M, Hermes M, Brulport M, Bauer A, Schiffer I B, Gebhard S, Schmidt M, Steiner E, Sehouli J, Edelmann J, Läuter J, Lessig R, Krishnamurthi K, Ullrich A, Hengstler J G. (2006). ErbB-3 predicts survival in ovarian cancer. J. Clin. Oncol. 24, 4317-4323.

95. Torti D, Trusolino L. (2011). Oncogene addiction as a foundational rationale for targeted anti-cancer therapy: promises and perils. EMBO Mol. Med. 3(11), 623-636.
96. Tsavaris N, Kosmas C, Vadiaka M, Kanelopoulos P, Boulamatsis D. (2008). Immune changes in patients with advanced breast cancer undergoing chemotherapy with taxanes. Br J Cancer 87, 21-27.
97. Volk L, Flister M, Bivens C, Stutzman A, Desai N, Trieu V, et al. (2008). Nab-paclitaxel efficacy in the orthotopic model of human breast cancer is significantly enhanced by concurrent anti-vascular endothelial growth factor A therapy. Neoplasia 10, 613-23.
98. Volk L, Flister M, Chihade D, Desai N, Trieu V, Ran S. (2011). Synergy of nab-paclitaxel and bevacizumab in eradicating large orthotopic breast tumors and preexisting metastases. Neoplasia, 13:327-338.
99. Waligórska-Stachura J, Jankowska A, Waśko R, Liebert W, Biczysko M, Czarnywojtek A, Baszko-Blaszyk D, Shimek V, Ruchala M. (2012). Survivin—prognostic tumor biomarker in human neoplasms—review. Ginekol Pol. 83(7), 537-540.
100. Weaver B, Cleveland D. (2005). Decoding the links between mitosis, cancer, and chemotherapy: the mitotic checkpoint, adaption, and cell death. Cancer Cell. 8, 7-12.
101. Ween M, Oehler M, Ricciardelli C. (2011). Role of Versican, Hyaluronan and CD44 in Ovarian Cancer Metastasis. Int. J. Mol. Sci. 12, 1009-1029.
102. Wendel H G, De Stanchina E, Fridman J S, Malina A, Ray S, Kogan S, Cordon-Cardo C, Pelletier J, Lowe S W. (2004). Survival signalling by Akt and eIF4E in oncogenesis and cancer therapy. *Nature.* 428(6980), 332-337.
103. Weng D, Song X, Xing H, Ma X, Xia X, Weng Y, Zhou J, Xu G, Meng L, Zhu T, Wang S, Ma D. (2009). Implication of the Akt2/survivin pathway as a critical target in paclitaxel treatment in human ovarian cancer cells. Cancer Lett. 273(2), 257-265.
104. Westerhoff H V, Riethorst A, Jongsma A P. (2000). Relating multidrug resistance phenotypes to the kinetic properties of their drug-efflux pumps. Eur J Biochem. 267 (17), 5355-5368.
105. Wong Y N, Litwin S, Vaughn D, Cohen S, Plimack E R, Lee J, Song W, Dabrow M, Brody M, Tuttle H, Hudes G. (2012). Phase II trial of cetuximab with or without paclitaxel in patients with advanced urothelial tract carcinoma. J Clin Oncol. 30(28), 3545-3551.
106. Xie Y L, An L, Jiang H, Wang J. (2012). Nuclear survivin expression is associated with a poor prognosis in Caucasian non-small cell lung cancer patients. Clin Chim Acta. 414, 41-43.
107. Yang J Y, Hung M C. (2009). A new fork for clinical application: targeting forkhead transcription factors in cancer. Clin. Cancer Res. 15(3), 752-757.
108. Yang J, Mani S A, Donaher J L, Ramaswamy S, Itzykson R A, Come C, Savagner P, Gitelman I, Richardson A, Weinberg R A. (2004). Twist, a master regulator of morphogenesis, plays an essential role in tumor metastasis. *Cell.* 117(7), 927-939.
109. Yang J Y, Zong C S, Xia W, Yamaguchi H, Ding Q, Xie X, Lang J Y, Lai C C, Chang C J, Huang W C, Huang H, Kuo H P, Lee D F, Li L Y, Lien H C, Cheng X, Chang K J, Hsiao C D, Tsai F J, Tsai C H, Sahin A A, Muller W J, Mills G B, Yu D, Hortobagyi G N, Hung M C. (2008). ERK promotes tumorigenesis by inhibiting FOXO3a via MDM2-mediated degradation. Nat Cell Biol. 10(2), 138-148.
110. Yao C, Kok L, Lee M, Wang P, Wu T, Tyan Y, Cheng Y, Kung M, Han C. (2009). Ancillary p16(INK4a) adds no meaningful value to the performance of ER/PR/Vim/CEA panel in distinguishing between primary endocervical and endometrial adenocarcinomas in a tissue microarray study. *Arch Gynecol Obstet.*
111. Yarden Y. (2001). The EGFR family and its ligands in human cancer. Signalling mechanisms and therapeutic opportunities. Eur. J. Cancer. 37 *Suppl* 4, S3-S8.
112. Yu X, Liu L, Cai B, He Y, Wan X. (2008). Suppression of anoikis by the neurotrophic receptor TrkB in human ovarian cancer. Cancer Sci. 99(3), 543-552.
113. Yu Y, Zhang S, Wang X, Yang Z, Ou G. (2010). Overexpression of TrkB promotes the progression of colon cancer. APMIS. 118(3), 188-195.
114. Yue W, Song L, Fu G, Li Y, Liu H. (2013). Neuregulin-1β regulates tyrosine kinase receptor expression in cultured dorsal root ganglion neurons with excitotoxicity induced by glutamate. Regul. Pept. 180, 33-42.
115. Zaffaroni N, Daidone M G. (2002). Survivin expression and resistance to anticancer treatments: perspectives for new therapeutic interventions. Drug Resist. Updat. 5(2), 65-72.
116. Zhang H Y, Zhang P N, Sun H. (2009). Aberration of the PI3K/AKT/mTOR signaling in epithelial ovarian cancer and its implication in cisplatin-based chemotherapy. Eur. J. Obstet. Gynecol. Reprod. Biol. 146(1), 81-86.
117. Zhang Y, Gan B, Liu D, Paik J H. (2011). FoxO family members in cancer. Cancer Biol Ther. 12(4), 253-259.
118. Zheng W, Dai Q, Tao P, Sun A, Wang Y, Bao L, Zhang G. (2011). Overexpression of tyrosine kinase receptor B promotes metastasis of ovarian serous adenocarcinoma by lymphangiogenesis. Tumori. 97(6), 756-761.
119. Zubair A, Frieri M. (2013). Role of nuclear factor-κB in breast and colorectal cancer. Curr Allergy Asthma Rep. 13(1), 44-49.

One of ordinary skill in the art will recognize that additional embodiments and implementations are also possible without departing from the teaching of the present disclosure or the scope of the exemplary claims which follow. This description and, particularly, the specific details of the exemplary implementation disclosed is given primarily for clarity of understanding and no unnecessary limitations are to be understood therefrom, for modifications will be apparent and obvious to one of ordinary skill in the art upon reading this disclosure and may be made without departing from the spirit or scope of the present disclosure.

INCORPORATION BY REFERENCE

All publications, patents, and patent applications mentioned in this description are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

Informal Sequence Listing

| SEQ ID NO. 1: | GIGTRFLCLPQSIYRSELNVYAFGEHILQISKYS (Intron11 IRIS peptide) |
|---|---|
| SEQ ID NO. 2: | RRIRPRPPRLPRPRPRPLPFPRP (Penetrating signal) |

What is claimed is:

1. An isolated peptide, comprising:
the peptide of SEQ ID NO: 1, wherein the N-terminus of the peptide of SEQ ID NO: 1 is fused to the C-terminus of a cell-penetrating peptide.

2. The isolated peptide of claim 1, wherein the isolated peptide is no more than 100 amino acids in length.

3. The isolated peptide of claim 1, wherein the cell-penetrating peptide comprises the peptide of SEQ ID NO: 2.

4. The isolated peptide of claim 3, wherein the isolated peptide is no more than 100 amino acids in length.

5. The isolated peptide of claim 3, comprising the peptide of SEQ ID NO: 1 fused to the C-terminus of the peptide of SEQ ID NO: 2.

6. A pharmaceutical composition, including an isolated peptide comprising the peptide of SEQ ID NO: 1, and a cell-penetrating peptide fused thereto, wherein the N-terminus of the peptide of SEQ ID NO: 1 is fused to the C-terminus of the cell-penetrating peptide; and a pharmaceutically acceptable carrier.

7. The pharmaceutical composition of claim 6, wherein the isolated peptide is an active agent.

8. The pharmaceutical composition of claim 6, wherein the cell-penetrating peptide comprises the peptide of SEQ ID NO: 2.

9. A fusion peptide, comprising:
a first peptide comprising the peptide of SEQ ID NO: 1; and
a second peptide comprising the peptide of SEQ ID NO: 2, wherein the second peptide is a cell-penetrating peptide and the N-terminus of SEQ ID NO: 1 is fused to the C-terminus of the second peptide.

10. The fusion peptide of claim 9, wherein the fusion peptide is no more than 100 amino acids in length.

11. An isolated comprising the peptide of SEQ ID NO: 1, wherein the N-terminus of the peptide of SEQ ID NO:1 is fused to the C-terminus of the peptide of SEQ ID NO: 2.

12. A method of treating ovarian and/or breast cancer, comprising administering to a subject in need thereof a therapeutically effective amount of a peptide comprising the peptide of SEQ ID NO:1, wherein the N-terminus of the peptide of SEQ ID NO:1 is fused to the C-terminus of a cell-penetrating peptide.

13. The method of claim 12, wherein the cell-penetrating peptide comprises SEQ ID NO: 2.

14. The method of claim 13, wherein the peptide is a fusion peptide.

15. A method of treating ovarian and/or breast cancer, comprising administering to a subject in need thereof a therapeutically effective amount of the peptide of claim 9.

16. The method of claim 12, further comprising administering a chemotherapeutic agent to the subject.

17. The method of claim 16, wherein the chemotherapeutic agent comprises cisplatin.

18. The method of claim 16, wherein the chemotherapeutic agent comprises paclitaxel.

* * * * *